US012104175B2

(12) United States Patent
Ramamoorthi et al.

(10) Patent No.: US 12,104,175 B2
(45) Date of Patent: Oct. 1, 2024

(54) HIGH ACTIVITY REGULATORY ELEMENTS

(71) Applicant: Encoded Therapeutics, Inc., South San Francisco, CA (US)

(72) Inventors: Kartik Ramamoorthi, San Francisco, CA (US); Stephanie Tagliatela, San Francisco, CA (US); Anne Tanenhaus, Brisbane, CA (US); Andrew Young, Redwood City, CA (US); Szu-Ying Chen, San Francisco, CA (US); Chi Zhang, Daly City, CA (US); Stephanie Martin, San Francisco, CA (US); David Oberkofler, San Francisco, CA (US)

(73) Assignee: Encoded Therapeutics, Inc., South San Francisco, CA (US)

( * ) Notice: Subject to any disclaimer, the term of this patent is extended or adjusted under 35 U.S.C. 154(b) by 1000 days.

(21) Appl. No.: 16/687,426

(22) Filed: Nov. 18, 2019

(65) Prior Publication Data
US 2020/0231943 A1 Jul. 23, 2020

Related U.S. Application Data

(63) Continuation of application No. PCT/US2018/033515, filed on May 18, 2018.

(60) Provisional application No. 62/508,968, filed on May 19, 2017.

(51) Int. Cl.
*C12N 7/00* (2006.01)
*A61K 48/00* (2006.01)
*A61P 1/16* (2006.01)
*A61P 7/02* (2006.01)
*C12N 15/86* (2006.01)

(52) U.S. Cl.
CPC ............... *C12N 7/00* (2013.01); *A61K 48/005* (2013.01); *A61P 1/16* (2018.01); *A61P 7/02* (2018.01); *C12N 15/86* (2013.01); *C12N 2750/14121* (2013.01); *C12N 2750/14132* (2013.01); *C12N 2750/14142* (2013.01); *C12N 2750/14143* (2013.01)

(58) Field of Classification Search
CPC ............ A61K 48/005; A61P 1/16; A61P 7/02; C12N 15/86; C12N 2830/00
See application file for complete search history.

(56) References Cited

U.S. PATENT DOCUMENTS

| | | | |
|---|---|---|---|
| 2003/0017139 A1 | 1/2003 | Souza et al. | |
| 2005/0196754 A1 | 9/2005 | Drmanac et al. | |
| 2009/0062135 A1 | 3/2009 | Delfour et al. | |
| 2015/0273029 A1 | 10/2015 | Gruber et al. | |
| 2020/0397917 A1* | 12/2020 | Tagliatela | A61K 48/005 |
| 2022/0193264 A1* | 6/2022 | Wood | A01K 67/0276 |

FOREIGN PATENT DOCUMENTS

| | | |
|---|---|---|
| CA | 2985624 A1 | 6/2016 |
| EP | 2698163 A1 | 2/2014 |
| WO | WO-0136620 A2 | 5/2001 |
| WO | WO-2008073303 A2 | 6/2008 |
| WO | WO-2013033627 A2 | 3/2013 |
| WO | WO-2013123503 A1 | 8/2013 |
| WO | WO-2016164609 A2 | 10/2016 |
| WO | WO-2018213786 A1 | 11/2018 |

OTHER PUBLICATIONS

Sequence alignment for exemplar sequences Seq ID No. 1, 2, 13 and 22 (Year: 2023).*
Sakharkar et al. Distributions of Exons and Introns in the Human Genome. In Silico Biology, vol. 4, 2004 (Year: 2004).*
Le et al (Classifying Promoters by Interpreting the Hidden Information of DNA Sequences via Deep Learning and Combination of Continuous FastText N-Grams. Frontiers in Bioengineering and Biotechnology, vol. 7, Nov. 2019) (Year: 2019).*
Willyard. Expanded human gene tally reignites debate. Nature, vol. 558, Jun. 2018). (Year: 2018).*
Seq ID 1 and 2 sequence alignment (Year: 2023).*
Shaul (How introns enhance gene expression. Int Journal of Biochem and Cell Bio, vol. 91, Jul. 2017) (Year: 2017).*
Furger et al (Promoter proximal splice sites enhance transcription. Genes & Dev, vol. 16, 2002) (Year: 2002).*
Samadder et al (Transcriptional and post-transcriptional enhancement of gene expression by the 5' UTR intron of rice rubi3 gene in transgenic rice cells. Mol Genet Genomics, vol. 279, 2008) (Year: 2008).*
Morello et al (Testing the IMEter on rice introns and other aspects of intron-mediated enhancement of gene expression. Journal of Exp Botany, vol. 62, 2010). (Year: 2010).*
Definition of expression cassette (Year: 2023).*
European Application No. 18803184 Search Report dated Feb. 22, 2021.
Choi et al., A Generic Intron Increases Gene Expression in Transgenic Mice, Mol. Cell. Biol., 11(6): 3070-3074 (1991).
Li et al., A small regulatory element from chromosome 19 enhances liver-specific gene expression, Gene Therapy, 16: 43-51 (2009).
Mcintosh et al., Therapeutic levels of FVIII following a single peripheral vein administration of rAAV vector encoding a novel human factor VIII variant, Blood, 121(17): 3335-3344 (2013).
Ostedgaard et al., A shortened adeno-associated virus expression cassette for CFTR gene transfer to cystic fibrosis airway epithelia, PNAS, 102(8): 2952-2957 (2005).
PCT/US2018/033515 International Search Report and Written Opinion dated Oct. 22, 2018.
Rose, Intron-mediated regulation of gene expression, Curr Top Microbiol Immunol., 326: 277-290 (2008).

(Continued)

Primary Examiner — Valerie E Bertoglio
Assistant Examiner — Matasha Dhar
(74) Attorney, Agent, or Firm — Wilson Sonsini Goodrich & Rosati

(57) ABSTRACT

Provided herein are compositions and methods for driving high expression of a transgene. Compositions and methods for driving high expression of a transgene comprising one or more human-derived regulatory elements, which, when operably linked to a transgene, can result in high expression of the transgene in one or more cell types or tissues.

32 Claims, 23 Drawing Sheets

Specification includes a Sequence Listing.

(56) References Cited

OTHER PUBLICATIONS

Wootton, et al. Statistics of local complexity in amino acid sequences and sequence databases. Computers & Chemistry. vol. 17, Issue 2, Jun. 1993, pp. 149-163.

Wu et al., Optimization of Self-complementary AAV Vectors for Liver-directed Expression Results in Sustained Correction of Hemophilia B at Low Vector Dose, Molecular Therapy, 16(2): 280-289 (2008).

Yan et al. Optimization of Recombinant Adeno-Associated Virus-Mediated Expression for Large Transgenes, Using a Synthetic Promoter and Tandem Array Enhancers. Human Gene Therapy 26:334-346 (Jun. 2015). DOI: 10.1089/hum.2015.001.

EP18803184.3 Partial Supplementary European Search Report dated Feb. 22, 2021.

EP18803184.3 Supplementary European Search Report dated May 26, 2021.

GenBank Accession: AAA52484 factor (1994).

GenBank Accession: K01740.1 Human coagulation factor (1994).

PCT/US2018/033515 International Preliminary Report on Patentability dated Nov. 28, 2019.

* cited by examiner

Negative

EFS minCMV

SEQ ID NO: 4

HIGH ACTIVITY REGULATORY ELEMENTS

CROSS-REFERENCE

This application is a continuation application of International Patent Application No. PCT/US2018/033515, filed May 18, 2018, which claims the benefit of U.S. Provisional Application No. 62/508,968, filed on May 19, 2017, each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on May 17, 2018, is named 46482-707_601_SL.txt and is 16,836 bytes in size.

BACKGROUND OF THE DISCLOSURE

Genetic engineering has enormous potential for treatment of disease, and production of proteins either for therapeutic or other uses. Instead of relying on drugs or surgery, patients, especially those with underlying genetic factors, can be treated by directly targeting the underlying cause. Furthermore, by targeting the underlying cause itself, gene therapy has the potential to effectively cure patients. Yet, despite this, clinical applications of gene therapy still require improvement in several aspects. One challenge is achieving high rates of expression of a transgene in one or more target tissues, or high efficiency of gene editing in one or more target tissues. Another challenge is introduced by the packaging limitations (or cloning capacities) of commonly used vectors. There is a need for short regulatory elements which can drive high expression of an operably linked transgene.

SUMMARY OF THE DISCLOSURE

Described herein are compositions and methods for driving high expression of a transgene. Also described herein are compositions and methods for driving high expression of a transgene comprising one or more human or human-derived regulatory elements (REs) which, when operably linked to a transgene, can facilitate or result in high (or increased) expression of the transgene in one or more target cell types or tissues. In some cases, high or increased transgene expression of any embodiment disclosed herein is determined as compared to a control, e.g., a constitutive promoter, CAG, CMV promoter, super core promoter (SCP), TTR promoter, Proto 1 promoter, UCL-HLP promoter, or CMVe promoter. Other controls that can be used for comparison to determine high or increased transgene expression by a regulatory element disclosed herein include buffer alone, min CMV, EFS, vector alone, or sequences that do not drive expression. In some embodiments, one or more regulatory elements disclosed herein drive high expression of a transgene in a cell or in vivo, in vitro, and/or ex vivo. In some embodiments, an expression cassette or vector comprising one or more regulatory elements described herein operably linked to a transgene can be adapted for use in any expression system or gene therapy to drive high expression of the transgene in a cell, a subject, or an animal model, or to result in a therapeutically effective level of transgene expression in a cell, a subject, or an animal model. In some embodiments, one or more REs of this disclosure are operably linked to a large transgene (e.g., a transgene whose sequence is more than 1 kb, 1.5 kb, 2 kb, 2.5 kb, 3 kb, 3.5 kb, 4 kb, 4.5 kb, 5 kb, 5.5 kb, 6 kb, 6.5 kb, 7 kb, or 7.5 kb) to result in high expression of the transgene in a cell or in vivo. In some cases, such high expression of the transgene in a cell or in vivo is relative to expression of the transgene without said REs, wherein expression of the transgene with the REs is at least 1.5 fold, at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 50 fold, at least 100 fold, or more than 100 fold as compared to transgene expression without the REs. In some cases, one or more REs result in such high transgene expression in at least 2, at least 3, at least 4, at least 5, at least 6, at least 7, at least 8, at least 9, or at least 10 different cell types. In some cases, one or more REs of this disclosure are operably linked to a transgene for a gene therapy treatment adapted for systemic administration. In some cases, one or more REs of this disclosure are operably linked to a transgene for a gene therapy treatment adapted for expression in the liver or hepatocytes. In some cases, the transgene is a DNA binding protein, e.g., a transcriptional modulator, which modulates an endogenous gene. In some cases, a RE of any embodiment disclosed herein comprises a promoter sequence, an intronic sequence, a 5' UTR sequence, or any combination thereof. In some cases, a RE of any embodiment disclosed herein is a human-derived sequence (or a sequence that has at least 80%, 90%, 95% or 99% sequence identity to a sequence in a human reference genome). In some cases, a RE of any embodiment disclosed herein is less than or equal to 300 bp, 250 bp, 200 bp, 150 bp, 140 bp, 130 bp, 120 bp, 110 bp, 100 bp, 70 bp, or 50 bp in length. In some cases, an expression construct (e.g., a vector, an AAV, or a viral vector) comprises one or more exogenous RE sequences operably linked to a transgene of this disclosure, wherein each exogenous RE sequence is selected from the sequences listed in TABLE 1 or SEQ ID NOs: 1-2, 13-17, and 22-41; or wherein each exogenous RE sequence comprises a sequence of TABLE 1 or SEQ ID NOs: 1-2, 13-17, and 22-41; or wherein each exogenous RE sequence comprises a sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity (e.g., local sequence identity) to a sequence of TABLE 1 or SEQ ID NOs: 1-2, 13-17, and 22-41 (e.g., sequence identity as measured by BLAST). In some cases, an expression cassette (e.g., a vector, an AAV, or a viral vector) comprises one or more RE sequences operably linked to any transgene, wherein each RE sequence is no more than 49 bp, 50 bp, 56 bp, 60 bp, 70 bp, 80 bp, 90 bp, 100 bp, 110 bp, 117 bp, 120 bp, 130 bp, 140 bp, 150 bp, 160 bp, 170 bp, 180 bp, 190 bp, 200 bp, 210 bp, 220 bp, 230 bp, 240 bp, 250 bp, 259 bp, 260 bp, 265 bp, 270 bp, 280 bp, 290 bp, 300 bp, 310 bp, 320 bp, 330 bp, 340 bp, 350 bp, 360 bp, 370 bp, 380 bp, 390 bp, or 400 bp, and comprises a sequence according to any one of TABLE 1 or SEQ ID NOs: 1-2, 13-17, and 22-41. In some cases, an expression construct (e.g., a vector, an AAV, or a viral vector) comprises one or more exogenous RE sequences operably linked to a transgene of this disclosure, wherein each RE sequence is no more than 49 bp, 50 bp, 56 bp, 60 bp, 70 bp, 80 bp, 90 bp, 100 bp, 110 bp, 117 bp, 120 bp, 130 bp, 140 bp, 150 bp, 160 bp, 170 bp, 180 bp, 190 bp, 200 bp, 210 bp, 220 bp, 230 bp, 240 bp, 250 bp, 259 bp, 260 bp, 265 bp, 270 bp, 280 bp, 290 bp, 300 bp, 310 bp, 320 bp, 330 bp, 340 bp, 350 bp, 360 bp, 370 bp, 380 bp, 390 bp, or 400 bp, and comprises a sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of TABLE 1 or SEQ ID NOs: 1-2, 13-17, and 22-41. In some cases, local sequence identity is measured using BLAST. In some cases, percent sequence identity refers to global sequence identity, covering the entire exogenous RE in an expression cassette. In other cases, percent sequence identity refers to local sequence identity, covering a region or part of a region that corresponds to any one of the sequences listed in TABLE 1. In some cases, percent sequence identity refers to local sequence identity, covering a region that comprises no more than 49 bp, 50 bp, 56 bp, 60 bp, 70 bp, 80 bp, 90 bp, 100 bp, 110 bp, 117 bp, 120 bp, 130 bp, 140 bp, 150 bp, 160 bp, 170 bp, 180 bp, 190 bp, 200 bp, 210 bp, 220 bp, 230 bp, 240 bp, 250 bp, 259 bp, 260 bp, 265 bp, 270 bp, 280 bp, 290 bp, 300 bp, 310 bp, 320 bp, 330 bp, 340 bp, 350 bp, 360 bp, 370 bp, 380 bp, 390 bp, or 400 bp of an expression cassette, not including the transgene. As used herein, "relatively short" when describing a RE of the disclosure is preferably a RE sequence that is no more than 45 bp, 49 bp, 50 bp, 56 bp, 60 bp, 70 bp, 80 bp, 90 bp, 100 bp, 110 bp, 117 bp, 120 bp, 130 bp, 140 bp, 150 bp, 160 bp, 170 bp, 180 bp, 190 bp, 200 bp, 210 bp, 220 bp, 230 bp, 240 bp, 250 bp, 259 bp, 260 bp, 265 bp, 270 bp, 280 bp, 290 bp, 300 bp, 310 bp, 320 bp, 330 bp, 340 bp, 350 bp, 360 bp, 370 bp, 380 bp, 390 bp, or 400 bp. Examples of a relatively short RE include the sequences listed in TABLE 1, or SEQ ID NOs: 1-2, 13-17, and 22-41; or sequences having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity thereto and are also no more than 45 bp, 49 bp, 50 bp, 56 bp, 60 bp, 70 bp, 80 bp, 90 bp, 100 bp, 110 bp, 117 bp, 120 bp, 130 bp, 140 bp, 150 bp, 160 bp, 170 bp, 180 bp, 190 bp, 200 bp, 210 bp, 220 bp, 230 bp, 240 bp, 250 bp, 259 bp, 260 bp, 265 bp, 270 bp, 280 bp, 290 bp, 300 bp, 310 bp, 320 bp, 330 bp, 340 bp, 350 bp, 360 bp, 370 bp, 380 bp, 390 bp, or 400 bp.

In some cases, a RE sequence of any embodiment disclosed herein is located upstream or downstream of a transgene. In some cases, two or more REs of any embodiment disclosed herein are operably linked to a transgene, wherein at least one or more of the REs are located upstream or downstream of the transgene. In some cases, one or more REs of any embodiment of this disclosure are operably linked to a transgene to drive global expression of the transgene, wherein global expression refers to expression in at least 2, 3, 4, 5, 6, 7, 8, 9, or 10 different cell types. In some cases, one or more REs of any embodiment of this disclosure are operably linked to a transgene to drive global expression of the transgene, wherein the construct comprising the REs and the transgene can be delivered systemically, e.g., via oral, intravenous, intramuscular, intraperitoneal, intrathecal, enteral, or parenteral administration. In various embodiments, a RE disclosed herein is human-derived (or a sequence that has at least 80%, 90%, 95% or 99% sequence identity to a sequence in a human reference genome). In some cases, a RE of any embodiment disclosed herein is non-naturally occurring.

In some instances, an expression vector comprises a human-derived regulatory element having less than or equal to 400 bp, 300 bp, 250 bp, 200 bp, 150 bp, 140 bp, 130 bp, 120 bp, 110 bp, 100 bp, 70 bp, or 50 bp operably linked to a transgene, wherein the regulatory element increases global expression (e.g., expression in at least 2, 3, 4, 5, 6 or more different cell types) of the transgene by at least two fold as compared to a second expression vector without the regulatory element. In some cases, the second expression vector comprises the transgene operably linked to a control promoter, such as a CMV promoter.

In some cases, a RE of this disclosure comprises a human-derived intronic sequence, e.g., SEQ ID NOs: 1-2. In some cases, an expression cassette of this disclosure comprises one or more of SEQ ID NOs: 1-2 operably linked to a transgene. In some cases, a RE comprising any one or more of SEQ ID NOs: 1-2 is located upstream, downstream, or both upstream and downstream of the transgene.

In some cases, a RE of this disclosure comprises a human-derived promoter sequence, e.g., SEQ ID NOs: 13-17 and 22-41. In some cases, an expression cassette of this disclosure comprises one or more of SEQ ID NOs: 13-17 and 22-41 operably linked to a transgene. In some cases, a RE comprising any one or more of SEQ ID NOs: 13-17 and 22-41 is located upstream, downstream, or both upstream and downstream of the transgene.

In some cases, a RE of this disclosure comprises a human-derived intronic sequence and/or a promoter sequence, e.g., two or more of SEQ ID NOs: 1-2, 13-17 and 22-41; or two or more of the sequences listed at TABLE 1. In some cases, an expression cassette of this disclosure comprises one or more, two or more, three or more, four or more, or five or more of sequences listed at TABLE 1 operably linked to a transgene. In some cases, one or more REs listed at TABLE 1 are located upstream, downstream, or both upstream and downstream of the transgene in an expression cassette. In some cases, one or more REs listed at TABLE 1 are located upstream of the transgene in an expression cassette disclosed herein.

In some instances, a RE of any embodiment disclosed herein consists of a sequence selected from TABLE 1 or SEQ ID NOs: 1-2, 13-17, and 22-41, and any combination thereof. In some cases, two or more REs listed in TABLE 1 are combined without a linker sequence. In some cases, two or more REs listed in TABLE 1 are combined using a linker sequence of 1-50 bp. In some cases, two or more REs listed in TABLE 1 are placed in an expression construct such that the 5' start of the RE sequences are less than 2 bp, 5 bp, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1 kb, 1.5 kb, 2 kb, 2.5 kb, 3 kb, 3.5 kb, 4 kb, 4.5 kb, 5 kb, 5.5 kb, 6 kb, 6.5 kb, 7 kb, or 7.5 kb apart.

In some instances, an expression vector comprises a human-derived regulatory element having less than or equal to 300 bp, 250 bp, 200 bp, 150 bp, 140 bp, 130 bp, 120 bp, 110 bp, 100 bp, 70 bp, or 50 bp operably linked to a transgene, whereby expression of the transgene is higher than that of the same transgene expressed by a control regulatory element, such as a constitutive promoter, CMV promoter, super core promoter, TTR promoter, Proto 1 promoter, UCL-HLP promoter, or CMVe promoter. In some cases, expression of the transgene operably linked to the RE is higher than that of the same transgene linked to a UCL-HLP promoter without the RE.

In some cases, an expression vector comprises a human-derived regulatory element operably linked to a transgene, wherein a protein encoded by the transgene has (i) a concentration >1.0 IU/mL, >1.5 IU/mL, >2.0 IU/mL, >2.5 IU/mL, or >3.0 IU/mL as measured by an ELISA assay configured to detect the transgene; and/or (ii) >20%, >25%, >30%, >35%, >40%, >45%, >50%, >55%, >60%, >65%, >70%, >75%, >80%, >85%, >90%, or >95%, activity as measured by a Coatest assay. In some cases, such activity or transgene expression is assayed in an animal model, such as a mouse. In some cases, the transgene expression or activity described herein is normalized to a dose of expression cassette, vector, virus, or DNA delivered to cells or a mouse, such as a dose of 16 µg (or 10-20 µg) of an expression vector per mouse.

In some cases, a vector comprises a human-derived regulatory element having a sequence less than or equal to 300 bp, 250 bp, 200 bp, 150 bp, 140 bp, 130 bp, 120 bp, 110 bp, 100 bp, 70 bp, or 50 bp in size operably linked to a transgene that is not found in the context with the regulatory element in a cell or in vivo, or is not normally linked to the regulatory element.

In some cases, the expression cassette or vector described herein comprises a regulatory element that is an intronic sequence, a promoter sequence, an enhancer sequence, or a combination thereof. In some cases, the expression cassette or vector comprises a regulatory element that is SEQ ID NO: 1, 2, 3, 4, 13, 14, 15, 16, 17, 22, 23, 24, 25, 26, 27, 28, 29, 30, 31, 32, 33, 34, 35, 36, 37, 38, 39, 40, or 41, or a combination thereof, or a sequence having at least 80%, at least 85%, at least 90%, at least 91%, at least 92%, at least 93%, at least 94%, at least 95%, at least 96%, at least 97%, at least 98%, or at least 99% sequence identity thereto. In some cases, the expression cassette or vector comprises a transgene that is a reporter gene, e.g., luciferase. In some cases, the use of a reporter gene, e.g., luciferase, as the transgene results in global expression that is greater than $1 \times 10^8$ photons/sec as measured in whole mice, or results in increased transgene expression in at least 2, 3, 4, 5, 6, 7, 8, 9, 10, or more cell types in an animal, e.g., a mouse. In some cases, the activity or transgene expression of an expression cassette or vector described herein is normalized to a dose of expression cassette, vector, virus, or DNA delivered to a mouse, such as a dose of 12 µg or a dose of 10-20 µg of expression vector per mouse. In some cases, the endogenous version of the transgene disclosed herein is not linked to the regulatory element in a cell or in vivo, or is not normally linked to or associated with the regulatory element in a cell or in vivo. In some cases, global expression of the transgene is at a level greater than expression of the transgene using a vector with a regulatory element selected from the group consisting of: a CMV promoter, a CMVe promoter, a super core promoter, TTR promoter, Proto 1 promoter, and a UCL-HLP promoter. In some cases, expression is detectable in at least 2, 3, 4, 5, 6, 7 or more different cell types in vivo (e.g., in a mouse or in different human cell lines). In some cases, the different cell types are selected from the group consisting of: alveolar cells, cardiomyocytes, epithelial cells, hepatocytes, intestinal cells, myocytes, neurons, and renal cells. In some cases, a regulatory element as disclosed herein is or comprises an enhancer, a promoter, a 5' UTR sequence, an intronic sequence, or any combination thereof. In some cases, a regulatory element as disclosed herein is or comprises a promoter sequence. In some cases, a regulatory element comprises a promoter that is a CMV promoter, CMV, promoter, super core promoter, TTR promoter, Proto 1 promoter, UCL-HLP promoter, an AAT promoter, a KAR promoter, a EF1α promoter, EFS promoter, or CMVe enhancer/CMV promoter combination, or any combination, variant, or fragment thereof.

In some cases, an expression vector or cassette disclosed herein further comprises one or more post-transcriptional modification sites. In some cases, the expression vector or cassette comprises a transgene that is Cas9, saCas9, or dCas9. In some cases, the expression vector or cassette comprises a transgene that is a DNA binding protein or a transcriptional modulator, e.g., a transcriptional activator. In some cases, such transcriptional modulator protein acts on an endogenous gene to increase expression of the endogenous gene in a cell or in vivo.

In other instances, an expression vector comprises a Factor VIII transgene operably linked to a regulatory sequence disclosed herein that is able to drive expression of the Factor VIII to a concentration >1.0 IU/mL as measured by an ELISA assay configured to detect Factor VIII in vivo.

In some cases, the transgene in any embodiment disclosed herein is a gene associated with a haploinsufficiency. In some cases, such haploinsufficiency is in the liver or hepatocytes. In some cases, the transgene is any one of Factor VIII, Cas9, a hormone, a growth or differentiation factor, insulin, growth hormone, VEGF, neurotrophic factor, fibroblast epithelial factor; cytokine, interleukin, lymphokine, tumor necrosis factor, antibody, immunoglobulin, interferon, chimeric T cell receptor; lipoprotein receptor, cystic fibrosis transmembrane regulator, a gene associated with mucopolysaccharidosis type I, II, III, or IV, beta globin or lipoprotein lipase, or a variant, subunit, or functional fragment thereof. In some cases, the therapeutic transgene is ATP7A, ATP7B, ATP8B1, ABCB4, ABCB11, or a variant, subunit, or functional fragment thereof. In some cases, the therapeutic transgene is CDKL5, CNTNAP2, ZEB2, or a variant or functional fragment thereof. In some cases, the transgene is a fibrinogen, prothrombin, a coagulation factor, or a blood clotting factor (e.g., Factor 1, 2, 3, 4, 5, 6, 7, 8, 9, 10, 11, or 12), or a variant or functional fragment thereof.

In some cases, any one of the expression vectors or cassettes as described herein is a viral particle, or is delivered using a viral particle, or is encapsidated or provided in a viral particle. In some cases, the viral particle is an adeno-associated virus, or an AAV. In some cases, the AAV is selected from the group consisting of: AAV1, AAV2, AAV3, AAV3b, AAV4, AAV5, AAV6, AAV7, AAV8, AAV9, AAV10, AAV11, AAV12, AAV-DJ, and scAAV. In other cases, the viral particle is a lentivirus. In some cases, the viral particle is an adenovirus.

In some instances, any one of the expression vectors or cassettes disclosed herein comprises a transgene that is a therapeutic transgene. In some cases, the therapeutic transgene is Factor VIII, Cas9, a DNA binding protein, hormone, growth or differentiation factor, insulin, growth hormone, VEGF, neurotrophic factor, fibroblast epithelial factor; cytokine, interleukin, lymphokine, tumor necrosis factor, antibody, immunoglobulin, interferon, chimeric T cell receptor; lipoprotein receptor, cystic fibrosis transmembrane regulator, a gene associated with mucopolysaccharidosis type I, II, III, or IV, beta globin or lipoprotein lipase, or a variant or functional fragment thereof. In some cases, the therapeutic transgene is ATP7A, ATP7B, ATP8B1, ABCB4, ABCB11, or a variant, subunit, or functional fragment thereof. In some cases, the transgene is any one of ATP7A, ATP7B, AT8B1 (or ATP8B1), MDR3 (or ABCB4), ABCBB (or ABCB11), CDKL5, CNTP2 (or CNTNAP2), ZEB2, Factor V, Factor VIII, Factor IX, or Factor X, or a variant, subunit, or functional fragment thereof. In some cases, the therapeutic transgene is CDKL5, CNTNAP2, ZEB2, or a variant, subunit, or functional fragment thereof. In some cases, the transgene is a fibrinogen, prothrombin, a coagulation factor, or a blood clotting factor (e.g., Factor 1, 2, 3, 4, 5, 6, 7, 8, 9, 10, 11, or 12), or a variant or functional fragment thereof.

In some instances, a method for delivering a transgene to a plurality of different tissues or cell types in an animal (e.g., a mammal, a human, a mouse, etc.) comprises administering to said animal any one of the expression vectors disclosed herein. In some cases, the administering comprises a systemic administration, e.g., via oral, intravenous, intramuscular, intraperitoneal, intrathecal, enteral, or parenteral administration.

In some instances, a method for production of proteins, antibodies, or other biologics, comprises contacting a cell with any one of the expression vectors disclosed herein. In some cases, the cell used for production of proteins is a CHO cell or a HEK293T cell. In some cases, an expression construct of any embodiment disclosed herein is used for a gene therapy treatment, e.g., expression in hepatocytes, kidney cells, and/or neurons (or in the central nervous system (CNS)). In other cases, an expression construct of any embodiment disclosed herein is used to produce a protein ex vivo, e.g., in any mammalian or any human cell line, such as kidney cells, epithelial cells, liver cells, hepatocytes, neurons, fibroblasts, or CNS cells.

In some instances, a method for producing a transgenic animal or plant comprises administering to an animal or plant any one of the expression vectors or cassettes disclosed herein. In some cases, the regulatory element used in any one of the expression vectors or cassettes disclosed herein is relatively short, or 40-50 bp, 50-60 bp, 60-70 bp, 70-80 bp, 80-90 bp, 90-100 bp, 100-110 bp, 110-120 bp, or 120-130 bp. In some cases, a RE in an expression cassette disclosed herein is 49 bp, 56 bp, 100 bp, 117 bp, 259 bp, or 266 bp. In some cases, the regulatory element used in any one of the expression vectors or cassettes disclosed herein is 45-50 bp, 50-60 bp, 45-60 bp, 90-117 bp, 95-110 bp, 115-120 bp, 250-260 bp, or 260-270 bp. In some cases, the regulatory element used in any one of the expression vectors or cassettes disclosed herein is about 100 bp. In some cases, the regulatory element used in any one of the expression vectors or cassettes disclosed herein is less than or equal to 300 bp, 250 bp, 200 bp, 150 bp, 140 bp, 130 bp, 120 bp, 110 bp, 100 bp, 70 bp, or 50 bp. In some cases, the regulatory element used in any one of the expression vectors or cassettes disclosed herein is 100 bp or smaller. In some cases, two or more relatively short REs disclosed herein are combined and are operably linked to a transgene to drive high expression of the transgene. In some cases, two or more REs can be combined without any intervening nucleotides, or are combined using a linker of 1-50 bp.

In some aspects, an expression cassette disclosed herein comprises a human-derived regulatory element operably linked to a therapeutic transgene, wherein the regulatory element comprises one or more of (i) SEQ ID NOs: 1-2, 13-17, and 22-41; (ii) a fragment or a combination thereof; or (iii) sequences having at least 80% sequence identity to any one of (i) and (ii). In some cases, the regulatory element is derived from human sequences of hg19. In some cases, the regulatory element is non-naturally occurring. In some cases, the regulatory element comprises an intronic sequence. In some cases, intronic sequence is located between a promoter and the therapeutic transgene. In some cases, the regulatory element comprises a promoter sequence. In some cases, the regulatory element is the only promoter in the cassette. In some cases, the regulatory element is no more than 100 bp. In some cases, the regulatory element is no more than 60 bp. In some cases, the regulatory element is no more than 50 bp. In some cases, the expression cassette is part of a rAAV. In some cases, the rAAV is rAAV8. In some cases, the therapeutic transgene is ATP7B. In some cases, the therapeutic transgene is Factor VIII. In some aspects, a method of treating Wilson's disease comprises administering an expression cassette disclosed herein and wherein the transgene is ATP7B. In some cases, a method of treating a haploinsufficiency or a genetic defect in ATP7B comprises administering an expression cassette disclosed herein and wherein the transgene is ATP7B. In some cases, a method of treating a blood clotting disorder comprises administering an expression cassette disclosed herein and wherein the transgene is Factor VIII. In some cases, a method of treating a haploinsufficiency or a genetic defect comprises administering an expression cassette disclosed herein and wherein the transgene is selected from: ATP7A; ATP7B; ATP8B1; ABCB4; ABCB11; CDKL5; CNTNAP2; ZEB2; Factor 1, 2, 3, 4, 5, 6, 7, 8, 9, 10, 11, and 12; and a variant or a functional fragment thereof. In some cases, a method of treating a haploinsufficiency or a genetic defect comprises administering an expression cassette disclosed herein and wherein the transgene is a transcriptional modulator that modulates expression of an endogenous gene. In some cases, a method of treating a haploinsufficiency or a genetic defect comprises administering the expression cassette disclosed herein and wherein the transgene is a transcriptional activator of any one of the following endogenous genes: ATP7A; ATP7B; ATP8B1; ABCB4; ABCB11; CDKL5; CNTNAP2; ZEB2; and Factor 1, 2, 3, 4, 5, 6, 7, 8, 9, 10, 11, and 12.

In some aspects, an AAV expression cassette comprises a human-derived regulatory element of no more than 120 bp operably linked to a transgene of at least 3 kb, wherein the regulatory element results in increased transgene expression by at least 2 fold as compared to expression of the transgene when operably linked to a CMV promoter. In some cases, the regulatory element is selected from: SEQ ID NO: 1-2, 13-17, and 22-41. In some cases, the regulatory element comprises (i) SEQ ID NO: 1-2, 13-17, and 22-41; (ii) a combination thereof; or (iii) or sequence having at least 80% sequence identity to any one of (i) and (ii). In some cases, the increased transgene expression is at least 50 fold. In some cases, the increased transgene expression is at least 100 fold. In some cases, the increased transgene expression occurs in at least 2 different cell types (e.g., hepatocytes and kidney cells). In some cases, the increased transgene expression occurs in at least 3 different cell types (e.g., hepatocytes, kidney cells, neurons, and/or epithelial cells). In some cases, the regulatory element comprises any one or more of SEQ ID NOs: 22-41, and wherein no other promoter sequences are present in the expression cassette. In some cases, the regulatory element is located upstream of the transgene. In some cases, the regulatory element comprises one or more of SEQ ID NO: 1 and SEQ ID NO: 2. In some cases, the regulatory element is located downstream of a promoter. In some cases, the transgene is selected from: ATP7A; ATP7B; ATP8B1; ABCB4; ABCB11; CDKL5; CNTNAP2; ZEB2; Factor 1, 2, 3, 4, 5, 6, 7, 8, 9, 10, 11, and 12; and a variant or a functional fragment thereof. In some cases, the transgene is ATP7A or ATP7B, or a variant or a functional fragment thereof. In some cases, the transgene is any one of Factor 1, 2, 3, 4, 5, 6, 7, 8, 9, 10, 11, and 12, or a variant or a functional fragment thereof. In some cases, the transgene is Factor 8, or a variant or a functional fragment thereof. In some cases, the transgene is a gene editing protein. In some cases, the gene editing protein is Cas (e.g., Cas9). In some cases, the transgene is a DNA binding protein. In some cases, the transgene is a transcriptional activator that increases expression of an endogenous gene. In some cases, the transgene is a transcriptional repressor that decreases expression of an endogenous gene. In some cases, the transcriptional activator increases expression of any one of the following endogenous genes: ATP7A; ATP7B; ATP8B1; ABCB4; ABCB11; CDKL5; CNTNAP2; ZEB2; and Factor 1, 2, 3, 4, 5, 6, 7, 8, 9, 10, 11, and 12. In some cases, the AAV is selected from the group consisting of: AAV1, AAV2, AAV3, AAV3b, AAV4, AAV5, AAV6, AAV7, AAV8, AAV9, AAV10, AAV11, AAV12, AAV-DJ, and scAAV.

In some aspects, a method of producing a recombinant protein comprises operably linking a sequence encoding the protein with one or more of (i) SEQ ID NO: 1-2, 13-17, and 22-41; (ii) a combination thereof or (iii) sequences having at least 80% sequence identity to any one of (i) and (ii).

In some aspects, a method of treating a liver disease or condition comprises administering a gene therapy comprising a therapeutic transgene operably linked to one or more regulatory elements selected from (i) SEQ ID NO: 1-2, 13-17, and 22-41; (ii) a combination thereof; or (iii) sequences having at least 80% sequence identity to any one of (i) and (ii). In some cases, the liver disease or condition is Wilson's disease. In some cases, the liver disease or condition is a blood clotting disorder. In some cases, the transgene is ATP7A or ATP7B, or a variant or a functional fragment thereof. In some cases, the transgene is Factor 1, 2, 3, 4, 5, 6, 7, 8, 9, 10, 11, 12, or a variant or a functional fragment thereof. In some cases, the transgene is Factor 8, or a variant or a functional fragment thereof. In some cases, the regulatory elements result in increased transgene expression in at least 2 cell types. In some cases, the regulatory elements result in increased transgene expression in at least 3 cell types. In some cases, the regulatory elements result in increased transgene expression in hepatocytes. In some cases, the regulatory elements result in increased transgene expression at a level that is at least 2 fold as compared to expression of the transgene when operably linked to a CMV promoter. In some cases, the gene therapy is AAV. In some cases, the AAV is AAV8.

In some aspects, an expression vector comprises a human-derived regulatory element having less than or equal to 100 bp operably linked to a transgene, wherein the regulatory element increases global expression of the transgene by at least two fold as compared to a second expression vector without the regulatory element. In some cases, the second expression vector comprises the transgene operably linked to a CMV promoter.

In some aspects, an expression vector comprises a human-derived regulatory element having less than or equal to 100 bp operably linked to a transgene, whereby expression of the transgene is higher than that of the same transgene expressed by a CMV promoter, super core promoter, TTR promoter, Proto 1 promoter, UCL-HLP promoter, or CMVe promoter. In some cases, the expression of the transgene is higher than that of the same transgene expressed by a UCL-HLP promoter. In some aspects, an expression vector comprises a human-derived regulatory element operably linked to a transgene, wherein a protein encoded by the transgene has (i) a concentration >1.0 IU/mL as measured by an ELISA assay configured to detect the transgene; and/or (ii) >25% activity as measured by a Coatest assay. In some aspects, a vector disclosed herein comprises a human-derived regulatory element having a sequence less than or equal to 100 bp in size operably linked to a transgene not found in context with the regulatory element in a cell or in vivo. In some cases, a vector disclosed herein comprises a regulatory element that is an intronic sequence. In some cases, the regulatory element is SEQ ID NO: 1 or SEQ ID NO: 2, or a sequence having at least 80% homology thereto. In some cases, use of a luciferase as the transgene results in global expression that is greater than $1\times10^8$ photons/sec as measured in whole mice. In some cases, the activity or transgene expression corresponds to a dose of 16 µg of expression vector per mouse. In some cases, the activity or transgene expression corresponds to a dose of 12 µg of expression vector per mouse. In some cases, the endogenous version of the transgene is not linked to the regulatory element in vivo. In some cases, the global expression of the transgene is at a level greater than expression of the transgene using a vector with a regulatory element selected from the group consisting of: a CMV promoter, a CMVe promoter, a super core promoter, TTR promoter, Proto 1 promoter, and a UCL-HLP promoter. In some cases, expression is detectable in at least 2, 3, 4, 5, 6, or 7 different cell types in a mouse, in vivo, or in cell lines. In some cases, the different cell types are selected from the group consisting of: alveolar cells, cardiomyocytes, epithelial cells, hepatocytes, intestinal cells, myocytes, neurons, and renal cells. In some cases, the regulatory element is an enhancer. In some cases, a vector disclosed herein further comprises a promoter. In some cases, the promoter is a CMV promoter, CMV, promoter, super core promoter, TTR promoter, Proto 1 promoter, UCL-HLP promoter, an AAT promoter, a KAR promoter, a EF1α promoter, EFS promoter, or CMVe enhancer/CMV promoter combination. In some cases, a vector disclosed herein further comprises one or more post-transcriptional modification sites. In some cases, the transgene is Cas9. In some cases, the transgene is saCas9.

In some aspects, an expression vector comprises a Factor VIII transgene operably linked to a regulatory sequence that is able to drive expression of the Factor VIII to a concentration >1.0 IU/mL as measured by an ELISA assay configured to detect Factor VIII in vivo. In some cases, a viral particle comprises an expression vector disclosed herein. In some cases, the viral particle is an AAV. In some cases, the AAV is selected from the group consisting of: AAV1, AAV2, AAV3, AAV3b, AAV4, AAV5, AAV6, AAV7, AAV8, AAV9, AAV10, AAV11, AAV12, AAV-DJ, and scAAV. In some cases, the viral particle is a lentivirus. In some cases, the virus particle is an adenovirus. In some cases, the transgene is a therapeutic transgene. In some cases, the therapeutic transgene is Factor VIII, Cas9, a DNA binding protein, hormone, growth or differentiation factor, insulin, growth hormone, VEGF, neurotrophic factor, fibroblast epithelial factor; cytokine, interleukin, lymphokine, tumor necrosis factor, antibody, immunoglobulin, interferon, chimeric T cell receptor; lipoprotein receptor, cystic fibrosis transmembrane regulator, a gene associated with mucopolysaccharidosis type I, II, III, or IV, beta globin, or lipoprotein lipase. In some cases, the therapeutic transgene is ATP7A, ATP7B, ATP8B1, ABCB4, ABCB11, or a variant or functional fragment thereof. In some cases, the therapeutic transgene is CDKL5, CNTNAP2, ZEB2, or a variant or functional fragment thereof. In some cases, a method for delivering a transgene to a plurality of different tissues or cell types in an animal comprises administering to said animal an expression vector disclosed herein. In some cases, a method for production of proteins comprises transfecting a cell with an expression vector disclosed herein. In some cases, the cell is a CHO cell or a HEK293T cell. In some cases, a method for producing a transgenic animal or plant comprises administering to an animal or plant an expression vector of any embodiment disclosed herein. In some cases, the regulatory element is 40-50 bp. In some cases, the regulatory element is 50-60 bp.

In some aspects, an expression vector comprises a human-derived regulatory element operably linked to a transgene, wherein a protein encoded by the transgene has (i) a concentration >0.1 IU/mL as measured by an ELISA assay configured to detect the transgene; and/or (ii) >10% activity as measured by a Coatest assay. In other aspects, an expression vector comprises a human-derived regulatory element having <120 bp operably linked to a transgene, whereby expression of the transgene is higher than that of the same transgene expressed by a UCL-HLP promoter. In some cases, the regulatory element is a promoter. In some cases, the therapeutic transgene is a fusion protein comprising a DNA binding domain and a transcription regulatory domain.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE DISCLOSURE

Figure 1A:
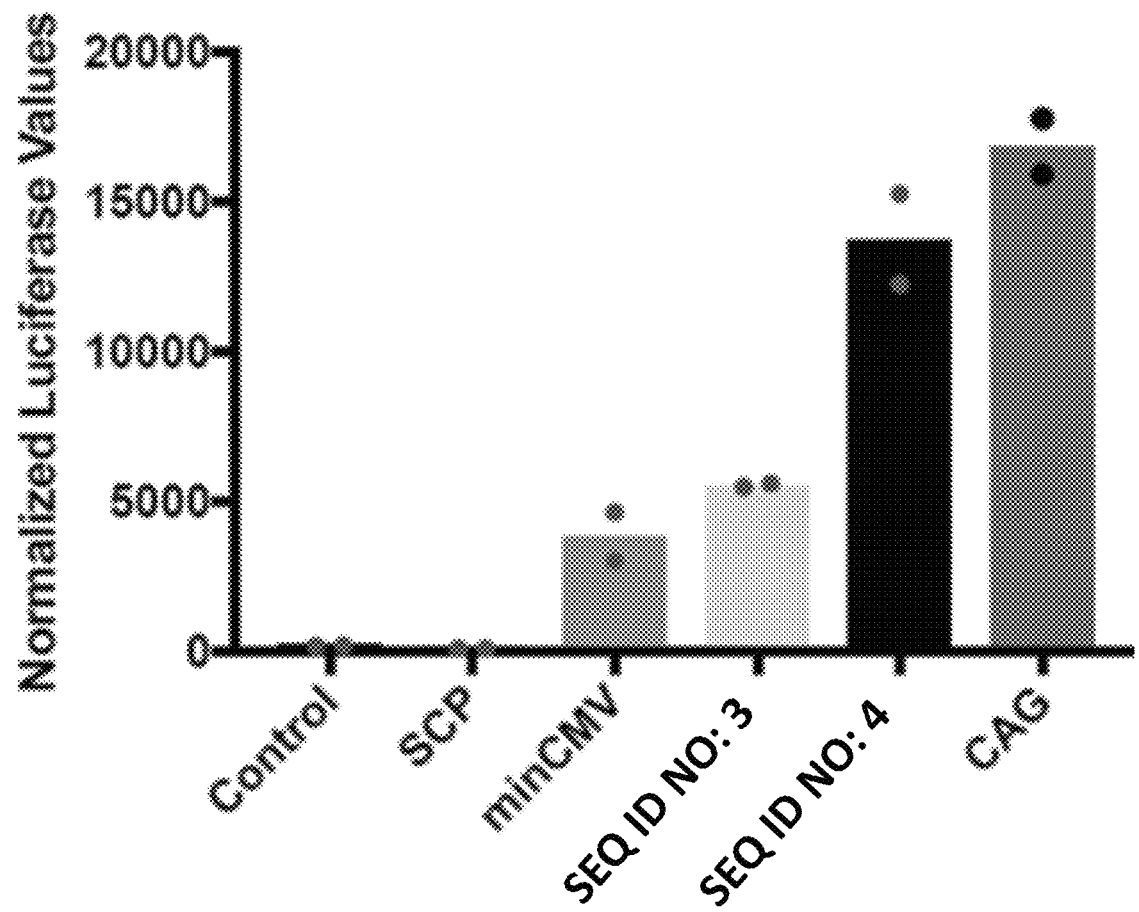
FIG. 1A illustrates the normalized luciferase values of plasmids comprising different regulatory elements (e.g., SEQ ID NO: 1 and SEQ ID NO: 2), demonstrating the effect the REs had on expression of luciferase in HEK293T cells. For example, SEQ ID NO: 3 (comprising SEQ ID NO: 1 combined with a minimal CMV (min CMV) promoter) drove expression of luciferase at a level about 1.4 fold higher than the expression driven by the min CMV promoter alone, and about 60 fold higher than the expression driven by a SCP promoter.

The present disclosure contemplates compositions and methods for high expression of a transgene. Also described herein are compositions and methods for high expression of a transgene comprising one or more human or human-derived regulatory elements (REs) which, when operably linked to a transgene, can facilitate or result in high (or increased) expression of the transgene in one or more target cell types or tissues. In some embodiments, one or more regulatory elements disclosed herein drive high expression of a transgene in a cell or in vivo, in vitro, and/or ex vivo. In some embodiments, an expression cassette or vector comprising one or more regulatory elements described herein operably linked to a transgene can be adapted for use in any expression system or gene therapy to drive high expression of the transgene in a cell, a subject, or an animal model, or to result in a therapeutically effective level of transgene expression in a cell, a subject, or an animal model. In some embodiments, one or more REs of this disclosure is operably linked to a large transgene (e.g., a transgene whose sequence is more than 1 kb, 1.5 kb, 2 kb, 2.5 kb, 3 kb, 3.5 kb, 4 kb, 4.5 kb, 5 kb, 5.5 kb, 6 kb, 6.5 kb, 7 kb, or 7.5 kb) to result in high expression of the transgene in a cell or in vivo. In some cases, such high expression of the transgene in a cell or in vivo is relative to expression of the transgene without said REs, wherein expression of the transgene with the REs is at least 1.5 fold, at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 50 fold, at least 100 fold, at least 150 fold, at least 200 fold, at least 250 fold, at least 300 fold, at least 400 fold, at least 500 fold, at least 600 fold, at least 700 fold, at least 800 fold, at least 900 fold, at least 1000 fold, at least 1010 fold, at least 1020 fold, at least 1030 fold, at least 1040 fold, or at least 1050 fold as compared to transgene expression without the REs, or as compared to transgene expression by a negative control (e.g., buffer alone, vector alone, or a vector comprising a sequence known to have no expression activity).

In some cases, one or more REs result in high transgene expression in at least 2, at least 3, at least 4, at least 5, at least 6, at least 7, at least 8, at least 9, or at least 10 different cell types. In some cases, one or more REs of this disclosure are operably linked to a transgene for a gene therapy treatment adapted for systemic administration. In some cases, one or more REs of this disclosure are operably linked to a transgene for a gene therapy treatment adapted for expression in the liver or hepatocytes. In some cases, the transgene is a gene that is expressed in the liver or in hepatocytes, or is a gene relevant in a liver disease or condition, e.g., ATP7B associated with Wilson's disease; ABCB4 associated with progressive familial intrahepatic cholestasis type 3; ALDOB associated with hereditary fructose intolerance; GBE1 associated with glycogen storage disease type IV; FAH associated with tyrosinemia type I; ASL associated with argininosuccinate lyase deficiency; SLC25A13 associated with citrin deficiency (CTLN2, NICCD); LIPA associated with cholesteryl ester storage disease; SERPINA1 associated with alpha-1 antitrypsin deficiency; CFTR associated with cystic fibrosis; HFE associated with hereditary hemochromatosis; or ALMS1 associated with Alström syndrome. In some cases, one or more regulatory elements disclosed herein are used for a gene therapy treatment to treat an inherited liver disease, e.g., a disorder of bile acid synthesis, a disorder of carbohydrate metabolism, a disorder of amino acid metabolism, a urea cycle disorder, or a disorder of lipid metabolism. In some cases, the transgene is a DNA binding protein, e.g., a transcriptional modulator, which modulates an endogenous gene. In some cases, a RE of any embodiment disclosed herein comprises a promoter sequence, an intronic sequence, a 5' UTR sequence, or any combination thereof. In some cases, a RE of any embodiment disclosed herein is a human-derived sequence (or a sequence that has at least 80%, 90%, 95% or 99% sequence identity to a sequence in a human reference genome). In some cases, a RE of any embodiment disclosed herein is less than or equal to 50 bp, 60 bp, 100 bp, 120 bp, 260 bp, or 270 bp in length. In some cases, a RE of any embodiment disclosed herein is less than or equal to 300 bp, 250 bp, 200 bp, 150 bp, 140 bp, 130 bp, 120 bp, 110 bp, 100 bp, 70 bp, or 50 bp. In some cases, an expression cassette (e.g., a vector, an AAV, or a viral vector) comprises one or more RE sequences operably linked to a transgene of this disclosure, wherein each RE sequence is any one of the sequences listed at TABLE 1, or a sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity (e.g., local sequence identity) to a sequence of TABLE 1. In some cases, an expression construct (e.g., a vector, an AAV, or a viral vector) comprises one or more RE sequences operably linked to a transgene of this disclosure, wherein each RE sequence is no more than 50 bp, 60 bp, 70 bp, 80 bp, 90 bp, 100 bp, 110 bp, 120 bp, 130 bp, 140 bp, 150 bp, 160 bp, 170 bp, 180 bp, 190 bp, 200 bp, 210 bp, 220 bp, 230 bp, 240 bp, 250 bp, 260 bp, 270 bp, 280 bp, 290 bp, 300 bp, 310 bp, 320 bp, 330 bp, 340 bp, 350 bp, 360 bp, 370 bp, 380 bp, 390 bp, or 400 bp, and comprises a sequence according to any one or more of the sequences of TABLE 1. In some cases, an expression cassette (e.g., a vector, an AAV, or a viral vector) comprises one or more RE sequences operably linked to a transgene of this disclosure, wherein each RE sequence is no more than 50 bp, 60 bp, 70 bp, 80 bp, 90 bp, 100 bp, 110 bp, 120 bp, 130 bp, 140 bp, 150 bp, 160 bp, 170 bp, 180 bp, 190 bp, 200 bp, 210 bp, 220 bp, 230 bp, 240 bp, 250 bp, 260 bp, 270 bp, 280 bp, 290 bp, 300 bp, 310 bp, 320 bp, 330 bp, 340 bp, 350 bp, 360 bp, 370 bp, 380 bp, 390 bp, or 400 bp, and comprises a sequence having at least 70%, at least 75%, at least 80%, at least 85%, at least 90%, at least 91%, at least 92%, at least 93%, at least 94%, at least 95%, at least 96%, at least 97%, at least 98%, or at least 99% local sequence identity to any one of the sequences listed at TABLE 1. In some cases, local sequence identity is measured using BLAST. In some cases, a RE sequence of any embodiment disclosed herein is located upstream or downstream of a transgene. In some cases, two or more REs of any embodiment disclosed herein are operably linked to a transgene, wherein at least one or more of the REs are located upstream, downstream, or both upstream and downstream of the transgene.

In some cases, one or more REs of any embodiment of this disclosure are operably linked to a transgene to drive global expression of the transgene, wherein global expression refers to transgene expression in at least 2, 3, 4, 5, 6, 7, 8, 9, or 10 different cell types. In some cases, one or more REs of any embodiment of this disclosure are operably linked to a transgene to drive global expression of the transgene when delivered systemically into a subject or animal. In some cases, systemic delivery or administration of an expression cassette disclosed herein is delivery via oral, intravenous, intramuscular, intraperitoneal, intrathecal, enteral, and/or parenteral administration. In various embodiments, a RE of any embodiment disclosed herein is human-derived (or a sequence that has at least 80%, 90%, 95% or 99% sequence identity to a sequence in a human reference genome). In some cases, a RE of any embodiment disclosed herein is non-naturally occurring.

Genetic engineering methods can replace a gene, modify a gene, or add a gene to achieve a desired result. Gene therapy is the use of genetic engineering to treat a disease or disorder. Genetic engineering may also be used to modify cells or organisms for the production of one or more proteins of interest. One challenge of genetic engineering is having regulatory elements that drive expression at a sufficiently high level to achieve a therapeutic effect, or at a sufficiently high level to achieve an industrial/production level. Another challenge of genetic engineering is designing an expression cassette small enough to fit within a desired vector, but containing a full coding sequence for a protein of interest and sufficient regulatory sequences to ensure high expression. The cloning capacity of vectors or viral expression vectors is a particular challenge for expression of large transgenes. For example, AAV vectors have a packaging capacity of ~4.8 kb, lentiviruses have a capacity of ~8 kb, adenoviruses have a capacity of ~7.5 kb and alphaviruses have a capacity of ~7.5 kb. Some viruses have larger packaging capacities, for example herpesvirus with a capacity of >30 kb and vaccinia with a capacity of ~25 kb, however there may be advantages to using other viruses. For example, advantages of AAVs include low pathogenicity, very low frequency of integration into the host genome, and the ability to infect dividing and non-dividing cells.

One challenge in gene therapy is ensuring that the transgene is expressed at a sufficiently high level in at least one or more target cell types or tissues to result in a therapeutic effect in vivo. In some cases, increased transgene expression is desired in at least 2, 3, 4, 5, 6, 7, 8, 9, 10 or more different cell types or tissues, e.g., kidney cells, epithelial cells, liver cells, hepatocytes, neurons, fibroblasts, and/or CNS cells. In some cases, increased transgene expression is desired in at least 1, 2, 3, 4, 5, 6, 7, 8, 9, or 10 cell lines ex vivo for protein synthesis, e.g., a mammalian or a human cell line, such as kidney cells, epithelial cells, liver cells, hepatocytes, neurons, fibroblasts, immune cells, and/or CNS cells. Traditional methods for gene therapy have often relied on delivery methods and/or vehicles (e.g., varying the viruses used or capsid sequences of viruses). One technical challenge in the field is increasing level of gene expression, especially when the transgene is large, in one or more cell types or tissues to exert a therapeutic effect. Expression of large transgenes is associated with technical challenges because vectors, e.g., viral or AAV vectors, have limited cloning capacities. In order to express larger transgenes (e.g., a transgene whose sequence is more than 1 kb, 1.5 kb, 2 kb, 2.5 kb, 3 kb, 3.5 kb, 4 kb, 4.5 kb, 5 kb, 5.5 kb, 6 kb, 6.5 kb, 7 kb, or 7.5 kb), smaller regulatory elements must be used to accommodate the larger transgene in the vector. Thus, there is a need for novel short regulatory elements (e.g., REs that are less than or equal to 300 bp, 250 bp, 200 bp, 150 bp, 140 bp, 130 bp, 120 bp, 110 bp, 100 bp, 70 bp, or 50 bp) that result in increased transgene expression in a cell or in vivo as compared to expression without the REs; a negative control (e.g., a sequence known to not drive any expression, an empty vector, or buffer alone control), or as compared to a promoter operably linked to the transgene (e.g., a CMV promoter, SCP, UCL-HLP, etc.).

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within one or more than one standard deviation, per the practice in the art. Alternatively, "about" can mean a range of up to 20%, up to 15%, up to 10%, up to 5%, or up to 1%) of a given value.

The terms "determining", "measuring", "evaluating", "assessing", "assaying", "analyzing", and their grammatical equivalents can be used interchangeably herein to refer to any form of measurement, and include determining if an element is present or not (for example, detection). These terms can include both quantitative and/or qualitative determinations. Assessing may be relative or absolute.

The term "expression" refers to the process by which a nucleic acid sequence or a polynucleotide is transcribed from a DNA template (such as into mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell. In some cases, global expression is desired and refers to expression of a gene (e.g., transgene) in at least 2, 3, 4, 5, 6, 7, 8, 9, 10 or more different cell types or tissues, or expression of a gene in a plurality of cell types. Cell types are distinguished by having a different cell marker, morphology, phenotype, genotype, function, and/or any other means for classifying cell types. In some cases, different cell types or tissues refer to cell types or tissues in vivo. In some cases, different cell types or tissues refer to cell types or tissues ex vivo. In some cases, different cell types or tissues include, but are not limited to, different mammalian cell lines, human cell lines, kidney cells, epithelial cells, liver cells, hepatocytes, neurons, fibroblasts, and/or CNS cells.

As used herein, "operably linked", "operable linkage", "operatively linked", or grammatical equivalents thereof refer to juxtaposition of genetic elements, e.g., a promoter, an enhancer, a polyadenylation sequence, etc., wherein the elements are in a relationship permitting them to operate in the expected manner. For instance, a regulatory element, which can comprise promoter and/or enhancer sequences, is operatively linked to a coding region if the regulatory element helps initiate transcription of the coding sequence. There may be intervening residues between the regulatory element and coding region so long as this functional relationship is maintained.

A "vector" as used herein refers to a macromolecule or association of macromolecules that comprises or associates with a polynucleotide and which can be used to mediate delivery of the polynucleotide to a cell. Examples of vectors include plasmids, viral vectors, liposomes, and other gene delivery vehicles. The vector generally comprises genetic elements, e.g., regulatory elements, operatively linked to a gene to facilitate expression of the gene in a target. The combination of regulatory elements and a gene or genes to which they are operably linked for expression is referred to as an "expression cassette".

The term "AAV" is an abbreviation for adeno-associated virus, and may be used to refer to the virus itself or a derivative thereof. The term covers all serotypes, subtypes, and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV1, AAV2, AAV3, AAV4, AAV5, AAV6, AAV7, AAV8, AAV9, AAV10, AAV11, AAV12, rh10, and hybrids thereof, avian AAV, bovine AAV, canine AAV, equine AAV, primate AAV, non-primate AAV, and ovine AAV. The genomic sequences of various serotypes of AAV, as well as the sequences of the native terminal repeats (TRs), Rep proteins, and capsid subunits are known in the art. Such sequences may be found in the literature or in public databases such as GenBank. A "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two, AAV inverted terminal repeat sequences (ITRs). The term rAAV vector encompasses both rAAV vector particles and rAAV vector plasmids. An rAAV vector may either be single-stranded (ssAAV) or self-complementary (scAAV). An "AAV virus" or "AAV viral particle" or "rAAV vector particle" refers to a viral particle composed of at least one AAV capsid protein and an encapsidated polynucleotide rAAV vector. If the particle comprises a heterologous polynucleotide (i.e., a polynucleotide other than a wild-type AAV genome such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

As used herein, the terms "treat", "treatment", "therapy" and the like refer to obtaining a desired pharmacologic and/or physiologic effect, including, but not limited to, alleviating, delaying or slowing the progression, reducing the effects or symptoms, preventing onset, inhibiting, ameliorating the onset of a diseases or disorder, obtaining a beneficial or desired result with respect to a disease, disorder, or medical condition, such as a therapeutic benefit and/or a prophylactic benefit. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease. A therapeutic benefit includes eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In some cases, for prophylactic benefit, the compositions are administered to a subject at risk of developing a particular disease, or to a subject reporting one or more of the physiological symptoms of a disease, even though a diagnosis of this disease may not have been made. The methods of the present disclosure may be used with any mammal. In some cases, the treatment can result in a decrease or cessation of symptoms (e.g., a reduction in the frequency or duration of seizures). A prophylactic effect includes delaying or eliminating the appearance of a disease or condition, delaying or eliminating the onset of symptoms of a disease or condition, slowing, halting, or reversing the progression of a disease or condition, or any combination thereof.

The term "effective amount" or "therapeutically effective amount" refers to that amount of a composition described herein that is sufficient to affect the intended application, including but not limited to disease treatment, as defined below. The therapeutically effective amount may vary depending upon the intended treatment application (in a cell or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in a target cell. The specific dose will vary depending on the particular composition chosen, the dosing regimen to be followed, whether it is administered in combination with other compounds, timing of administration, the tissue to which it is administered, and the physical delivery system in which it is carried.

A "fragment" of a nucleotide or peptide sequence is meant to refer to a sequence that is less than that believed to be the "full-length" sequence.

A "variant" of a molecule refers to allelic variations of such sequences, that is, a sequence substantially similar in structure and biological activity to either the entire molecule, or to a fragment thereof. As used herein, a variant of a gene refers to a sequence having a genetic alternation or a mutation as compared to the most common wild-type DNA sequence (e.g., cDNA, or the sequence referenced by its GenBank or sequence corresponding to a protein sequence referenced by its UniProt accession number). A gene variant encompasses mutants, such as a mutant that has an enhanced activity or function as compared to the wild-type sequence; any known subunit of a protein; and known isoforms of a gene that result from alternative splicing.

The term "functional fragment" is intended to include the "fragments", "variants", "analogues", or "chemical derivatives" of a molecule. A "functional fragment" of a DNA or protein sequence possesses at least a biologically active fragment of the sequence, which refers to a fragment that retains a biological activity (either functional or structural) that is substantially similar to a biological activity of the full-length DNA or protein sequence. A biological activity of a DNA sequence can be its ability to influence expression in a manner known to be attributed to the full-length sequence. For example, a functional fragment of a regulatory element will retain the ability to influence transcription as the full-length RE.

The terms "subject" and "individual" are used interchangeably herein to refer to a vertebrate, preferably a mammal, more preferably a human. "Subject" refers to an animal, such as a mammal, for example a human. The methods described herein can be useful in human therapeutics, veterinary applications, and/or preclinical studies in animal models of a disease or condition. In some cases, the subject is a mammal, and in some cases, the subject is human.

The term "in vivo" refers to an event that takes place in a subject's body.

The term "in vitro" refers to an event that takes places outside of a subject's body. For example, an in vitro assay encompasses any assay run outside of a subject. In vitro assays encompass cell-based assays in which cells alive or dead are employed. In vitro assays also encompass a cell-free assay in which no intact cells are employed.

Sequence comparisons, such as for the purpose of assessing identities, mutations, or where one or more positions of a test sequence fall relative to one or more specified positions of a reference sequence, may be performed by any suitable alignment algorithm, including but not limited to the Needleman-Wunsch algorithm (see, e.g., the EMBOSS Needle aligner available at www(dot)ebi(dot)ac(dot)uk/ Tools/psa/emboss_needle/, optionally with default settings), the BLAST algorithm (see, e.g., the BLAST alignment tool available at blast.nebi.nlm.nih.govblast(dot)ncbi(dot)nlm (dot)nih(dot)gov/Blast.cgi, optionally with default settings), and the Smith-Waterman algorithm (see, e.g., the EMBOSS Water aligner available at www(dot)ebi(dot)ac(dot)uk/ Tools/psa/emboss_water/, optionally with default settings). Optimal alignment may be assessed using any suitable parameters of a chosen algorithm, including default parameters.

In general, "sequence identity" or "sequence homology", which can be used interchangeably, refer to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity", also referred to as "percent homology". The percent identity to a reference sequence (e.g., nucleic acid or amino acid sequences), which may be a sequence within a longer molecule (e.g., polynucleotide or polypeptide), may be calculated as the number of exact matches between two optimally aligned sequences divided by the length of the reference sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin and Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the sequences being compared. Default parameters are provided to optimize searches with short query sequences, for example, with the blastp program. The program also allows use of an SEG filter to mask-off segments of the query sequences as determined by the SEG program of Wootton and Federhen, Computers and Chemistry 17: 149-163 (1993). Ranges of desired degrees of sequence identity are approximately 80% to 100% and integer values there between. Typically, the percent identities between a disclosed sequence and a claimed sequence are at least 80%, at least 85%, at least 90%, at least 95%, at least 98%, or at least 99%. In general, an exact match indicates 100% identity over the length of the reference sequence. In some cases, reference to percent sequence identity refers to sequence identity as measured using BLAST (Basic Local Alignment Search Tool). In other cases, ClustalW can be used for multiple sequence alignment.

Unless otherwise indicated, all terms used herein have the same meaning as they would to one skilled in the art and the practice of the present invention will employ conventional techniques of molecular biology, microbiology, and recombinant DNA technology, which are within the knowledge of those of skill of the art.

Regulatory Elements

Regulatory elements can function at the DNA and/or the RNA level. Regulatory elements can function to modulate gene expression selectivity in a cell type of interest. Regulatory elements can function to modulate gene expression at the transcriptional phase, post-transcriptional phase, or at the translational phase of gene expression. Regulatory elements include, but are not limited to, promoter, enhancer, intronic, or other non-coding sequences. At the RNA level, regulation can occur at the level of translation (e.g., stability elements that stabilize mRNA for translation), RNA cleavage, RNA splicing, and/or transcriptional termination. In some cases, regulatory elements can recruit transcriptional factors to a coding region that increase gene expression selectivity in a cell type of interest. In some cases, regulatory elements can increase the rate at which RNA transcripts are produced, increase the stability of RNA produced, and/or increase the rate of protein synthesis from RNA transcripts.

Regulatory elements are nucleic acid sequences or genetic elements which are capable of influencing (e.g., increasing) expression of a gene (e.g., a reporter gene such as EGFP or luciferase; a transgene; or a therapeutic gene) in one or more cell types or tissues. In some cases, a regulatory element can be a transgene, an intron, a promoter, an enhancer, UTR, an inverted terminal repeat (ITR) sequence, a long terminal repeat sequence (LTR), stability element, posttranslational response element, or a polyA sequence, or a combination thereof. In some cases, the regulatory element is a promoter, an enhancer, an intronic sequence, or a combination thereof. In some cases, the regulatory element is derived from a human sequence (e.g., hg19).

One method of isolating a regulatory element includes isolating nuclei from one or more cell types from an animal model, which can be achieved by using an affinity purification method that isolates one or more tissues or cell types (e.g., beads that bind to certain cell types), using high-throughput natural priming and DNA synthesis to generate a pool of sequences from open chromatin regions in the nuclei, sequencing the pool of sequences to identify putative sequences that drive gene expression in one or more tissues or cell types, and expression in a reporter system in one or more cell lines in vitro and/or in an animal model. In some cases, two or more regulatory elements are combined to form a larger RE. In some cases, combined regulatory elements exhibit enhanced gene expression in a plurality of cell types, e.g., in at least 2, 3, 4, 5, 6, or more cell types. In some instances, regulatory elements are truncated one or more bases at a time to determine the minimal amount of sequence that retains its ability to increase transgene expression. Smaller regulatory elements that retain transgene expression activity are helpful for making gene therapy comprising a large transgene, or where the cloning capacity of a vector or a plasmid is limited in view of the size of a transgene that one wishes to deliver using gene therapy. For example, one or more REs of this disclosure, when operably linked to a transgene, drive increased transgene expression, wherein the transgene is at least 1 kb, 1.5 kb, 2 kb, 2.5 kb, 3 kb, 3.5 kb, 4 kb, 4.5 kb, 5 kb, 5.5 kb, 6 kb, 6.5 kb, 7 kb, or 7.5 kb. In some cases, such increase in transgene expression is at least 1.5 fold, at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 50 fold, at least 100 fold, at least 200 fold, at least 300 fold, at least 400 fold, at least 500 fold, at least 600 fold, at least 700 fold, at least 800 fold, at least 900 fold, or at least 1000 fold as compared to a negative control, a constitutive promoter, a CMV promoter, super core promoter, TTR promoter, Proto 1 promoter, UCL-HLP promoter, or CMVe promoter.

In some cases, a regulatory element of this disclosure results in high or increased expression of an operably linked transgene, wherein the high or increased expression is determined as compared to a control, e.g., a constitutive promoter, a CMV promoter, CAG, super core promoter (SCP), TTR promoter, Proto 1 promoter, UCL-HLP promoter, min CMV, EFS, or CMVe promoter. Other controls that can be used to determine high or increased transgene expression by a regulatory element disclosed herein include buffer alone or vector alone. In some cases, a positive control refers to a RE with known expression activity, such as SEQ ID NO: 4, which can be used for comparison. In some cases, a regulatory element drives comparable or higher transgene expression as comparable to a positive control (e.g., SEQ ID NO: 4 or a known promoter operably linked to the transgene).

In some cases, the 5'-most 17 nucleotides of SEQ ID NOs: 13-17 can be removed to form shorter REs that retain the expression activity. For examples, SEQ ID NOs: 13-17 without the 5'-most 17 nucleotides are SEQ ID NOs: 30, 26, 28, 23, and 22, respectively.

In other cases, two or more relatively short REs can be combined to form a larger RE having high transgene expression activity and/or size-normalized gene expression activity. For examples, SEQ ID NO: 17 can be combined with SEQ ID NO: 22; or SEQ ID NO: 16 can be combined with SEQ ID NO: 22.

The present disclosure contemplates relatively short, human-derived regulatory elements that increase expression of an operably linked transgene. In some cases, a short human-derived RE is any one of the sequences at TABLE 1, or SEQ ID NOs: 1-2, 13-17, and 22-41.

TABLE 1

Examples of Regulatory Elements (REs)

| SEQ ID NO: | Sequence (5'-to-3') | Length |
|---|---|---|
| 1 | GTAAGGTAAGAATTGAATTTCTCAGTTGAAGGATGCTTACACTCTT GTCCATCTAG | 56 bp |
| 2 | GTGTGTATGCTCAGGGGCTGGGAAAGGAGGGGAGGGAGCTCCGGC TCAG | 49 bp |
| 3 | GTGATGCGGTTTTGGCAGTACATCAATGGGCGTGGATAGCGGTTTG ACTCACGGGGATTTCCAAGTCTCCACCCCATTGACGTCAATGGGAG TTTGTTTTGGCACCAAAATCAACGGGACTTTCCAAAATGTCGTAAC AACTCCGCCCCATTGACGCAAATGGGCGGTAGGCGTGTACGGTGG GAGGTCTATATAAGCAGAGCTGGTACCGTAAGGTAAGAATTGAAT TTCTCAGTTGAAGGATGCTTACACTCTTGTCCATCTAG | 266 bp |
| 4 | GTGATGCGGTTTTGGCAGTACATCAATGGGCGTGGATAGCGGTTTG ACTCACGGGGATTTCCAAGTCTCCACCCCATTGACGTCAATGGGAG TTTGTTTTGGCACCAAAATCAACGGGACTTTCCAAAATGTCGTAAC AACTCCGCCCCATTGACGCAAATGGGCGGTAGGCGTGTACGGTGG GAGGTCTATATAAGCAGAGCTGGTACCGTGTGTATGCTCAGGGGC TGGGAAAGGAGGGGAGGGAGCTCCGGCTCAG | 259 bp |
| 13 | GTGATGACGTGTCCCATAAGGCCCCTCGGTCTAAGGCTTCCCTATT TCCTGGTTCGCCGGCGGCCATTTTGGGTGGAAGCGATAGCTGAGTG GCGGCGGCTGCTGATTGTGTTCTAG | 117 bp |

TABLE 1-continued

Examples of Regulatory Elements (REs)

| SEQ ID NO: | Sequence (5'-to-3') | Length |
|---|---|---|
| 14 | GTGATGACGTGTCCCATACTTCCGGGTCAGGTGGGCCGGCTGTCTT GACCTTCTTTGCGGCTCGGCCATTTTGTCCCAGTCAGTCCGGAGGC TGCGGCTGCAGAAGTACCGCCTGCG | 117 bp |
| 15 | GTGATGACGTGTCCCATATTTTCATCTCGCGAGACTTGTGAGCGGC CATCTTGGTCCTGCCCTGACAGATTCTCCTATCGGGGTCACAGGGA CGCTAAGATTGCTACCTGGACTTTC | 117 bp |
| 16 | GTGATGACGTGTCCCATGGCCTCATTGGATGAGAGGTCCCACCTCA CGGCCCGAGGCGGGGCTTCTTTGCGCTTAAAAGCCGAGCCGGGCC AATGTTCAAATGCGCAGCTCTTAGTC | 117 bp |
| 17 | GTGATGACGTGTCCCATCCCCCCTCCACCCCCTAGCCCGCGGAGCA CGCTGGGATTTGGCGCCCCCCTCCTCGGTGCAACCTATATAAGGCT CACAGTCTGCGCTCCTGGTACACGC | 117 bp |
| 22 | CCCCCCTCCACCCCCTAGCCCGCGGAGCACGCTGGGATTTGGCGCC CCCTCCTCGGTGCAACCTATATAAGGCTCACAGTCTGCGCTCCTG GTACACGC | 100 bp |
| 23 | GGCCTCATTGGATGAGAGGTCCCACCTCACGGCCCGAGGCGGGGC TTCTTTGCGCTTAAAAGCCGAGCCGGGCCAATGTTCAAATGCGCAG CTCTTAGTC | 100 bp |
| 24 | GGGTGGGGCCCGCGCGTATAAAGGGGGCGCAGGCGGGCTGGGCG TTCCACAGGCCAAGTGCGCTGTGCTCGAGGGGTGCCGGCCAGGCC TGAGCGAGCGA | 100 bp |
| 25 | GGTGCGATATTCGGATTGGCTGGAGTCGGCCATCACGCTCCAGCTA CGCCACTTCCTTTTCGTGGCACTATAAAGGGTGCTGCACGGCGCTT GCATCTCT | 100 bp |
| 26 | ACTTCCGGGTCAGGTGGGCCGGCTGTCTTGACCTTCTTTGCGGCTC GGCCATTTTGTCCCAGTCAGTCCGGAGGCTGCGGCTGCAGAAGTA CCGCCTGCG | 100 bp |
| 27 | GCTGAGCGCGCGCGATGGGGCGGGAGGTTTGGGGTCAAGGAGCA AACTCTGCACAAGATGGCGGCGGTAGCGGCAGTGGCGGCGCGTAG GAGGCGGTGAG | 100 bp |
| 28 | ATTTTCATCTCGCGAGACTTGTGAGCGGCCATCTTGGTCCTGCCCT GACAGATTCTCCTATCGGGGTCACAGGGACGCTAAGATTGCTACCT GGACTTTC | 100 bp |
| 29 | TGGGACCCCCGGAAGGCGGAAGTTCTAGGGCGGAAGTGGCCGAG AGGAGAGGAGAATGGCGGCGGAAGGCTGGATTTGGCGTTGGGGCT GGGGCCGGCGG | 100 bp |
| 30 | AAGGCCCCTCGGTCTAAGGCTTCCCTATTTCCTGGTTCGCCGGCGG CCATTTGGGTGGAAGCGATAGCTGAGTGGCGGCGGCTGCTGATT GTGTTCTAG | 100 bp |
| 31 | AGTGACCCGGAAGTAGAAGTGGCCCTTGCAGGCAAGAGTGCTGGA GGGCGGCAGCGGCGACCGGAGCGGTAGGAGCAGCAATTTATCCGT GTGCAGCCCC | 100 bp |
| 32 | GGGAGGGGCGCGCTGGGGAGCTTCGGCGCATGCGCGCTGAGGCCT GCCTGACCGACCTTCAGCAGGGCTGTGGCTACCATGTTCTCTCGCG CGGGTGTCG | 100 bp |
| 33 | ACTGCGCACGCGCGCGGTCGCACCGATTCACGCCCCCTTCCGGCG CCTAGAGCACCGCTGCCGCCATGTTGAGGGGGGGACCGCGACCAG CTGGGCCCCT | 100 bp |
| 34 | CCCTCGAGGGGCGGAGCAAAAAGTGAGGCAGCAACGCCTCCTTAT CCTCGCTCCCGCTTTCAGTTCTCAATAAGGTCCGATGTTCGTGTAT AAATGCTCG | 100 bp |
| 35 | CTTGGTGACCAAATTTGAAAAAAAAAAAAAACCGCGCCAACTCAT GTTGTTTTCAATCAGGTCCGCCAAGTTTGTATTTAAGGAACTGTTT CAGTTCATA | 100 bp |

TABLE 1-continued

Examples of Regulatory Elements (REs)

| SEQ ID NO: | Sequence (5'-to-3') | Length |
|---|---|---|
| 36 | GGCTGAGCTATCCTATTGGCTATCGGGACAAAATTTGCTTGAGCCA ATCAAAGTGCTCCGTGGACAATCGCCGTTCTGTCTATAAAAGGTG AAGCAGCG | 100 bp |
| 37 | GGAAGTGCCAGACCGGAGGTGCGTCATTCACCGGCGACGCCGATA CGGTTCCTCCACCGAGGCCCATGCGAAGCTTTCCACTATGGCTTCC AGCACTGTC | 100 bp |
| 38 | CCCTCGAGGGGCGGAGCAAAAAGTGAGGCAGCAACGCCTCCTTAT CCTCGCTCCCGCTTTCAGTTCTCAATAAGGTCCGATGTTCGTGTAT AAATGCTCG | 100 bp |
| 39 | CTTGGTGACCAAATTTGAAAAAAAAAAAAAACCGCGCCAACTCAT GTTGTTTTCAATCAGGTCCGCCAAGTTTGTATTTAAGGAACTGTTT CAGTTCATA | 100 bp |
| 40 | GGCTGAGCTATCCTATTGGCTATCGGGACAAAATTTGCTTGAGCCA ATCAAAGTGCTCCGTGGACAATCGCCGTTCTGTCTATAAAAGGTG AAGCAGCG | 100 bp |
| 41 | GGAAGTGCCAGACCGGAGGTGCGTCATTCACCGGCGACGCCGATA CGGTTCCTCCACCGAGGCCCATGCGAAGCTTTCCACTATGGCTTCC AGCACTGTC | 100 bp |

In some cases, a relatively short human-derived RE comprises a sequence of TABLE 1 or SEQ ID NOs: 1-2, 13-17, and 22-41; or a sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity (e.g., local sequence identity) to a sequence of TABLE 1 or SEQ ID NOs: 1-2, 13-17, and 22-41. In some cases, a short human-derived RE comprises a non-naturally occurring sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a human sequence of hg19. In some cases, a relatively short human-derived RE comprises a non-naturally occurring sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to a human sequence located at one of the following genomic or chromosomal locations listed in TABLE 2.

TABLE 2

Examples of Genomic Locations for Deriving REs

| SEQ ID NO: | Genomic location | Fold increase over negative control (normalized) |
|---|---|---|
| 22 | PEG10-cs;PEG10-he_chr7:94285387-94285887-3 | 154 |
| 23 | SAT1-he_chrX:23801204-23801704-1 | 207 |
| 24 | CDKN1C-he;CDKN1C-cs_chr11:2906751-2907251-3 | 532 |
| 25 | BTG1-cs;BTG1-he_chr12:92539423-92539923-3 | 501 |
| 26 | ATP5A1-he_chr18:43678011-43678511-3 | 1049 |
| 27 | GANAB-he_chr11:62413828-62414328-3 | 54 |
| 28 | ATP5F1-he_chr1:111991856-111992356-3 | 675 |
| 29 | LMAN2-cs_chr5:176778403-176778903-3 | |

TABLE 2-continued

Examples of Genomic Locations for Deriving REs

| SEQ ID NO: | Genomic location | Fold increase over negative control (normalized) |
|---|---|---|
| 30 | RAB1A-he_chr2:65356988-65357488-3 | 1049 |
| 31 | NEDD8-he_chr14:24701287-24701787-3 | 253 |
| 32 | ATP5C1-he_chr10:7829892-7830392-3 | |
| 33 | SSR4-he_chrX:153059879-153060379-1 | |
| 34 | HIST1H4B-he_chr6:26027230-26027730(−)-2 | |
| 35 | HIST1H4C-he_chr6:26103854-26104354(+)-3 | 313 |
| 36 | HIST2H2AA3-he_chr1:149814228-149814728(−)-4 | |
| 37 | TOMM6-he_chr6:41755153-41755653(+)-3 | |
| 38 | HIST1H4B-he_chr6:26027230-26027730(−)-2 | |
| 39 | HIST1H4C-he_chr6:26103854-26104354(+)-3 | |
| 40 | HIST2H2AA3-he_chr1:149814228-149814728(−)-4 | |
| 41 | TOMM6-he_chr6:41755153-41755653(+)-3 | |

In some cases, a relatively short human-derived RE is derived from a promoter at a genomic location listed in TABLE 2 and exhibits at least 1.5 fold, at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 50 fold, at least 100 fold, at least 200 fold, at least 300 fold, at least 400 fold, at least 500 fold, at least 600 fold, at least 700 fold, at least 800 fold, at least 900 fold, or at least 1000 fold transgene expression as compared to a negative control (e.g., vector alone control, buffer control, or a sequence known to have no expression activity), or as compared to a constitutive promoter, a CMV promoter, super core promoter, TTR promoter, Proto 1 promoter, UCL-HLP promoter, or CMVe promoter.

In some cases, a relatively short RE of this disclosure comprises an intronic sequence (e.g., SEQ ID NO: 1 or SEQ ID NO: 2), when operably linked to a transgene in an expression cassette, results in normalized gene (e.g., luciferase, ATP7B, or FVIII) expression of at least 50 fold, 100 fold, 500 fold, 1000 fold, or 5000 fold, or more than 1000 fold as compared to transgene expression under the control of SCP or a negative control (e.g., vector alone, buffer alone, or a sequence without any expression activity). In some cases, a relatively short RE of this disclosure (e.g., SEQ ID NO: 1 or SEQ ID NO: 2), when operably linked to a transgene in an expression cassette, results in size-normalized activity that is at least 1.5 fold, 2.5 fold, 5 fold, 10 fold, 15 fold, or 20 or more fold as compared to the size-normalized activity of SCP or CAG. In some cases, a relatively short RE of this disclosure (e.g., SEQ ID NO: 1 or SEQ ID NO: 2), when operably linked to a transgene (e.g., luciferase) in an expression cassette, results in total luciferase luminescence (in photons/sec) that is at least 1.5 fold, 2 fold, 2.5 fold, 3 fold, 4 fold, 5 fold, 10 or more fold as compared to luciferase under the control of SCP, SerpE_TTR, Proto1, min CMV, UCL-HLP, or CMVe; or as compared to a buffer control. In some cases, a relatively short RE of this disclosure (e.g., SEQ ID NO: 1 or SEQ ID NO: 2), when operably linked to human FVIII in an expression cassette, results in an increase in human FVIII concentration in vivo, wherein the increase in concentration is at least 1 IU/mL, 1.2 IU/mL, 1.5 IU/mL, or more than 1 IU/mL of FVIII as compared to buffer control or UCL-HLP operably linked to FVIII.

In some cases, a relatively short RE of this disclosure is derived from a human promoter sequence (e.g., SEQ ID NOs: 13-17 and 22-41), when operably linked to a transgene (e.g., luciferase, ATP7B, or FVIII) in an expression cassette, results in normalized transgene expression of at least 50 fold, 100 fold, 200 fold, 300 fold, 400 fold, 500 fold, 600 fold, 700 fold, 800 fold, 900 fold, or 1000 or more fold as compared to a negative control (e.g., vector alone, buffer alone, or a sequence known to have no expression activity). In some instances, the RE results in normalized luciferase expression of at least 5 fold, 10 fold, or 100 or more fold as compared to luciferase expression under the control of CMV or CMV+CMVe. In some embodiments, two or more REs can be combined to form a larger RE. In some cases, the RE is located upstream of the transgene.

In some cases, a relatively short human-derived RE disclosed herein comprises no more than 40 bp, 45 bp, 49 bp, 50 bp, 56 bp, 60 bp, 70 bp, 80 bp, 90 bp, 100 bp, 110 bp, 117 bp, 120 bp, 130 bp, 140 bp, 150 bp, 160 bp, 170 bp, 180 bp, 190 bp, 200 bp, 210 bp, 220 bp, 230 bp, 240 bp, 250 bp, 259 bp, 260 bp, 265 bp, 270 bp, 280 bp, 290 bp, 300 bp, 310 bp, 320 bp, 330 bp, 340 bp, 350 bp, 360 bp, 370 bp, 380 bp, 390 bp, or 400 bp, and comprises a sequence according to any one of TABLE 1 or SEQ ID NOs: 1-2, 13-17, and 22-41. In some cases, two or more, three or more, four or more, five or more, six or more, seven or more, eight or more, nine or more, or ten or more of the sequences listed in TABLE 1, or SEQ ID NOs: 1-2, 13-17, and 22-41, can be combined or used in tandem in an expression cassette or vector.

In various aspects, relatively short, human-derived regulatory elements are especially useful when there is a size constraint on a vector (such as in AAV gene therapy) or a need for a very high level of expression (such as in ex vivo protein production). The regulatory elements disclosed herein may be constitutive or inducible. Thus, the present disclosure provides the benefits of both high expression as well as short regulatory elements. In some cases, a RE disclosed herein exhibits higher expression level per base pair or per nucleotide as compared to a control regulatory element, such as a constitutive promoter, a CMV promoter, super core promoter, TTR promoter, Proto 1 promoter, UCL-HLP promoter, or CMVe promoter. In some cases, SEQ ID NO: 4 is used as a control for comparing levels of gene expression.

In some cases, one or more REs of this disclosure are adapted for increasing expression of a large transgene (e.g., in a gene therapy or an expression cassette) because the REs enhance transgene expression without taking up significant cloning capacity. In some cases, a RE of this disclosure is no more than 49 bp, 50 bp, 56 bp, 60 bp, 70 bp, 80 bp, 90 bp, 100 bp, 110 bp, 117 bp, 120 bp, 130 bp, 140 bp, 150 bp, 160 bp, 170 bp, 180 bp, 190 bp, 200 bp, 210 bp, 220 bp, 230 bp, 240 bp, 250 bp, 259 bp, 260 bp, 265 bp, 270 bp, 280 bp, 290 bp, 300 bp, 310 bp, 320 bp, 330 bp, 340 bp, 350 bp, 360 bp, 370 bp, 380 bp, 390 bp, or 400 bp, and comprises a sequence according to any one of TABLE 1 or SEQ ID NOs: 1-2, 13-17, and 22-41, or a sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity thereto. In some cases, a relatively short RE of this disclosure increases transgene expression by at least 1.5 fold, at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 50 fold, at least 100 fold, at least 200 fold, at least 300 fold, at least 400 fold, at least 500 fold, at least 600 fold, at least 700 fold, at least 800 fold, at least 900 fold, or at least 1000 fold as compared to transgene expression without the RE, or as compared to a negative control (e.g., vector alone control, buffer alone, or a sequence known to have no expression activity). In some cases, a control is a constitutive promoter operably linked to the same transgene (e.g., luciferase). Examples of other promoters that can be used as a control for comparison to transgene expression of a RE operably to the transgene include, but are not limited to, a CMV promoter, a super core promoter, a TTR promoter, a Proto 1 promoter, a UCL-HLP promoter, an AAT promoter, a KAR promoter, a EF1α promoter, EFS promoter, or CMVe enhancer/CMV promoter combination.

A regulatory element herein can be a promoter, and when included in an expression cassette will drive transcription of a downstream sequence, which may be closely associated or in direct contact with the downstream sequence (e.g., a transgene). A promoter may drive high, medium, or low expression of a linked transgene. In some cases, a promoter may be specific for one or more cell types, or may express at a similar level in many or a plurality of cell types (e.g., in at least 2, 3, 4, 5, 6, 7, 8, 9, or 10 cell types).

In some cases, a RE disclosed herein comprises a human-derived sequence. In some cases, a RE of this disclosure is non-naturally occurring. The term "human-derived" as used herein refers to a sequence that has at least 80%, 90%, 95% or 99% sequence identity to a sequence in a human reference genome (or a human genome build, such as hg19). A homologous sequence may be a sequence which has a region with at least 80% sequence identity (e.g., as measured by BLAST) as compared to a region of the human genome. For example, a sequence that is at least 80%, at least 85%, at least 90%, at least 91%, at least 92%, at least 93%, at least 94%, at least 95%, at least 96%, at least 97%, at least 98%, or at least 99% homologous to a human sequence is deemed a human derived sequence.

In some cases, a regulatory element contains a human-derived sequence and additional sequences such that overall the regulatory element has low sequence identity to a sequence in the human genome, while a part of the regulatory element has 100% sequence identity (or local sequence identity) to a sequence in the human genome. In some instances, percent sequence identity refers to the homology within a region covering at least 50%, 55%, 60%, 65%, 70%, 75%, 80%, 85%, 90%, 91%, 92%, 93%, 94%, 95%, 96%, 97%, 98%, 99%, or 100% of any of the sequences listed in TABLE 1 or SEQ ID NOs: 1-2, 13-17, and 22-41.

In some cases, a human-derived regulatory element is a sequence that is 100% identical to a human sequence. In some instances, the sequence of a regulatory element is 100% human derived, wherein the RE differs from the human sequence by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, or 95 nucleotides or base pairs.

In other instances, at least 5%, 10%, 20%, 30%, 40%, 50%, 60%, 70%, 80%, 90%, 95%, 98%, or 99% of the regulatory element sequence is human derived. For example, a regulatory element can have 50% of its sequence be human derived, and the remaining 50% be non-human derived (e.g., mouse derived or fully synthetic). For further example, a regulatory element that is regarded as 50% human derived and comprises 300 bp may have an overall 45% sequence identity to a sequence in the human genome, while base pairs 1-150 of the RE may have 90% identity (e.g., local sequence identity) to a similarly sized region of the human genome.

In some cases, a RE of this disclosure comprises a promoter sequence, an intronic sequence, an enhancer sequence, a 5' UTR sequence, or a combination thereof. In some cases, a RE of this disclosure is non-naturally occurring. In some cases, a RE of this disclosure is human-derived (or a sequence that has at least 80%, 90%, 95% or 99% sequence identity to a sequence in a human reference genome).

In some cases, a relatively short regulatory element disclosed herein may be derived from a genomic promoter sequence (e.g., genomic locations in TABLE 2). In some cases, a regulatory element disclosed herein may be derived from both genomic promoter sequence and 3' untranslated region (3' UTR). In some cases, a regulatory element disclosed herein may be derived from intergenic sequence. In some cases, a regulatory element disclosed herein may be derived from genomic sequence downstream of a gene, or from 5' UTR sequence, or a mixture of 5' UTR and downstream sequence.

A regulatory element herein can be an enhancer, and its presence in an expression vector or cassette along with a promoter increases expression of an operably linked transgene as compared to expression of the same transgene by the promoter without the enhancer. An enhancer may increase expression of a linked transgene through either a transcriptional mechanism, posttranscriptional mechanism, or both.

In some cases, a regulatory element herein is an intronic sequence (e.g., SEQ ID NOs: 1-2), or comprises an intron, and its presence in an expression vector or cassette along with a promoter increases expression of an operably linked transgene as compared to expression of the same transgene by the promoter without the intronic sequence. An intronic sequence or regulatory element can increase expression of a linked transgene through either a transcriptional mechanism, posttranscriptional mechanism, or both.

In some cases, a regulatory element herein is a promoter sequence (e.g., SEQ ID NOs: 13-17 and 22-41), or comprises a promoter sequence, and it can be operably linked to a transgene in an expression cassette without any other promoter sequences and/or enhancer sequences to express the transgene.

In various embodiments, one or more of REs of TABLE 1 can drive increased expression of an operably linked transgene without the need for a promoter in an expression cassette. In some embodiments, where a large transgene (e.g., a transgene whose sequence is more than 1 kb, 1.5 kb, 2 kb, 2.5 kb, 3 kb, 3.5 kb, 4 kb, 4.5 kb, 5 kb, 5.5 kb, 6 kb, 6.5 kb, 7 kb, or 7.5 kb) is too large to be expressed in a conventional expression cassette, such transgene can be operably linked to one or more REs of TABLE 1 without the need for a conventional promoter and be expressed at higher levels as compared to transgene expression in an expression cassette without the REs, or as compared to a control (e.g., an empty vector, a constitutive promoter, a CMV promoter, super core promoter, TTR promoter, Proto 1 promoter, UCL-HLP promoter, or CMVe promoter).

One of the benefits of the regulatory elements disclosed herein is their relatively short length. In some instances, a regulatory element of the invention is less than or equal to 40 bp, 50 bp, 60 bp, 70 bp, 80 bp, 90 bp, 100 bp, 200 bp, 300 bp, or 400 bp in length. In some instances, a regulatory element is less than or equal to 100 bp in length, <90 bp, <80 bp, <70 bp, <60 bp, or <50 bp, or between 48-57 bp, or between 40-60 bp, or 50-100 bp in length. In some cases, the regulatory element described herein is 40-50 bp, 45-55 bp, 50-60 bp, or 55-65 bp. In some cases, the regulatory element is 45-60 bp. In some cases, the regulatory element described herein is 49 bp or 56 bp. For example, regulatory elements SEQ ID NO: 1 is 56 bp in length, and regulatory element SEQ ID NO: 2 is 49 bp in length. In some cases, the regulatory element may be between 100 bp and 150 bp, between 110 bp and 140 bp, between 110 bp and 130 bp, or between 115 bp and 125 bp. For example, regulatory elements SEQ ID NOs. 13-17 are 117 bp in length. In some cases, regulatory elements are or are about 100 bp. For example, SEQ ID NOs: 22-41 are each 100 bp in length.

A regulatory element of the disclosure preferably has a human-derived sequence. A regulatory element may be derived from a genomic sequence upstream of a transcription initiation site, a 5' UTR sequence, an exonic sequence, an intronic sequence, or a 3' UTR sequence. In some embodiments, a human-derived regulatory element is an intronic human-derived sequence. In some cases, a human-derived regulatory element is a promoter sequence derived from a human sequence. In some embodiments, a human-derived regulatory element is an intronic sequence of SEQ ID NO: 1, SEQ ID NO: 2, or a combination thereof, or a sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity thereto (e.g., as measured by BLAST). In some embodiments, a human-derived regulatory element is a promoter sequence of SEQ ID NO: 13, 14, 15, 16, 17, 22, 23, 24, 25, 26, 27, 28, 29, 30, 31, 32, 33, 34, 35, 36, 37, 38, 39, 40, 41, or a combination thereof, or a sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity thereto (e.g., as measured by BLAST).

In some cases, the regulatory elements comprise part or all of a 5' untranslated region (5' UTR). 5' UTR regulatory elements can influence expression of a gene in several different ways. 5' UTR regulatory elements can contain binding sites for RNA binding proteins. Further, secondary structures formed by regulatory elements in the 5' UTR can affect the binding of RNA binding proteins required for translation. In some examples, the regulatory element can have a high degree of secondary structure. In some cases, the regulatory element can have little or no secondary structure. The regulatory element can also contain an internal ribosome entry site (IRES), allowing for 5' cap independent translation. The regulatory element can contain an upstream translation initiation codon (uAUG). In some embodiments, the regulatory element does not contain an upstream translation initiation codon. In some embodiments, the regulatory element does not contain any codon within one base of an AUG codon, or contains fewer codons similar to an AUG codon than expected by chance. In some cases, the regulatory element can contain an upstream open reading frame, which occurs when an upstream AUG (or sufficiently similar sequence) is present, followed by an in frame stop codon. In some examples, the regulatory element does not comprise an uORF. In some cases, the regulatory elements contain microRNA binding sites, or binding sites for RNA binding proteins.

In some instances, a regulatory element of the disclosure comprises a sequence that is homologous to a human-derived sequence. A sequence is "homologous to a human-derived sequence" if it has at least 80%, 85%, 90%, 95%, 98% or 99% sequence identity to a human sequence. Preferably, a sequence that is homologous to a human-derived regulatory sequence is at least 90% identical to a human sequence. In some embodiments, a regulatory element herein is one that has at least 80%, 85%, 90%, 95%, 98% or 99% sequence identity to SEQ ID NOs: 1-2, 13-17, and 22-41. When a regulatory element is homologous to any of SEQ ID NOs: 1-2, such regulatory element still results in higher expression of an operably linked transgene (when a promoter is also present in the expression vector or cassette), as compared to a similar vector without the regulatory element. Such higher expression of a transgene can be observed, e.g., in expression in HEK293T or CHO cells. In some cases, such higher expression of a transgene can be observed in a plurality of cell types, e.g., two or more mammalian cell lines, human cell lines, kidney cells, epithelial cells, liver cells, hepatocytes, neurons, fibroblasts, and/or CNS cells.

In some cases, when a regulatory element is homologous to any of SEQ ID NOs: 13-17 and 22-41, such regulatory element results in higher expression of an operably linked transgene (even when no other promoter is present in the expression vector or cassette), as compared to a similar vector without the regulatory element. Such higher expression of a transgene can be observed, e.g., in expression in HEK293T or CHO cells. In some cases, such higher expression of a transgene can be observed in a plurality of cell types, e.g., two or more mammalian cell lines, human cell lines, kidney cells, epithelial cells, liver cells, hepatocytes, neurons, fibroblasts, and/or CNS cells.

A regulatory element of the disclosure can also be a functional fragment of any of the above, e.g., a fragment of SEQ ID NOs: 1-2, 13-17, and 22-41, or any combination thereof. Such a functional fragment also increases expression of a transgene in an expression cassette or vector when compared to a similar expression cassette or vector without the regulatory element. When the functional fragment is an enhancer, intronic sequence, a promoter sequence, or a combination thereof, higher expression is observed when the fragment is operably linked to a transgene, as compared to a similar vector or cassette without the functional fragment. A fragment is preferably less than or equal to 25 bp, 30 bp, 40 bp, 50 bp, 60 bp, 70 bp, 80 bp, 90 bp, 100 bp, or 110 bp in length. In some cases, a RE of this disclosure derived from a human promoter sequence can increase expression of an operably linked transgene without the need for a second promoter in an expression cassette or vector. In some cases, a promoter in a conventional expression cassette or vector can be replaced with one or more SEQ ID NOs: 13-17 and 22-41, a combination thereof, or a sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity (e.g., as measured by BLAST) to SEQ ID NOs: 13-17 and 22-41, or a combination thereof.

In some embodiments, a regulatory element is any one of: (i) SEQ ID NO: 1, 2, 3, 4, 13, 14, 15, 16, 17, 22, 23, 24, 25, 26, 27, 28, 29, 30, 31, 32, 33, 34, 35, 36, 37, 38, 39, 40, 41, (ii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SEQ ID NO: 1, 2, 3, 4, 13, 14, 15, 16, 17, 22, 23, 24, 25, 26, 27, 28, 29, 30, 31, 32, 33, 34, 35, 36, 37, 38, 39, 40, 41, (iii) a functional fragment of any sequence of (i) or (ii), or (iv) a combination of any sequence of (i), (ii) and (iii). In some embodiments, two or more copies of a regulatory element are used to enhance transgene expression, e.g., two or more copies of one or more of SEQ ID NOs: 1-2, 13-17, and 22-41. In some embodiments, a combination of SEQ ID NOs: 1 and 2, or a combination of functional fragments thereof, is used as a regulatory element to increase transgene expression. In other embodiments, one or more of SEQ ID NO: 1 and/or 2 are coupled or operably linked to another regulatory element, such as a promoter or enhancer, to increase transgene expression. In other embodiments, one or more of SEQ ID NO: 1 and/or 2 are coupled or operably linked to one or more of SEQ ID NOs: 1-2, 13-17, and 22-41 to increase transgene expression. In some embodiments, a regulatory element that is an intronic sequence can increase transgene expression when the regulatory element is coupled or operably linked to any promoter. In some cases, a regulatory element that is derived from a human promoter sequence can increase transgene expression when the regulatory element is coupled or operably linked to a transgene without any other promoter sequences. In some cases, a regulatory element comprising a human-derived promoter sequence and an intronic sequence can increase transgene expression when the combined regulatory element is coupled or operably linked to a transgene without any other promoter sequences.

In some embodiments, one can enhance any gene therapy or known gene therapy by adding one or more regulatory elements (e.g., SEQ ID NOs: 1-2, 13-17, and 22-41) as disclosed herein to improve or increase transgene expression from the gene therapy.

In some instances, a regulatory element contains a human-derived sequence and a non-human-derived sequence such that overall the regulatory element has low sequence identity to the human genome. However a part of the regulatory element has 100% sequence identity to the human genome. In other instances, at least 50%, 60%, 70%, 80%, 90%, 95%, 98% or 99% of the regulatory element sequence is human-derived or at least 10, 20, 30, 40, or 50 contiguous nucleotides are human-derived. For example, a regulatory element can have 50% of its sequence be human-derived, and the remaining 50% be non-human-derived (e.g., mouse derived, virus derived or fully synthetic).

An increase in expression can occur at the transcriptional or posttranscriptional level. For example, at the transcriptional level, a regulatory element can increase expression by recruiting transcription factors, and/or RNA polymerase, increasing initiation of transcription or recruiting DNA and/or histone modifications that increase the level of transcription. Such increases of expression can be detected by measuring an increase in the amount of RNA transcripts that are representative of the transgene. At the posttranscriptional level, a regulatory element can increase expression by increasing the amount of protein that is translated into protein. This can be achieved through various mechanisms, for example, by increasing the stability of the mRNA or increasing recruitment and assembly of proteins required for translation. Such increase of expression can be detected by measuring the amount of protein expressed that is representative of the transgene. The amount of protein produced can be measured directly, for example by an enzyme linked immunosorbent assay (ELISA), or indirectly, for example, by a functional assay. A protein commonly measured in a functional assay is luciferase. However, other proteins such as Factor VIII can also be measured by functional assays. Preferably, the regulatory elements herein increase expression of a gene, a transgene, or a therapeutic transgene of an expression vector or cassette by at least 1.4, 1.5, 1.6, 1.7, 1.8, 1.9, 2, 2.5, 3, 3.5, 4, 5, 6, 7, 8, 9, or 10 fold, or more than 5 fold, or more than 10 fold, as compared to expression of the transgene using the same expression vector minus the regulatory element. In some cases, the regulatory elements herein increase expression of a gene, a transgene, or a therapeutic transgene of an expression vector or cassette by at least 1.5 fold, at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 50 fold, at least 100 fold, at least 200 fold, at least 300 fold, at least 400 fold, at least 500 fold, at least 600 fold, at least 700 fold, at least 800 fold, at least 900 fold, or at least 1000 fold as compared to expression of the transgene using the same expression vector minus the regulatory element. Such expression vectors or cassettes can include a promoter, separate from the regulatory element. Examples of promoters include: a min CMV promoter, a super core promoter (SCP), a TTR promoter, a Proto 1 promoter, a UCL-HLP promoter, an AAT promoter, a KAR promoter, an EF1α promoter, and an EFS promoter. In some cases, an expression vector or cassette comprising one or more of SEQ ID NOs: 13-17 and 22-41 operably linked to a transgene does not need a separate promoter for transgene expression.

In some instances, expression of a transgene operably linked to any of the regulatory elements herein together with a min CMV promoter is higher than expression of the transgene linked to a min CMV promoter without the regulatory element described herein. In some cases, expression of the transgene when linked to a min CMV promoter and a regulatory element as described herein is higher than expression of the transgene when linked, without the regulatory element, to any one of the following promoters: a super core promoter, a TTR promoter, a Proto 1 promoter, a UCL-HLP promoter, an AAT promoter, a KAR promoter, an EF1α promoter, or an EFS promoter.

In some instances, expression of a transgene operably linked to any of the regulatory elements herein (e.g., SEQ ID NOs: 1-2, 13-17, and 22-41) is higher than the expression of the transgene when linked to a UCL-HLP promoter.

Figure 1B:
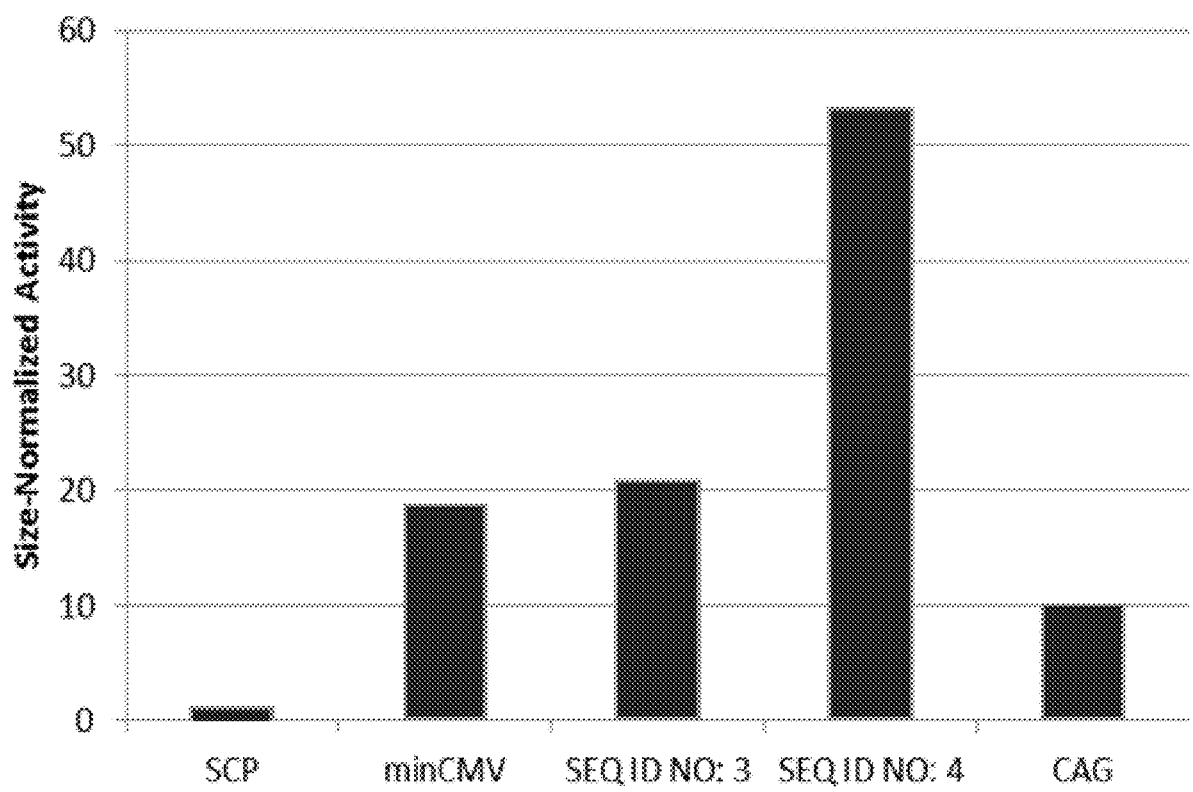
FIG. 1B illustrates the size-normalized activity (calculated by dividing the normalized luciferase activity by the length of the regulatory element in base pairs) of each regulatory element (e.g., SEQ ID NO: 3 and SEQ ID NO: 4) as compared to SCP, min CMV, and CAG in HEK293T cells. SEQ ID NO: 4 (comprising SEQ ID NO: 2 linked to a min CMV promoter) resulted in size-normalized activity at a level about 3.5 fold higher than the min CMV promoter alone and about 140 fold higher than a SCP promoter.

In some instances, the regulatory elements described herein drive high expression relative to their length. For example, a regulatory element of this disclosure that is half the length of a CMV promoter drives expression that is more than half the level of the CMV promoter. In some cases, a regulatory element is defined by the activity (or transgene expression) per base pair, or referred to as size-normalized activity. For example, a regulatory element which drives the same level of expression as a CMV promoter, but which is half the length of the CMV promoter has twice the activity per base pair. As shown in FIG. 1A, SEQ ID NO: 3 (SEQ ID NO: 1 combined with a min CMV promoter) results in a normalized luciferase value of 5552, which yields a size-normalized activity value of ~21 as shown in FIG. 1B (SEQ ID NO: 3 is 266 bp). SEQ ID NO: 4 (SEQ ID NO: 2 combined with a min CMV promoter) results in a size normalized value of 53. The min CMV promoter alone yields a size normalized value of 19, and the SCP promoter and CAG promoter yield size normalized values of 1 and 10, respectively, as shown in FIG. 1B.

Expression, high gene expression, in particular, can be measured using any technique known in the art. In some instances, the relative and higher expression of a transgene when controlled by a regulatory element of the disclosure is measured using RNA quantification/sequencing techniques, such as quantitative PCR, northern blotting, or next generation sequencing.

In some instances, high expression can be measured by the concentration of the protein produced/expressed from the transgene/gene of interest. The concentration of the protein can be measured by any method known in the art. Non-limiting examples of methods for measuring protein expression include, but not limited to, ELISA, radioimmunoassay, western blotting, or high performance liquid chromatography. See, for examples, Noble J E, *Quantification of protein concentration using UV absorbance and Coomassie dyes*, Methods Enzymol. 2014; 536:17-26; Kurien B T, Scofield R H. *A brief review of other notable protein detection methods on acrylamide gels*, Methods Mol Biol. 2012; 869:617-20; and Daniel M. Bollag, Michael D. Rozycki and Stuart J. Edelstein, *Protein Methods*, 2 ed., Wiley Publishers (1996). Protein expression can be measured in vitro or in vivo.

In various embodiments, transgene expression can be determined by measuring the amount of mRNA or RNA transcripts produced from the transgene using a PCR method. In some cases, transgene gene expression can be measured by using a protein or an immunoassay that interacts with the gene product. In some cases, Northern blot analysis and/or in situ hybridization can also be used to analyze transgene expression in vivo. The level of the protein expressed (e.g., fluorescence from a fluorescent reporter transgene) from the transgene can also be monitored to determine an increase in transgene expression in terms of transcription as well as an increase in protein synthesis (i.e., translation) in a cell or in vivo. Protein levels can also be assayed using various methods, including, but not limited to, Western blot analysis, immunohistochemistry, immunofluorescence histochemistry, and/or ELISA assays.

In some examples, a regulatory element of this disclosure results in expression of an operably linked transgene at a level of at least 0.5, 1.0, 1.1, 1.2, 1.3, 1.4, 1.5, 1.6, 1.7, 1.8, 1.9, 2.0, 2.5, or 3 IU/ml in a relevant cell type as measured by ELISA. Examples of relevant cell types include, but are not limited to, hepatocytes, liver cells, muscle cells, lung cells, epithelial cells, and kidney cells, e.g., 293T and CHO cells. In some embodiments, a regulatory element's ability to increase transgene expression can be assessed in a mouse wherein the total amount of transgene expression in the whole mouse and/or the total number of cell types or tissue types having transgene expression are measured. In some cases, a regulatory element of the disclosure can result in expression of an operably linked transgene at an overall level of at least 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, or 3.0 IU/ml in the blood of a mouse or other organism, as measured by ELISA.

When assessing the activity of an expression cassette or vector, the activity or expression can be represented as an activity or expression level per unit dose, or normalized to a dose of expression cassette or vector administered or delivered into a cell or mouse. In some embodiments, expression or activity of a transgene is normalized to an amount of plasmid or DNA (e.g., μg/kg per mouse), or viral particles (e.g., normalized to an amount of genome copies/kg per mouse) used to allow comparison across different expression vectors or cassettes with or without a regulatory element. For example, when assessing a regulatory element's activity in a mouse, expression or activity assayed can be normalized to a dose of about 5, 6, 7, 8, 9, 10, 11, 12, 13, 14, 15, 16, 17, 18, 19, 20, or greater than 10 or 20 μg of expression vector, cassette, or plasmid per mouse. In some embodiments, the expression level or activity can be normalized to $10^{10}$, $10^{11}$, $10^{12}$, $10^{13}$, $10^{14}$, or $10^{15}$ gc/kg of viral particles containing an expression vector or cassette as disclosed herein per mouse.

In other examples, expression of the linked transgene is measured by a functional assay for the activity of the expressed protein. Examples of functional assays include a luciferase assay for quantifying luciferase activity and the Coatest assay for quantifying Factor VIII activity. In the Coatest assay, expression of active Factor VIII, a co-factor, facilitates a reaction that releases a chromophoric group, pNA. The color associated with the chromophoric group released is read photometrically at 405 nm, and the intensity of the color is proportional to the amount of Factor VIII activity. Factor VIII activity can be measured as a percentage of the activity level shown by blood plasma containing 1.0 IU/mL of Factor VIII. A regulatory element of this disclosure, e.g., SEQ ID NO: 1 or 2, operably linked to min CMV and Factor VIII can result in Factor VIII activity level of more than 10%, 20%, 30%, 40%, 50%, 60%, 70%, 80%, 90%, 100%, 110%, 120%, 130%, 140%, 150%, 160%, 170%, 180%, 190%, 200%, 250% or more than 250% of the activity level as compared to a similar expression vector without the regulatory element, such as UCL-HLP without the regulatory element, when the protein is at a concentration of 1.0 IU/mL. In some cases, a regulatory element of this disclosure, e.g., SEQ ID NO: 13, 14, 15, 16, 17, 22, 23, 24, 25, 26, 27, 28, 29, 30, 31, 32, 33, 34, 35, 36, 37, 38, 39, 40, 41, operably linked to Factor VIII can result in Factor VIII activity level of more than 10%, 20%, 30%, 40%, 50%, 60%, 70%, 80%, 90%, 100%, 110%, 120%, 130%, 140%, 150%, 160%, 170%, 180%, 190%, 200%, 250% or more than 250% of the activity level as compared to a similar expression vector with a UCL-HLP promoter, e.g., when the protein is at a concentration of 1.0 IU/mL.

The regulatory elements disclosed herein can drive or increase expression of a transgene in one or more different cell types. When a regulatory element is capable of increasing expression of a transgene in multiple cell types, such expression is deemed global expression. Global expression does not require expression of a transgene in every cell of an organism. Global regulatory elements can express a transgene at similar levels in different expressing cell types, or at a range of expression levels in different cell types. In some cases, global regulatory elements can drive or increase expression of a transgene in at least two, three, four, five, ten, fifteen, or twenty different cell types. For example, a regulatory element with global expression can drive or increase expression of a transgene in at least 2, 3, 4, 5, 6, 7, 8, 9, 10, 11, or 12 different cell lines. Examples of cell lines include 293 cells, CHO cells, cancer cell lines, and immortalized cell lines. In some instances, a regulatory element drives or increases expression of a transgene in one or more cell types in an animal in vivo.

In some embodiments, a regulatory element herein drives expression of a gene in liver cells. In some embodiments, a regulatory element drives expression of a gene in any one or more of the following cell types: alveolar cells, cardiomyocytes, epithelial cells, hepatocytes, kidney cells, intestinal cells, myocytes, neurons, ovarian cells, and renal cells. In some embodiments, a regulatory element drives expression of a gene in any one or more of the following cell lines: Chinese hamster ovary cells (CHO), mouse myeloma cells (NSO), baby hamster kidney cells (BHK), B16 melanoma cells, HEK293T cells, HeLa cells, HT-1080 cells, and PER.C5 cells. In some instances, the regulatory elements drive expression of a gene in a cell line ex vivo or in vitro.

The regulatory elements of this disclosure can be combined together or combined with other regulatory elements. Such other regulatory elements include, for examples, a constitutive promoter, an inducible promoter, a repressor, an enhancer or a posttranscriptional stability element. In one embodiment, a vector comprises regulatory element of SEQ ID NO: 3, comprising SEQ ID NO: 1 and a min CMV promoter, upstream of a linked transgene. Examples of promoters contemplated herein include: min CMV promoter, super core promoter, TTR promoter, Proto 1 promoter, UCL-HLP promoter, CMVe enhancer/CMV promoter combination, AAT promoter, KAR promoter, EF1α promoter, EFS promoter, or CBA promoter.

The combined regulatory elements of this disclosure can still be short. The combined regulatory elements can have a total length of about 50 to 500, 100 to 400, 50 to 200, 100 to 200, or 150 to 300 base pairs in length. The combined regulatory elements can have a combined length of less than about 500, 450, 400, 350, 300, 250, 200, 150 or 100 base pairs in length. In some embodiments, the regulatory element is 40-50 bp, 45-50, 49, 50-60, 56, 50-55, or 45-60 bp.

The combined regulatory elements can come from different species. In preferred examples, at least one part of a combined regulatory element is human-derived. Non-human-derived elements can be derived from mammalian, viral, or synthetic sequences.

Expression Cassettes

The terms "expression cassette" and "nucleic acid cassette" are used interchangeably to refer to a polynucleotide molecule or a nucleic acid sequence. In some cases, an expression cassette comprises one or more regulatory elements disclosed herein operably linked to a transgene. In some cases, an expression cassette comprises one or more regulatory elements. In some cases, the expression cassette further comprises a promoter. In some cases, an expression cassette comprises one or more sequences of SEQ ID NOs: 1-2, 13-17, and 22-41 and/or any combination thereof. In some cases, an expression cassette comprises one or more of SEQ ID NOs: 1-2, 13-17, and 22-41, (ii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SEQ ID NOs: 1-2, 13-17, and 22-41, (iii) a functional fragment of any sequence of (i) or (ii), or (iv) a combination of any sequence of (i), (ii) and/or (iii). In some cases, sequence identity is measured by BLAST. In some cases, a regulatory element is located upstream of a transgene in an expression cassette. In some cases, a regulatory element is located downstream of a transgene in an expression cassette.

In some aspects, one or more regulatory elements described herein (e.g., SEQ ID NOs: 1-2, 13-17, and 22-41) are operably linked to a transgene (e.g., a reporter gene or a therapeutic transgene) in an expression cassette. In some cases, a gene therapy comprises an expression cassette comprising a transgene operably linked to one or more, two or more, three or more, four or more, or five or more regulatory elements of the present disclosure to result in increased expression of a transgene, e.g., a reporter gene, eGFP, RFP, Factor VIII, Cas9, DNA binding protein, hormone, growth or differentiation factor, insulin, growth hormone, VEGF, neurotrophic factor, fibroblast epithelial factor; cytokine, interleukin, lymphokine, tumor necrosis factor, antibody, immunoglobulin, interferon, chimeric T cell receptor; lipoprotein receptor, cystic fibrosis transmembrane regulator, a gene associated with mucopolysaccharidosis type I, II, III, or IV, beta globin or lipoprotein lipase, or a variant or fragment thereof. In some cases, the transgene is ATP7A, ATP7B, ATP8B1, ABCB4, ABCB11, or a variant or functional fragment thereof, or sequences having at least 80%, at least 85%, at least 90%, at least 95%, or at least 99% sequence identity thereto. In some cases, the transgene is CDKL5, CNTNAP2, ZEB2, or a variant or functional fragment thereof, or sequences having at least 80%, at least 85%, at least 90%, at least 95%, or at least 99% sequence identity thereto. In some cases, the transgene is a fibrinogen, prothrombin, a coagulation factor, or a blood clotting factor (e.g., Factor 1, 2, 3, 4, 5, 6, 7, 8, 9, 10, 11, or 12), or a variant or functional fragment thereof.

In some cases, an expression cassette is adapted for delivery via gene therapy. In some cases, an expression cassette is a linear or a circular construct. In some cases, an expression cassette is part of a plasmid, vector, a viral vector, or rAAV. In some cases, an expression cassette comprising one or more REs of this disclosure operably linked to a transgene is adapted for expression in a plurality of cells, e.g., in any mammalian or human cell line, kidney cells, epithelial cells, liver cells, hepatocytes, neurons, fibroblasts, and/or CNS cells. In some cases, an expression cassette comprising one or more REs of this disclosure (e.g., SEQ ID NOs: 1-2, 13-17, and 22-41) operably linked to a transgene is adapted for expression in 2 or more, 3 or more, 4 or more, or 5 or more mammalian or human cell lines or cell types. In some cases, transgene expression occurs in 2 or more, 3 or more, 4 or more, or 5 or more of the following cell types: kidney cells, epithelial cells, hepatocytes, neurons, fibroblasts, cardiomyocytes, CNS cells, muscle cells, blood cells, and/or stem cells.

In some cases, an expression cassette comprising one or more REs of this disclosure (e.g., SEQ ID NOs: 1-2, 13-17, and 22-41) operably linked to a transgene is adapted for transgene expression in the liver or in hepatocytes. In some cases, an expression cassette comprising one or more REs of this disclosure operably linked to a transgene is adapted for systemic delivery of a transgene, e.g., via oral, intravenous, intramuscular, intraperitoneal, intrathecal, enteral, or parenteral administration. In some cases, systemic delivery of a transgene involves increased transgene expression in the liver or in hepatocytes. In some cases, an expression cassette comprising one or more REs of this disclosure operably linked to a transgene results in expression of the transgene in hepatocytes at a level that is at least 1.5 fold, at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 50 fold, at least 100 fold, at least 200 fold, at least 300 fold, at least 400 fold, at least 500 fold, at least 600 fold, at least 700 fold, at least 800 fold, at least 900 fold, or at least 1000 fold as compared to an expression cassette without the REs, or as compared to a control (e.g., a vector alone control, buffer control, or a sequence that does not have any expression activity). In some cases, the expression driven by a relatively short RE is compared to that of a constitutive promoter, a CMV promoter, super core promoter, TTR promoter, Proto 1 promoter, UCL-HLP promoter, or CMVe promoter operably linked to the same transgene.

In some cases, an expression cassette comprising a regulatory element of this disclosure results in high or increased expression of an operably linked transgene, wherein the high or increased expression is determined as compared to a control, e.g., a constitutive promoter, a CMV promoter, super core promoter (SCP), TTR promoter, Proto 1 promoter, UCL-HLP promoter, or CMVe promoter. Other controls that can be used for comparison to determine high or increased transgene expression include buffer alone, min CMV, EFS, vector alone, or a sequence known to have no expression activity. In some cases, CAG or SEQ ID NO: 4 is used as a positive control for comparing expression level and/or size-normalized activity.

Expression of a transgene or gene of interest can occur via an expression vector or expression cassette. Such expression vector or cassette can include any one or more of the following additional elements promoters, enhancers, or post-transcriptional regulatory elements. The regulatory elements of this disclosure can be positioned upstream or downstream of the transgene, and can be transcribed or not transcribed. In some examples, the regulatory elements of this disclosure are positioned downstream of a promoter and upstream of the transgene. In some examples, the regulatory elements are positioned as promoters of the transgene. In some cases, one or more REs of this disclosure are operably linked to a transgene without any other promoter in an expression vector or cassette.

Expression vectors or cassettes can be circular or linear nucleic acid molecules. In some cases, a vector or cassette is delivered to cells (e.g., a plurality of different cells or cell types, including target cells or cell types and/or non-target cells or cell types). A vector or cassette can be an integrating or non-integrating vector, referring to the ability of the vector or cassette to integrate the expression vector or cassette, in part or whole, and/or the transgene into a genome of a cell. Either an integrating vector or a non-integrating vector can be used to deliver a transgene operably linked to a regulatory element. Examples of vectors or cassettes include, but are not limited to, (a) non-viral vectors such as nucleic acid vectors including linear oligonucleotides and circular plasmids; artificial chromosomes such as human artificial chromosomes (HACs), yeast artificial chromosomes (YACs), and bacterial artificial chromosomes (BACs or PACs)); episomal vectors; transposons (e.g., PiggyBac); and (b) viral vectors such as retroviral vectors, lentiviral vectors, adenoviral vectors, and adeno-associated viral vectors (AAVs). Viruses have several advantages for delivery of nucleic acids, including high infectivity. In some embodiments, a virus is used to deliver a nucleic acid molecule or expression cassette comprising one or more regulatory elements, as described herein, operably linked to a transgene.

The vectors described herein can be delivered to a cell of interest either directly or via a delivery system. Examples of delivery systems include, but are not limited to, viral vectors (e.g., retroviral, adenoviral, adeno-associated (AAV), helper-dependent adenoviral systems, hybrid adenoviral systems, herpes simplex, pox virus, lentivirus, and Epstein-Barr virus), physical systems (naked DNA, DNA bombardment, electroporation, hydrodynamic, ultrasound, and magnetofection), and chemical systems (cationic lipids, different cationic polymers, and lipid polymers).

Any known technique can be used to deliver the regulatory element(s) and an operably linked transgene, or compositions comprising regulatory elements and a transgene, to the cells of interest to confer or induce in vitro, in vivo, or ex vivo expression of the transgene in a cell-type, tissue or organism of interest.

Preferred characteristics of viral gene therapy vectors or gene delivery vectors include the ability to be reproducibly and stably propagated and purified to high titers; to mediate targeted delivery (e.g., to deliver the transgene specifically to the tissue or organ of interest without widespread vector dissemination elsewhere); and to mediate gene delivery and transgene expression without inducing harmful side effects.

Several types of viruses, for example, the non-pathogenic parvovirus, adeno-associated virus, have been engineered for the purposes of gene delivery. Virus-based vectors for various gene-therapy applications can harness the viral infection pathway but avoid the subsequent expression of viral genes that can lead to replication and toxicity. Such virus-based vectors can be obtained by deleting all, or some, of the coding regions from the viral genome, but leaving intact those sequences (e.g., terminal repeat sequences) that are necessary for functions such as packaging the expression vector into the virus capsid or the integration of vector nucleic acid or heterologous gene or DNA into the host genome. An expression vector or cassette comprising a transgene, for example, can be cloned into a viral backbone such as a modified or engineered viral backbone lacking viral genes, and used in conjunction with additional vectors (e.g., packaging vectors), which can, for example, when co-transfected, produce recombinant viral vector particles.

Several serotypes of AAV, a non-pathogenic parvovirus, have been engineered for the purposes of gene delivery, some of which are known to have tropism for certain tissues or cell types. Viruses used for various gene-therapy applications can be engineered to be replication-deficient or to have low toxicity and low pathogenicity in a subject or a host. Such virus-based vectors can be obtained by deleting all, or some, of the coding regions from the viral genome, and leaving intact those sequences (e.g., inverted terminal repeat sequences) that are necessary for functions such as packaging the vector genome into the virus capsid or the integration of vector nucleic acid (e.g., heterologous DNA sequence) into the host genome. An expression vector or cassette comprising a transgene, for example, can be cloned into a viral backbone such as a modified or engineered viral backbone lacking viral genes, and used in conjunction with additional vectors (e.g., packaging vectors), which can, for example, when co-transfected, produce recombinant viral vector particles.

In some embodiments, an AAV vector or an AAV viral particle, or virion, that is used to deliver one or more regulatory elements and a transgene into a cell, cell type, or tissue, in vivo, ex vivo, or in vitro, is preferably replication-deficient. In some embodiments, an AAV virus is engineered or genetically modified so that it can replicate and generate virions only in the presence of helper factors.

In some embodiments, the expression vector or cassette is designed for delivery by an AAV, or a recombinant AAV (rAAV). In some embodiments, an expression vector or cassette is delivered using a lentivirus or a lentiviral vector. In some embodiments, larger transgenes, i.e., genes that exceed the cloning capacity of an AAV, are preferably delivered using a lentivirus or a lentiviral vector.

The expression vector or cassette can be designed for delivery by an AAV. The AAV can be any serotype, for examples, AAV1, AAV2, AAV3, AAV3b, AAV4, AAV5, AAV6, AAV7, AAV8, AAV9, AAV10, AAV11, AAV12, AAV-DJ, or a chimeric, hybrid, or variant AAV. The AAV can also be a self-complementary AAV (scAAV). An expression vector or cassette designed for delivery by an AAV can comprise a 5' ITR, one or more regulatory elements, an optional minimal promoter, a transgene, optionally one or more introns, an optional polyA signal, and a 3' ITR. In some instances an expression vector or cassette also contains one or more post-transcriptional RNA regulatory elements.

Figure 6A:
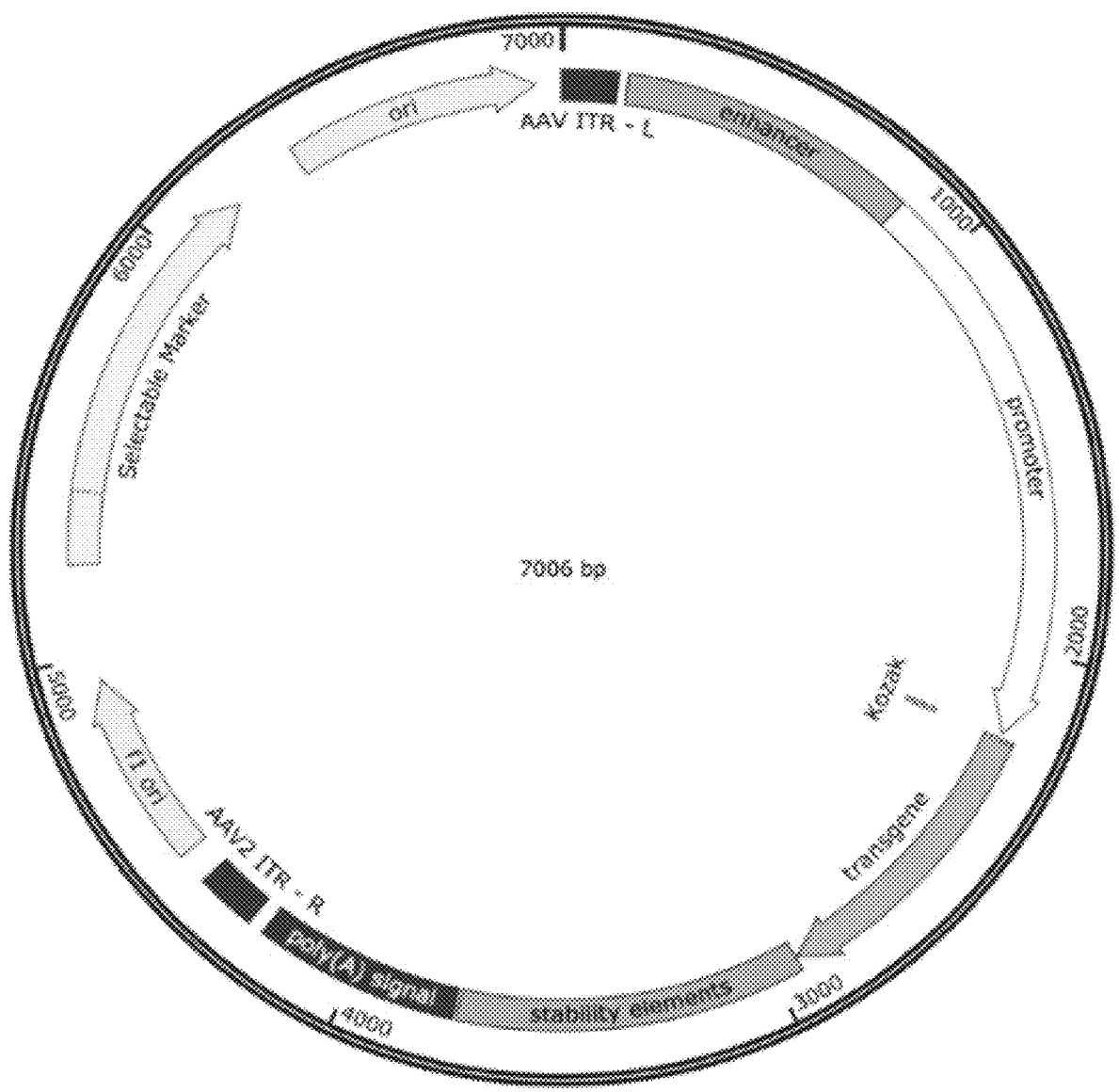
FIG. 6A illustrate an exemplary expression cassette, vector, or plasmid of this disclosure, comprising AAV ITR-L and ITR-R and one or more regulatory elements, e.g., an enhancer, a promoter, stability elements, and polyA signal, operably linked to a transgene. Such rAAV vector can be used for gene therapy.
Figure 6B:
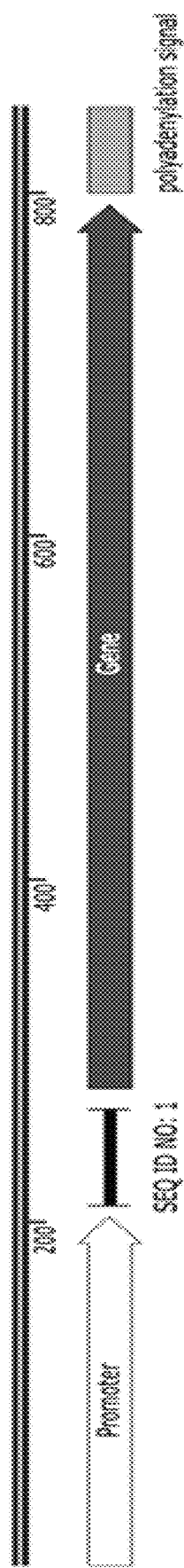
FIG. 6B illustrates a close-up view of an expression cassette wherein regulatory element SEQ ID NO: 1 is operably linked to a transgene, and wherein the regulatory element is located downstream of a promoter and upstream of the gene and a polyadenylation signal.
Figure 6C:
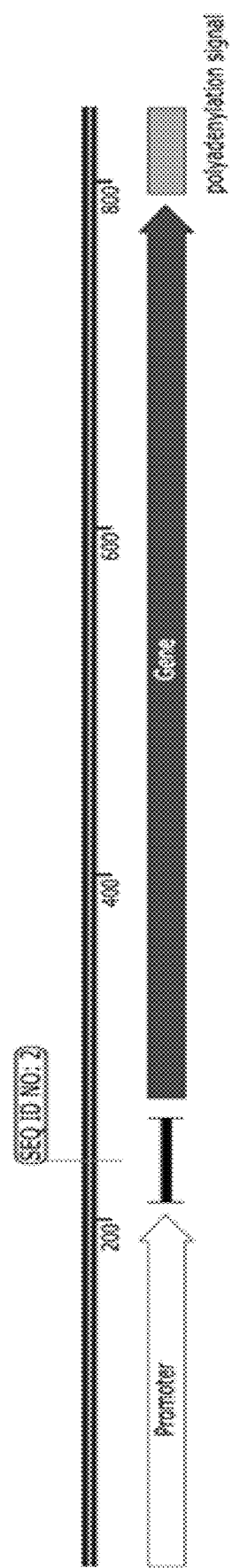
FIG. 6C illustrates an expression cassette wherein regulatory element SEQ ID NO: 2 is operably linked to a transgene, and wherein the regulatory element is located downstream of a promoter and upstream of the gene and a polyadenylation signal.
Figure 7:
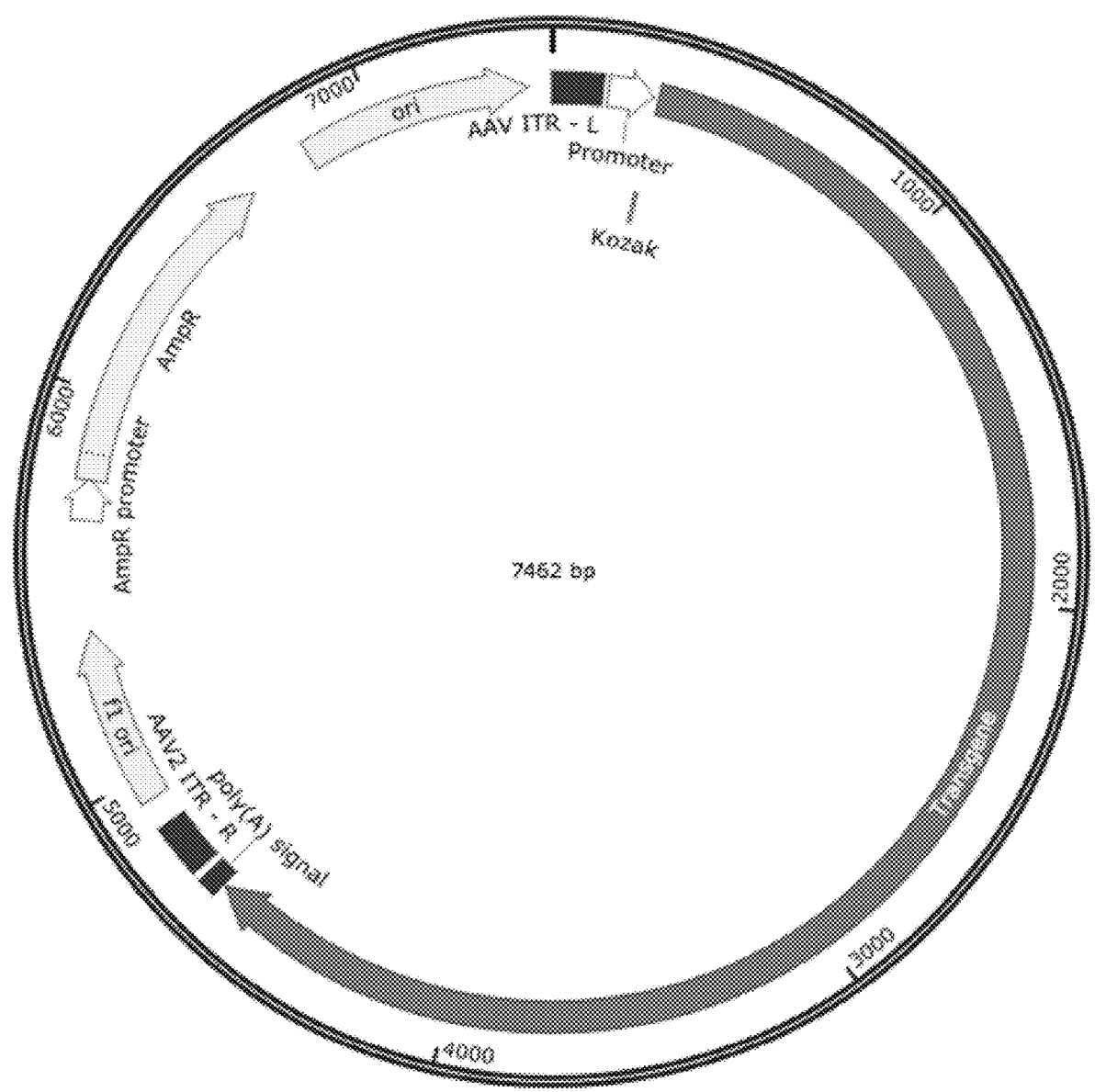
FIG. 7 illustrates an exemplary expression cassette, vector, or plasmid of this disclosure, comprising AAV ITR-L and ITR-R and one or more relatively short human-derived regulatory elements of this disclosure (e.g., SEQ ID NOs: 13-17 and 22-41) operably linked to a large transgene, wherein the transgene is at least 3 kb or 3-5 kb in size. Such rAAV vector can be used for a gene therapy treatment.

Exemplary expression vectors or cassettes containing SEQ ID NO: 1 or SEQ ID NO: 2 are shown in FIG. 6B and FIG. 6C, respectively. An exemplary expression vector which could contain any one or more of SEQ ID NOs: 13-17 and 22-41 in the promoter position is shown in FIG. 7. Such expression vectors or cassettes can be adapted for transgene expression using any one of the delivery systems or gene therapy described herein, including, but not limited to, an AAV, lentivirus, adenovirus, or retrovirus.

The expression vector or cassette can be designed for delivery by an optimized therapeutic retroviral vector. The retroviral vector can be a lentivirus comprising a left (5') LTR; sequences which aid packaging and/or nuclear import of the virus, at least one nucleic acid cell-type selective regulatory element, optionally a lentiviral reverse response element (RRE); optionally a promoter or active portion thereof; a therapeutic transgene operably linked to the various regulatory elements; optionally an insulator; and a right (3') retroviral LTR.

In some embodiments, the expression vector or cassette comprises one or more regulatory elements. In some examples, the vector or cassette contains two or more regulatory elements combined. In some examples, the vector or cassette contain two or more regulatory elements which are not combined, for example, a promoter upstream of the transgene and an enhancer located downstream of the transgene. In some embodiments, an intron sequence is located downstream of a promoter.

In some cases, the expression vector or cassette contains a high driver regulatory element, a global regulatory element, or a short regulatory element. In some cases, the high driver regulatory element drives global expression and/or is short. In some cases, the regulatory element is a short global regulatory element. In some embodiments, the expression vector or cassette containing a regulatory element is used in a viral vector, or is packaged in a virus, which can be used to infect an animal model in vivo or to transfect cells ex vivo or in vitro to assess the activity of the regulatory element in the animal model as a whole or in certain cell types, or a target cell type.

In some embodiments, expression cassettes containing regulatory elements of this disclosure also comprise one or more transgenes. The transgenes can be protein-coding genes. In some cases, the expression cassette contains a therapeutic transgene. The therapeutic transgene can replace an absent or defective gene, or compensate for deficient expression of a protein. The therapeutic transgene can be involved in a cell signaling pathway. In some cases, the expression vector or cassette contains a transgene for commercial production. In some embodiments, the transgene for commercial production can produce a therapeutic protein, or improve a function of a host cell, or restore or rescue a phenotype of a host cell.

The regulatory elements disclosed herein can be located at any position within an expression vector or cassette. For example, the regulatory elements can be positioned upstream of an enhancer, downstream of an enhancer but upstream of a promoter, within the 5' UTR of a transgene, within an intron within the transgene, in the 3' UTR of the transgene, or downstream of the transgene. In some cases, one or more regulatory elements are positioned upstream or downstream of the operably linked transgene. For example, SEQ ID NO: 3 and 4 contain the sequences of SEQ ID NO: 1 and 2, respectively, downstream of a min CMV promoter. Regulatory elements can have different effects on transgene expression from different locations within an expression cassette or vector. Each regulatory element can have a preferred location within the expression vector or cassette which results in optimal expression from that regulatory element.

Utilizing shorter regulatory elements with high activity can allow for delivery of a larger transgene within the same packaging capacity and without sacrificing transgene expression or high expression. In some cases, use of a shorter regulatory element allows for delivery of two or more transgenes in a single vector, or delivery of a large transgene at relatively higher levels of expression as compared to a similar vector or cassette without the regulatory element. The two or more transgenes can comprise two or more different protein-coding genes or a protein-coding gene and a non-coding element. In one example, a vector comprises a Cas9 coding sequence and one or more guide RNAs, as described in Example 4. In some cases, the regulatory elements are about 20 to 100, 30 to 100, 40 to 80, or 50 to 60 base pairs in length. In some cases, the regulatory elements are less than 150, 120, 110, 100, 90, 80, 70, or 60 base pairs in length. The combined regulatory elements of this disclosure can be short. The combined regulatory elements can have a total length of about 50 to 500, 100 to 400, 50 to 200, 100 to 200, or 150 to 300 base pairs in length. The combined regulatory elements can have a combined length of less than about 500, 450, 400, 350, 300, 250, 200, 150, or 100 base pairs in length.

In some cases, an expression cassette or vector comprises one or more REs of this disclosure operably linked to a large transgene whose sequence is more than 1 kb, 1.5 kb, 2 kb, 2.5 kb, 3 kb, 3.5 kb, 4 kb, 4.5 kb, 5 kb, 5.5 kb, 6 kb, 6.5 kb, 7 kb, or 7.5 kb. In some cases, a large transgene is operably linked to one or more REs, wherein each RE is no more than 49 bp, 50 bp, 56 bp, 60 bp, 70 bp, 80 bp, 90 bp, 100 bp, 110 bp, 117 bp, 120 bp, 130 bp, 140 bp, 150 bp, 160 bp, 170 bp, 180 bp, 190 bp, 200 bp, 210 bp, 220 bp, 230 bp, 240 bp, 250 bp, 259 bp, 260 bp, 265 bp, 270 bp, 280 bp, 290 bp, 300 bp, 310 bp, 320 bp, 330 bp, 340 bp, 350 bp, 360 bp, 370 bp, 380 bp, 390 bp, or 400 bp, and comprises a sequence according to any one of TABLE 1 or SEQ ID NOs: 1-2, 13-17, and 22-41. In some cases, the REs increase expression of the transgene by at least 1.5 fold, at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 50 fold, at least 100 fold, at least 200 fold, at least 300 fold, at least 400 fold, at least 500 fold, at least 600 fold, at least 700 fold, at least 800 fold, at least 900 fold, or at least 1000 fold as an expression vector or cassette without the REs, or as compared to a negative control (e.g., vector alone control or a vector comprising a sequence with no known expression activity).

When assessing the activity of an expression cassette or vector, the activity or expression can be represented as an activity or expression level per unit dose, or normalized to a dose of expression cassette or vector administered or delivered to a cell, mouse, or a subject. In some cases, expression or activity of a transgene is normalized to an amount of plasmid or DNA (e.g., µg/kg per mouse), or viral particles (e.g., normalized to an amount of genome copies/kg per mouse or subject) used to allow comparison across different expression vectors or cassettes with or without a regulatory element. For example, when assessing a regulatory element's activity in a mouse, transgene expression or transgene activity in cells assayed can be normalized to a dose of about 5, 6, 7, 8, 9, 10, 11, 12, 13, 14, 15, 16, 17, 18, 19, or 20 µg, or greater than 10 µg, or greater than 20 µg of expression vector, cassette, or plasmid per mouse. In some cases, the expression level or activity can be normalized to $10^{10}$, $10^{11}$, $10^{12}$, $10^{13}$, $10^{14}$, or $10^{15}$ gc/kg of viral particles containing an expression vector or cassette as disclosed herein per mouse.

One advantage of delivering expression cassettes of this disclosure using gene therapy, e.g., rAAV, is that such therapies can provide more targeted and sustained therapeutic effects over time. Additionally, viral gene therapies can be engineered to have tropism for one or more cell types or tissues of interest (e.g., hepatocytes or liver). For example, viral gene therapies can be engineered to infect and deliver a payload or a therapeutic agent, e.g., a transcriptional modulator or a transgene, to one or more regions, tissues, or cell types in vivo.

Transgenes

The constructs (e.g., expression cassette or vectors) disclosed herein can be used to drive expression of a transgene in a cell or a plurality of cells of interest. In some cases, constructs disclosed herein are used for recombinant protein expression. For example, regulatory elements disclosed herein can be used to drive expression of recombinant proteins. Recombinant proteins produced with methods of this disclosure can be produced for therapeutic purposes, research purposes, or commercial purposes. Examples of transgenes that can be expressed as part of an in vivo, ex vivo, or in vitro protein expression system include, but are not limited to: Cas9, Factor VIII, DNA binding proteins, hormones, growth/differentiation factors, e.g., insulin, growth hormone, VEGF, neurotrophic factor, fibroblast epithelial factor; therapeutic proteins that regulate or modulate the immune system, e.g., cytokines, interleukins, lymphokines, tumor necrosis factor, antibodies, immunoglobulins, interferons, chimeric T cell receptors; lipoprotein receptor; cystic fibrosis transmembrane regulator; a gene associated with mucopolysaccharidosis types I, II, III, and IV; beta globin; and lipoprotein lipase. In some cases, the transgene expressed is ATP7A, ATP7B, ATP8B1, ABCB4, ABCB11, or a variant or functional fragment thereof. In some cases, the transgene expressed is CDKL5, CNTNAP2, ZEB2, or a variant or functional fragment thereof. In some cases, the transgene is a fibrinogen, prothrombin, a coagulation factor, or a blood clotting factor (e.g., Factor 1, 2, 3, 4, 5, 6, 7, 8, 9, 10, 11, or 12), a variant or functional fragment thereof.

In some cases, an expression cassette comprising one or more REs of this disclosure operably linked to a transgene is adapted for a gene therapy treatment. In some cases, the gene therapy treatment is administered or adapted for systemic delivery, such as by intravenous infusion or injection. In some cases, the gene therapy is adapted for expression in the liver or hepatocytes. In some cases, the operably linked transgene is a gene that is expressed in the liver or in hepatocytes, or is a gene relevant in a liver disease or condition, e.g, ATP7B associated with Wilson's disease; ABCB4 associated with progressive familial intrahepatic cholestasis type 3; ALDOB associated with hereditary fructose intolerance; GBE1 associated with glycogen storage disease type IV; FAH associated with tyrosinemia type I; ASL associated with argininosuccinate lyase deficiency; SLC25A13 associated with citrin deficiency (CTLN2, NICCD); LIPA associated with cholesteryl ester storage disease; SERPINA1 associated with alpha-1 antitrypsin deficiency; CFTR associated with cystic fibrosis; HFE associated with hereditary hemochromatosis; or ALMS1 associated with Alström syndrome. In some cases, one or more regulatory elements or an expression cassette comprising a RE disclosed herein are used for a gene therapy treatment to treat an inherited liver disease, e.g., a disorder of bile acid synthesis, a disorder of carbohydrate metabolism, a disorder of amino acid metabolism, a urea cycle disorder, or a disorder of lipid metabolism. In some cases, one or more regulatory elements or an expression cassette comprising a RE disclosed herein are used for gene therapy treatment (e.g., AAV gene therapy) to treat Wilson's disease; progressive familial intrahepatic cholestasis type 3; hereditary fructose intolerance; glycogen storage disease type IV; tyrosinemia type I; argininosuccinate lyase deficiency; citrin deficiency (CTLN2, NICCD); cholesteryl ester storage disease; alpha-1 antitrypsin deficiency; cystic fibrosis; hereditary hemochromatosis; or Alström syndrome. In some cases, one or more regulatory elements or an expression cassette comprising a RE disclosed herein are used for gene therapy treatment (e.g., AAV gene therapy) to treat a blood clotting disorder (e.g., hemophilia, hemophilia A, or hemophilia B) or Wilson's disease.

In some cases, a method of expressing a recombinant protein comprises introducing an expression cassette or vector into a cell or a plurality of cells, wherein the expression cassette or vector comprises one or more REs of this disclosure (SEQ ID NOs: 1-2, 13-17, and 22-41) operably linked to a transgene. In some cases, the transgene is any one of Cas9, Factor VIII, DNA binding proteins, hormones, growth/differentiation factors, e.g., insulin, growth hormone, VEGF, neurotrophic factor, fibroblast epithelial factor; therapeutic proteins that regulate or modulate the immune system, e.g., cytokines, interleukins, lymphokines, tumor necrosis factor, antibodies, immunoglobulins, interferons, chimeric T cell receptors; lipoprotein receptor; cystic fibrosis transmembrane regulator; a gene associated with mucopolysaccharidosis types I, II, III, and IV; beta globin; and lipoprotein lipase. In some cases, the transgene expressed is ATP7A, ATP7B, ATP8B1, ABCB4, ABCB11, or a variant or fragment thereof. In some cases, the transgene expressed is CDKL5, CNTNAP2, ZEB2, or a variant or fragment thereof. In some cases, the transgene is a fibrinogen, prothrombin, a coagulation factor, or a blood clotting factor (e.g., Factor 1, 2, 3, 4, 5, 6, 7, 8, 9, 10, 11, or 12).

Nucleotide and protein sequences of human genes disclosed herein can be found in various public databases, including GenBank (NCBI) or UniProKB databases. For examples, human UniProtKB accession numbers include: Q04656 (ATP7A); P35670 (ATP7B); O43520 (AT8B1); P21439 (MDR3, also referred to as ABCB4); O95342 (ABCBB, also referred to as ABCB11); O76039 (CDKL5); Q9UHC6 (CNTP2, also referred to as CNTNAP2); O60315 (ZEB2); P12259 (F5 or Factor V); P00451 (F8 or Factor VIII); P00740 (F9 or Factor IX); P00742 (F10 or Factor X). Any one of such protein sequences can be encoded by a nucleic acid sequence (or a transgene) in an expression cassette disclosed herein.

Recombinant proteins can be produced in bacterial cells, yeast cells, insect cells, plant cells, or mammalian cells. In some examples, recombinant proteins are produced in mammalian cells. In some examples, proteins are produced in animal models. Examples of cell lines which can be used to produce proteins include Chinese hamster ovary cells (CHO), mouse myeloma cells (NSO), baby hamster kidney cells (BHK), and B16 melanoma cells. In some examples, human-derived cell lines are used. Examples of human cell lines which can be used to produce proteins include HEK293T, HeLa, HT-1080, and PER.C5. Recombinant proteins can also be produced in animals or in animal products. Recombinant proteins can also be produced in plants. Recombinant proteins may be expressed in the leaves, stems, flowers, fruits or seeds of a plant.

In some embodiments, a regulatory element of the disclosure can be used to drive or increase expression of a reporter gene, such as luciferase. In some embodiments, one or more regulatory elements can result in expression of an operably linked luciferase transgene at levels that yield an output of more than $10^{17}$, $10^{18}$, $10^{19}$, $10^{20}$, or $10^{21}$ photons/sec/mouse as measured according to the method of Example 2.

Also contemplated herein is a method of treating a haploinsufficiency or any disorder or condition associated with insufficient gene expression and/or protein activity or synthesis (or under-expression of a gene), comprising administering an expression cassette or vector in a subject in need thereof, wherein the expression cassette or vector comprises one or more REs of this disclosure (SEQ ID NOs: 1-2, 13-17, and 22-41) operably linked to a transgene. In some cases, the transgene is a DNA binding protein or a transcriptional modulator (e.g., a transcriptional activator) that results in increased expression of an endogenous gene. In some cases, the transgene in the expression cassette or vector is a therapeutic transgene. In some cases, the therapeutic transgene is any one of Cas9, Factor VIII, DNA binding proteins, hormones, growth/differentiation factors, e.g., insulin, growth hormone, VEGF, neurotrophic factor, fibroblast epithelial factor; therapeutic proteins that regulate or modulate the immune system, e.g., cytokines, interleukins, lymphokines, tumor necrosis factor, antibodies, immunoglobulins, interferons, chimeric T cell receptors; lipoprotein receptor; cystic fibrosis transmembrane regulator; a gene associated with mucopolysaccharidosis types I, II, III, and IV; beta globin; and lipoprotein lipase. In some cases, the transgene expressed is ATP7A, ATP7B, AT8B1 (or ATP8B1), MDR3 (or ABCB4), ABCBB (or ABCB11), CDKL5, CNTP2 (or CNTNAP2), ZEB2, Factor V, Factor VIII, Factor IX, or Factor X, or a variant, subunit, isoform, or functional fragment thereof. Progressive familial intrahepatic cholestasis (PFIC) includes PFIC1, PFIC2, and PFIC3, which are associated with mutation(s) in ATP8B1, ABCB11, and ABCB4 genes. Progressive familial intrahepatic cholestasis type 2 (PFIC2) is associated with a defect or a mutation in ABCB11. ATP8B1 gene mutations can cause PFIC1. Mutations in the ABCB11 gene can cause PFIC2. ABCB4 gene mutations can cause PFIC3. In some cases, a transgene disclosed herein is CDKL5 and is used in a gene therapy to treat CDKL5 deficiency disorder. A mutation or defect in CNTNAP2 can result in autism spectrum disorder. In some cases, the transgene is a fibrinogen, prothrombin, a coagulation factor, or a blood clotting factor (e.g., Factor 1, 2, 3, 4, 5, 6, 7, 8, 9, 10, 11, or 12), or a variant or functional fragment thereof. In some cases, the transgene is expressed preferentially in hepatocytes. In some cases, the administering is systemic, e.g., via oral, intravenous, intramuscular, intraperitoneal, intrathecal, enteral, or parenteral administration. In some cases, the method comprises delivering the expression cassette or vector via intravenous infusion or injection. In some cases, the administering is local, e.g., via injection into the liver, CNS, or an organ in a body. In some cases, the expression cassette or vector is an AAV, e.g., AAV8.

In some cases, a method of treating a disorder or condition associated with overexpression of a gene is contemplated herein, the method comprising administering an expression cassette or vector into a subject in need thereof, wherein the expression cassette or vector comprises one or more REs of this disclosure (SEQ ID NOs: 1-2, 13-17, and 22-41) operably linked to a transgene. In some cases, the transgene is a DNA binding protein or a transcriptional modulator (e.g., a transcriptional repressor) that results in decreased expression of an endogenous gene. In some cases, the transgene is expressed preferentially in hepatocytes. In some cases, the administering is systemic, e.g., via oral, intravenous, intramuscular, intraperitoneal, intrathecal, enteral, or parenteral administration. In some cases, the method comprises delivering the expression cassette or vector via intravenous infusion or injection. In some cases, the administering is local, e.g., via injection into the liver, CNS, or an organ in a body. In some cases, the expression cassette or vector is an AAV, e.g., AAV8.

In some cases, a method of treating a genetic disorder or condition associated with a defect in any one of the following genes is contemplated herein: ATP7A, ATP7B, AT8B1 (or ATP8B1), MDR3 (or ABCB4), ABCBB (or ABCB11), CDKL5, CNTP2 (or CNTNAP2), ZEB2, Factor V, Factor VIII, Factor IX, Factor X, a fibrinogen, prothrombin, a coagulation factor, or a blood clotting factor (e.g., Factor 1, 2, 3, 4, 5, 6, 7, 8, 9, 10, 11, or 12). In some cases, disclosed herein is a method of treating Wilson's disease. In some cases, the method of treating Wilson's disease or any other genetic disorder or condition associated with ATP7A, ATP7B, AT8B1 (or ATP8B1), MDR3 (or ABCB4), ABCBB (or ABCB11), CDKL5, CNTP2 (or CNTNAP2), ZEB2, Factor V, Factor VIII, Factor IX, Factor X, a fibrinogen, prothrombin, a coagulation factor, or a blood clotting factor (e.g., Factor 1, 2, 3, 4, 5, 6, 7, 8, 9, 10, 11, or 12) comprises administering an expression cassette or vector disclosed herein into a subject in need thereof (e.g., an animal or a human), wherein the expression cassette or vector comprises one or more REs of this disclosure operably linked to a transgene of this disclosure, e.g., ATP7A, ATP7B, AT8B1 (or ATP8B1), MDR3 (or ABCB4), ABCBB (or ABCB11), CDKL5, CNTP2 (or CNTNAP2), ZEB2, Factor V, Factor VIII, Factor IX, Factor X, a fibrinogen, prothrombin, a coagulation factor, a blood clotting factor (e.g., Factor 1, 2, 3, 4, 5, 6, 7, 8, 9, 10, 11, or 12), a DNA binding protein, or a transcriptional modulator. In some cases, the transgene is a Cas protein (e.g., Cas9 or saCas9 protein) and/or a guide RNA that edit an endogenous gene (e.g., a Cas removes a mutation from an endogenous gene). In some cases, the expression cassette or vector expresses the transgene preferentially in the liver. In some cases, the administering is systemic, e.g., via intravenous infusion or injection. In some cases, the administering is local, e.g., injection directly into a tissue or organ, e.g., injection into the liver or CNS.

In some cases, an expression cassette or vector disclosed herein is used to treat Wilson's disease, wherein the expression cassette or vector comprises one or more REs (e.g., SEQ ID NO: 1, 2, 3, 4, 13, 14, 15, 16, 17, 22, 23, 24, 25, 26, 27, 28, 29, 30, 31, 32, 33, 34, 35, 36, 37, 38, 39, 40, 41) operably linked to a therapeutic transgene, wherein the transgene is ATP7B or a transcriptional modulator or a DNA binding protein that acts on an endogenous ATP7B gene to increase ATP7B expression in a cell or in vivo. In some cases, such expression cassette or vector is delivered into a subject diagnosed with or at risk for Wilson's disease. In some cases, such expression cassette or vector is delivered into a subject via intravenous infusion or injection. In some cases, the delivery is systemic. In some cases, a method of treating Wilson's disease comprising administering a gene therapy (e.g., an AAV gene therapy) into a subject in need thereof, wherein the gene therapy comprises one or more REs (e.g., SEQ ID NO: 1, 2, 3, 4, 13, 14, 15, 16, 17, 22, 23, 24, 25, 26, 27, 28, 29, 30, 31, 32, 33, 34, 35, 36, 37, 38, 39, 40, 41) operably linked to a therapeutic transgene, wherein the transgene is ATP7B or a transcriptional modulator that acts on an endogenous ATP7B gene to increase ATP7B expression in a cell or in vivo. In some cases, the expression cassette or vector is an AAV, e.g., AAV8. In some cases, the expression cassette or vector is preferentially expressed in hepatocytes or in the liver.

In some cases, an expression cassette or vector disclosed herein is used to treat a blood clotting disorder, wherein the expression cassette or vector comprises one or more REs (e.g., SEQ ID NO: 1, 2, 3, 4, 13, 14, 15, 16, 17, 22, 23, 24, 25, 26, 27, 28, 29, 30, 31, 32, 33, 34, 35, 36, 37, 38, 39, 40, 41) operably linked to a therapeutic transgene, wherein the transgene is a fibrinogen, prothrombin, a coagulation factor, or a blood clotting factor (e.g., Factor 1, 2, 3, 4, 5, 6, 7, 8, 9, 10, 11, or 12) or a transcriptional modulator that acts on an endogenous gene corresponding to a fibrinogen, prothrombin, a coagulation factor, or a blood clotting factor (e.g., Factor 1, 2, 3, 4, 5, 6, 7, 8, 9, 10, 11, or 12). In some cases, the transgene is Factor VIII. In some cases, such expression cassette or vector is delivered into a subject diagnosed with or at risk for a blood clotting disorder. In some cases, such expression cassette or vector is delivered into a subject via intravenous infusion or injection. In some cases, the delivery is systemic. In some cases, a method of treating a blood clotting disorder comprising administering a gene therapy (e.g., an AAV gene therapy) into a subject in need thereof, wherein the gene therapy comprises one or more REs of this disclosure (e.g., SEQ ID NO: 1, 2, 3, 4, 13, 14, 15, 16, 17, 22, 23, 24, 25, 26, 27, 28, 29, 30, 31, 32, 33, 34, 35, 36, 37, 38, 39, 40, 41) operably linked to a therapeutic transgene, wherein the transgene is Factor VIII or a transcriptional modulator that acts on an endogenous Factor VIII gene to increase its expression in a cell or in vivo. In some cases, the transgene is any one of Factor 1, 2, 3, 4, 5, 6, 7, 8, 9, 10, 11, or 12. In some cases, the expression cassette or vector is an AAV. In some cases, the expression cassette or vector is preferentially expressed in hepatocytes or in the liver.

In some cases, the transgene may be a DNA binding protein, or a protein associated with DNA binding. In some cases, a DNA binding protein may be a transcription factor, or a part of a transcription factor. In some cases, a DNA binding protein may be Cas9, a Cas family protein, saCas9, dCas9, a dCas family protein, a transcriptional activator like effector (TALE) protein, or a zinc finger protein, or a fusion protein. In some cases, a method of treating a genetic disorder comprises administering an expression cassette or vector comprising a gene editing protein (e.g., Cas9 and a guide RNA) and one or more REs of this disclosure (e.g., SEQ ID NO: 1, 2, 3, 4, 13, 14, 15, 16, 17, 22, 23, 24, 25, 26, 27, 28, 29, 30, 31, 32, 33, 34, 35, 36, 37, 38, 39, 40, 41). In some cases, the guide RNA targets the Cas protein to an endogenous gene of interest or an endogenous gene disclosed herein.

In some cases, the constructs disclosed herein are used to deliver a gene therapy. In particular, relatively short regulatory elements of this disclosure can be of particular utility for gene therapy requiring the expression of large transgenes, such as Factor VIII or ATP7B. In some embodiments, a large transgene is expressed in liver cells, such as hepatocytes. In other embodiments, a large transgene is expressed in central nervous system (CNS), such as neurons. In some embodiments, any one of the transgenes disclosed herein is operably linked to one or more regulatory elements disclosed herein to increase expression of the transgene. In some cases, transgenes disclosed herein are expressed in a cell or in vivo, in vitro, and/or ex vivo. In some cases, such large transgenes are delivered into a cell using a gene therapy, a recombinant expression vector or plasmid, or a viral vector or plasmid. Examples of large transgenes that can be expressed as part of a gene therapy or an expression system ex vivo or in vitro include, but are not limited to: Menkes' protein (ATP7A), ATP binding cassette subfamily b member 4 (ABCB4), ATPase phospholipid transporting 8B1 (ATP8B1), ATPase copper transporting beta (ATP7B), cyclin-dependent kinase-like 5 (CDKL5), contactin associated protein-like 2 (CNTNAP2), ATP binding cassette subfamily B member 11 (ABCB11), and zinc finger E-box-binding homeobox 2 (ZEB2), and any variant, subunit, mutant, or functional fragment thereof, including codon-optimized variants.

In some embodiments, the constructs disclosed herein are used for gene editing. For example, a construct can comprise a regulatory element as disclosed herein, a Cas9 coding sequence, and a guide RNA. In some cases, the Case9 coding sequence encodes saCas9. A construct with a Cas9 or saCas9 coding sequence and guide RNA can be used to correct a dysfunctional gene, for example, by correcting a mutation (e.g., removing a premature stop codon).

Also contemplated herein are gene therapies or expression vectors comprising one or more regulatory elements as disclosed herein to treat various diseases, including various genetic disorders, such as severe combined immune deficiency (ADA-SCID), Menkes disease, familial intrahepatic cholestasis, Byler syndrome, Wilson disease, cortical dysplasia-focal epilepsy syndrome, Mowat-Wilson syndrome, PFIC2, PFIC3, chronic granulomatous disorder, hemophilia, congenital blindness, metabolic disorders, lysosomal storage disease, muscular dystrophy, cancer, viral infections, heart diseases, and diabetes. In some cases, a gene therapy comprising one or more regulatory elements as disclosed herein may be used to treat Wilson's disease.

Figure 5A:
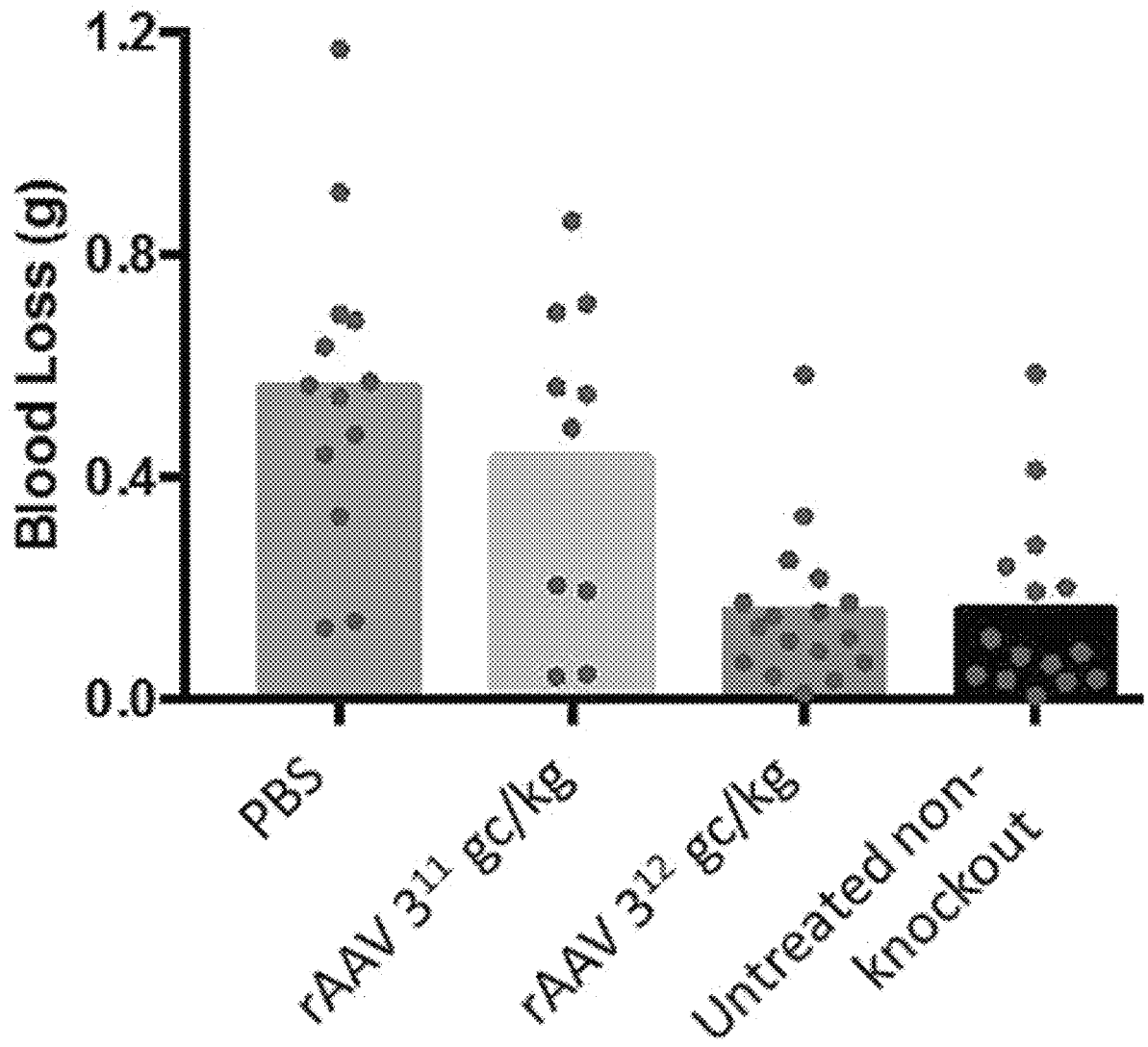
FIG. 5A illustrates an example of gene therapy used to treat a blood clotting deficiency in FVIII knockout mice in vivo using an rAAV expression cassette comprising a regulatory element of this disclosure. Blood loss (g) results of mice treated with PBS control or rAAV comprising a regulatory element of this disclosure at a dose of $3^{11}$ genome copies/kg (gc/kg) or at a dose of $3^{12}$ gc/kg were compared to untreated non-knockout mice. Treatment of mice with the rAAV gene therapy at the dose of $3^{12}$ gc/kg resulted in a reduction in blood loss as compared to the controls (e.g., PBS control mice).
Figure 5B:
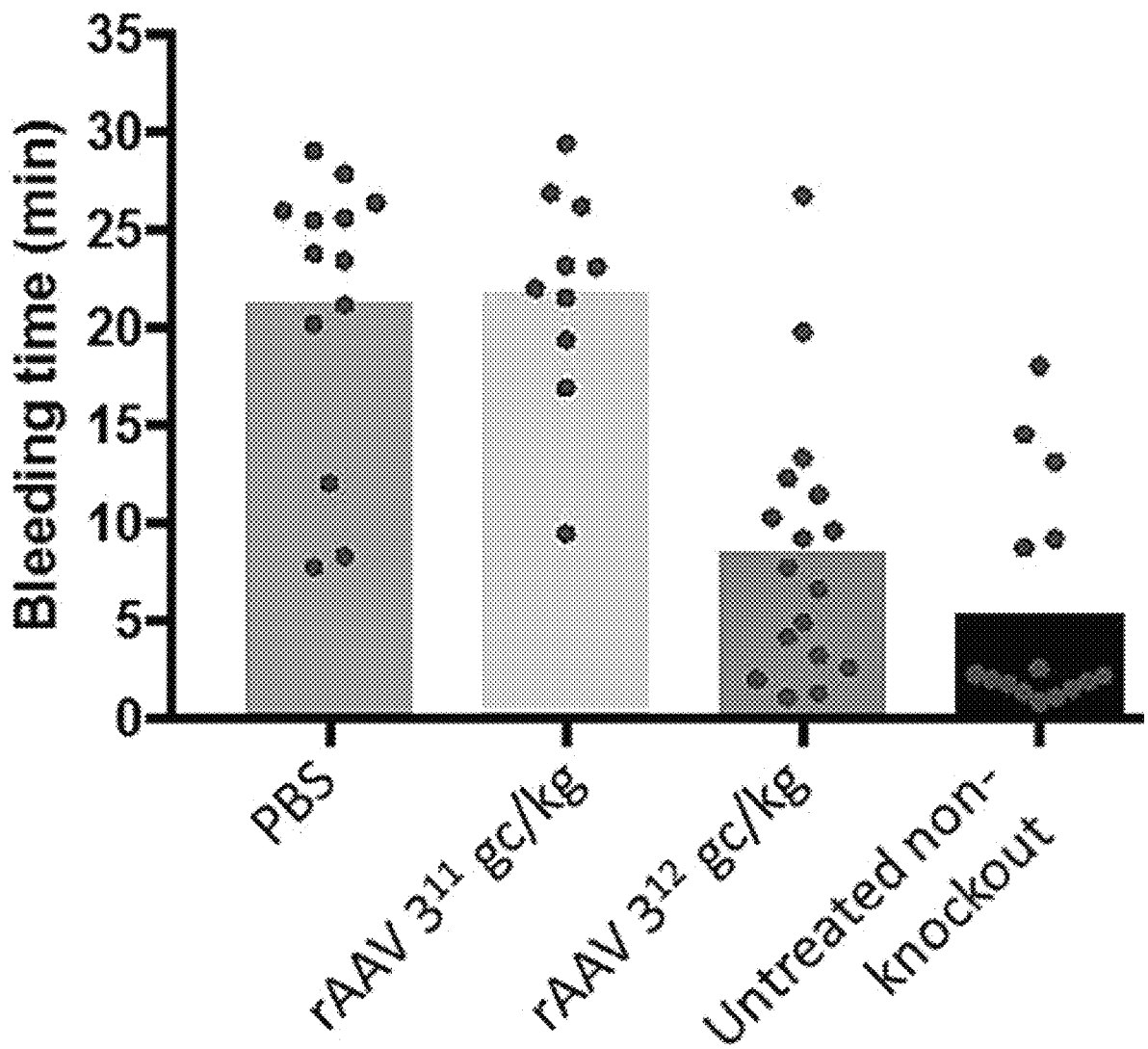
FIG. 5B illustrates the bleeding time of the mice in minutes (min) till clotting.
Figure 10:
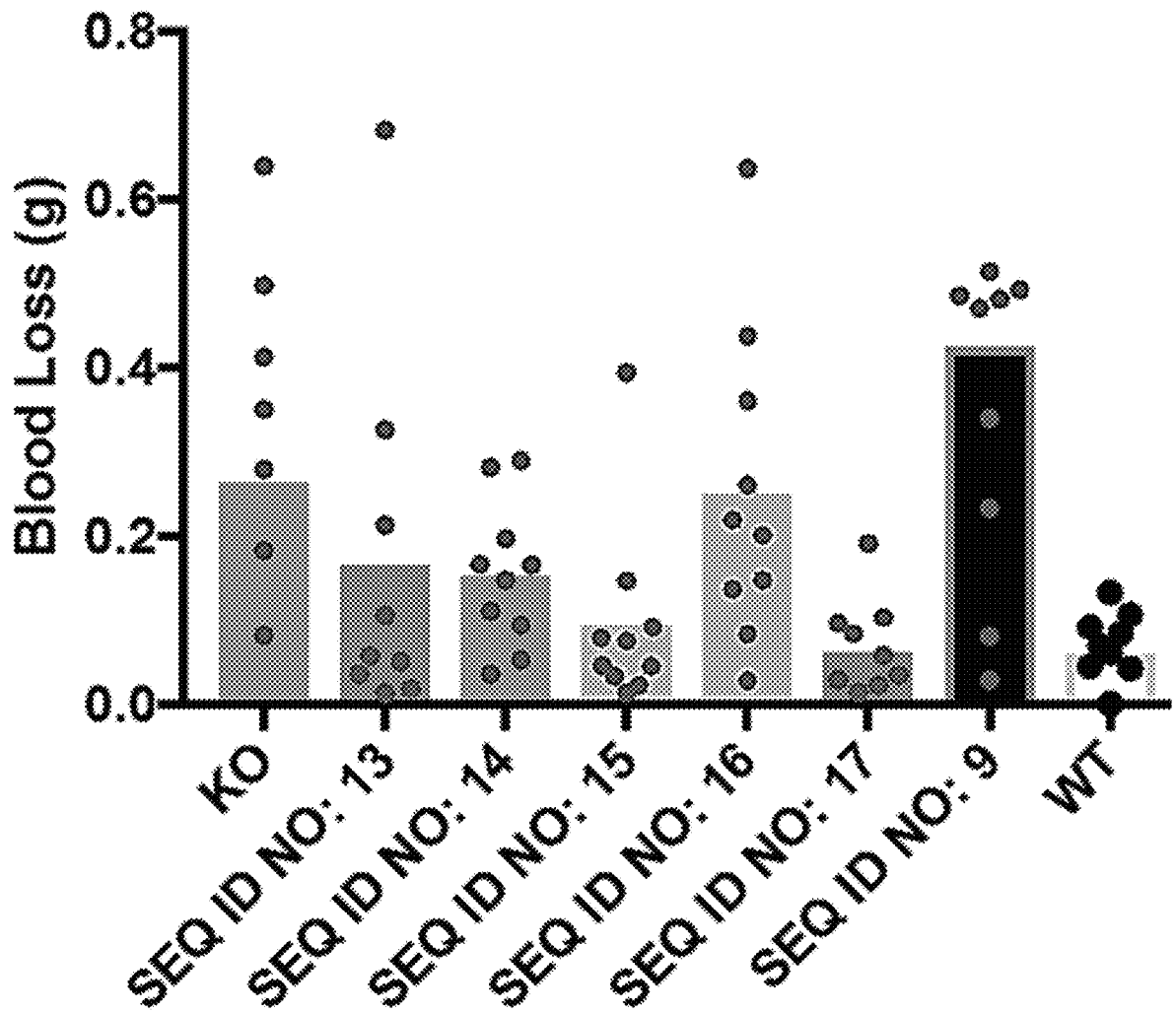
FIG. 10 illustrates blood loss experiments, measured in grams (g), with mice treated with various expression cassettes of this disclosure, wherein SEQ ID NOs: 13-17 refer to a regulatory element.
Figure 11:
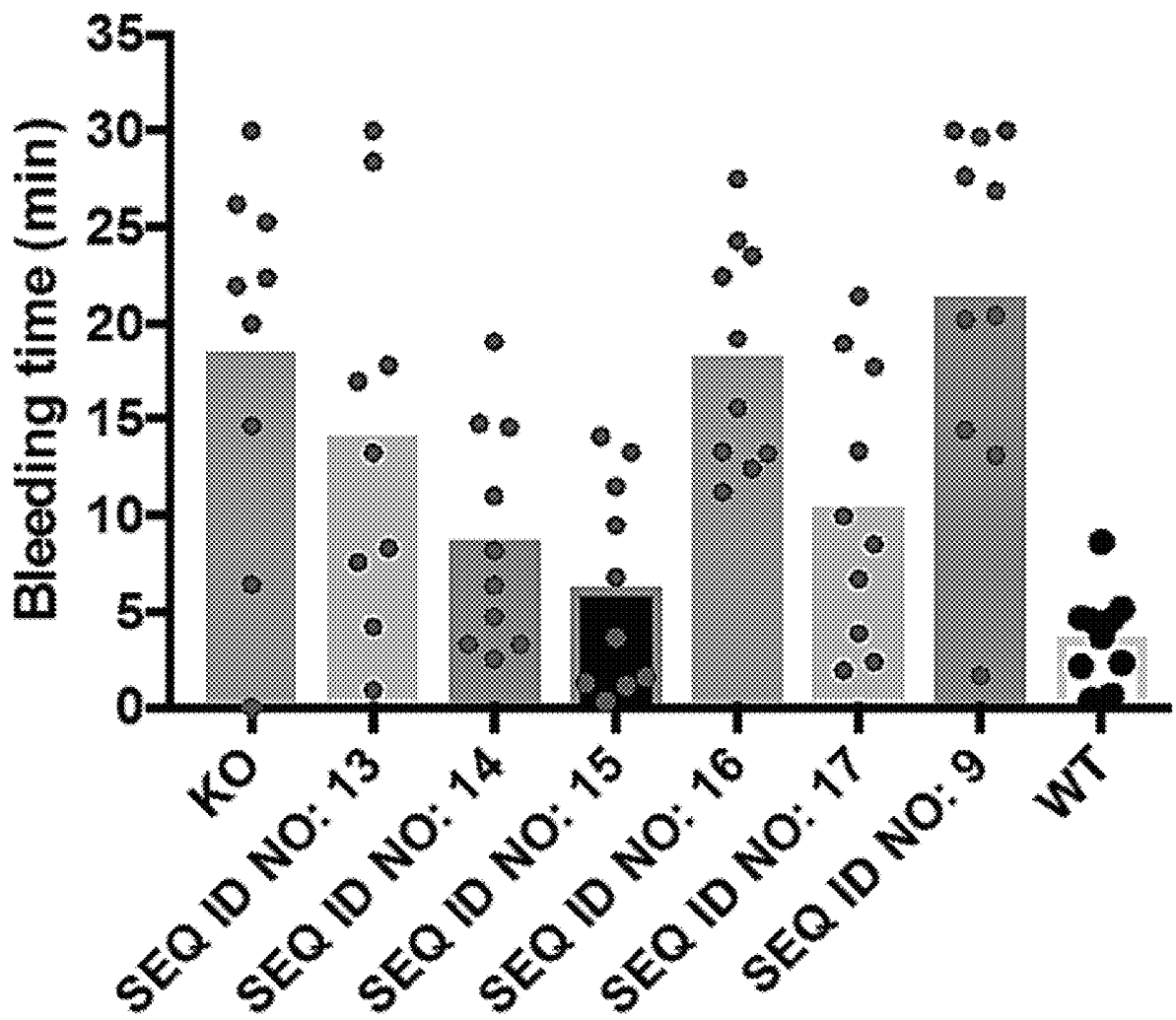
FIG. 11 illustrates the bleeding time in minutes (min.) till clotting in mice treated with various expression cassettes of this disclosure, wherein SEQ ID NOs: 13-17 refer to a regulatory element.
Figure 12:
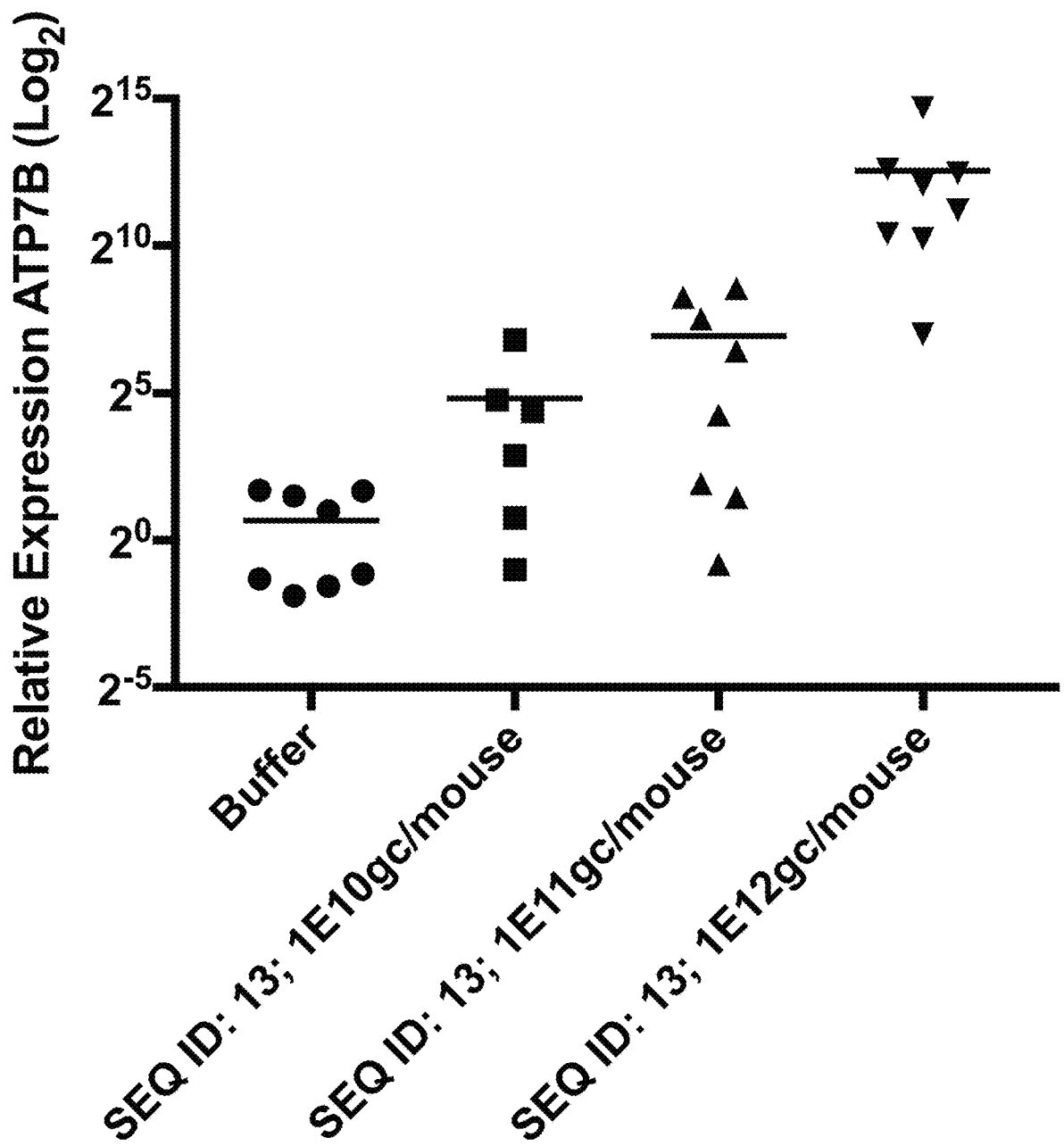
FIG. 12 illustrates the relative expression of ATP7B ($Log_2$) in mice treated with an expression cassette comprising a regulatory element having a sequence of SEQ ID NO: 13 at doses of 1E10 (or $10^{10}$) genomic copies per mouse (gc/mouse), 1E11 (or $10^{11}$) gc/mouse, or 1E12 (or $10^{12}$) gc/mouse. The data showed a positive correlation between the dose of the expression cassette comprising SEQ ID NO: 13 and the expression of ATP7B in vivo.

In some embodiments, the regulatory elements disclosed herein are used to treat a subject with a blood clotting disorder. For example, an expression cassette containing a regulatory element of this disclosure and a coding sequence for FVIII can be used to rescue a clotting disorder or disease in a subject with a FVIII deficiency. Transfecting an expression cassette containing a regulatory element of this disclosure and a coding sequence for FVIII into a subject with a clotting disorder may result in a decrease in blood loss after injury, as shown in FIG. 5A and FIG. 10. Transfecting an expression cassette containing a regulatory element of this disclosure and a coding sequence for FVIII into a subject with a clotting disorder may result in a blood loss of at least about 10%, 20%, 30% Transfecting an expression cassette containing a regulatory element of this disclosure and a coding sequence for FVIII into a subject with a clotting disorder may result in a decrease time for bleeding to stop after injury, as shown in FIG. 5B and FIG. 11.

Subjects that can be treated with any one of the constructs, gene therapy, or expression vectors/cassettes of this disclosure include humans, primates, dogs, cats, rodents, horses, cows, sheep, pigs, and other livestock. In some cases, the subject has a disease/disorder or is at risk of a disease/disorder. For example, the subject may have a genetic disease, or have a DNA sequence known to be linked to a genetic disease or predisposition for the disease. In some cases, the subject has hemophilia. In some cases, the subject has hemophilia A. In some embodiments, the subject has a defect in Factor VIII. In some embodiments, a gene therapy comprising one or more regulatory elements described herein operably linked to Factor VIII is used to treat a subject diagnosed with hemophilia A.

EXAMPLES

These examples are provided for illustrative purposes only and not to limit the scope of the claims provided herein.

Example 1

High Expression in HEK293T Cells

HEK293T cells were transfected with plasmid DNA containing a luciferase gene under the control of one of several different regulatory elements, i.e., no promoter control, SCP, CMV, SEQ ID NO: 3 (SEQ ID NO: 1 operably linked to min CMV), SEQ ID NO: 4 (SEQ ID NO: 2 operably linked to min CMV), and CAG. The normalized luciferase values from each construct are illustrated in FIG. 1A. The size-normalized activity values from each construct are illustrated in FIG. 1B. The sequences of the regulatory elements and promoters used herein are provided in TABLE 1 above and TABLE 3 below. Regulatory element SEQ ID NO: 1 linked to a min CMV promoter and regulatory element SEQ ID NO: 2 linked to a min CMV promoter drove higher levels of luciferase expression than min CMV alone and SCP alone. Both SEQ ID NO: 1 and SEQ ID NO: 2, when linked to a min CMV promoter, drove high expression of luciferase in HEK293T kidney cells as compared to the control, SCP, or min CMV promoter without the regulatory element (i.e., SEQ ID NO: 1 or 2).

Figure 1C:
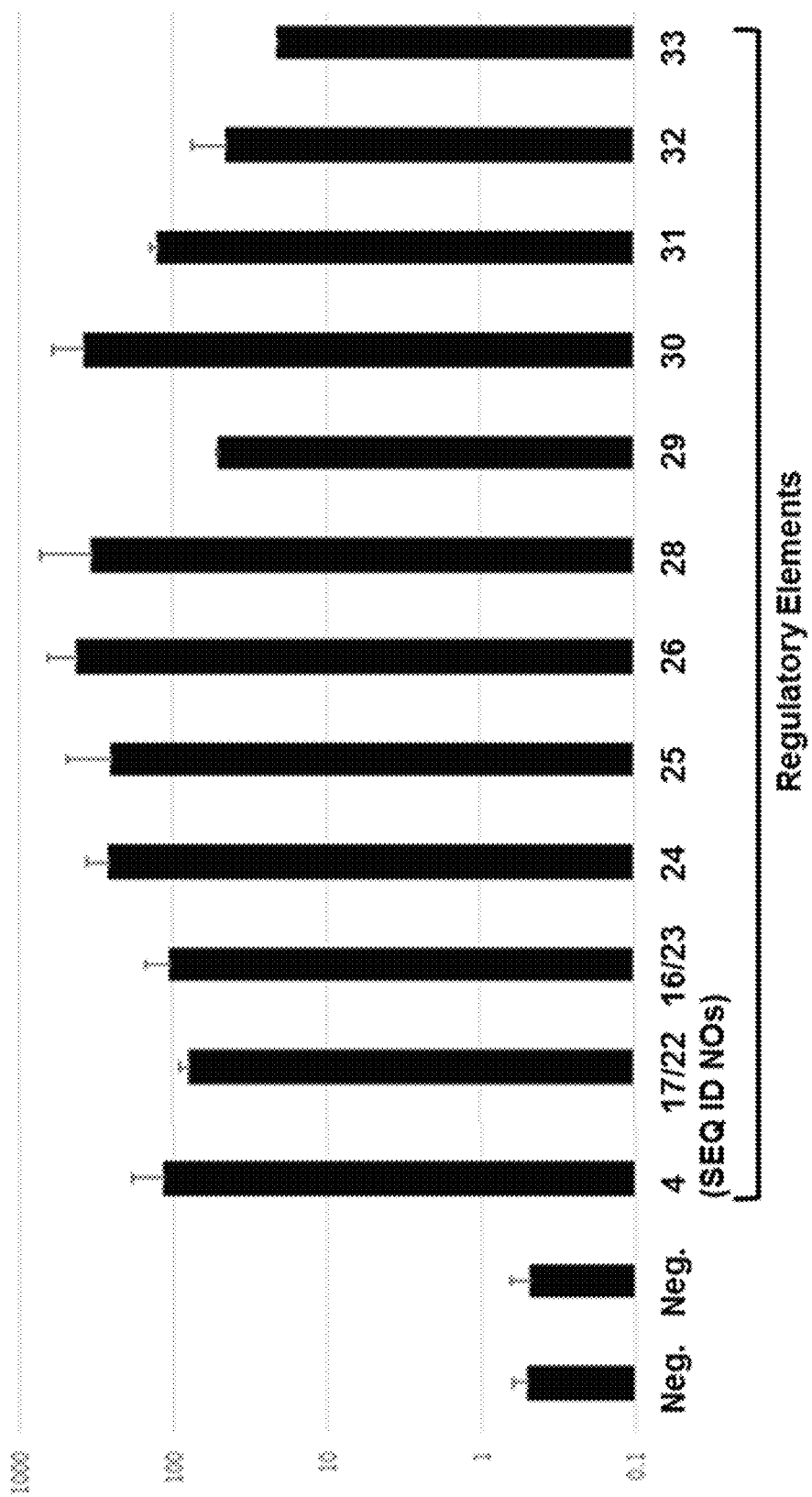
FIG. 1C illustrates normalized luciferase expression of regulatory elements SEQ ID NOs: 17 and 22 combined, SEQ ID NOs: 16 and 23 combined, SEQ ID NO: 24, SEQ ID NO: 25, SEQ ID NO: 26, SEQ ID NO: 28, SEQ ID NO: 29, SEQ ID NO: 31, SEQ ID NO: 32, and SEQ ID NO: 33 as compared to negative controls and a positive control (SEQ ID NO: 4). All the REs resulted in high levels of normalized luciferase expression that were comparable to the level of expression drove by SEQ ID NO: 4.
Figure 1D:
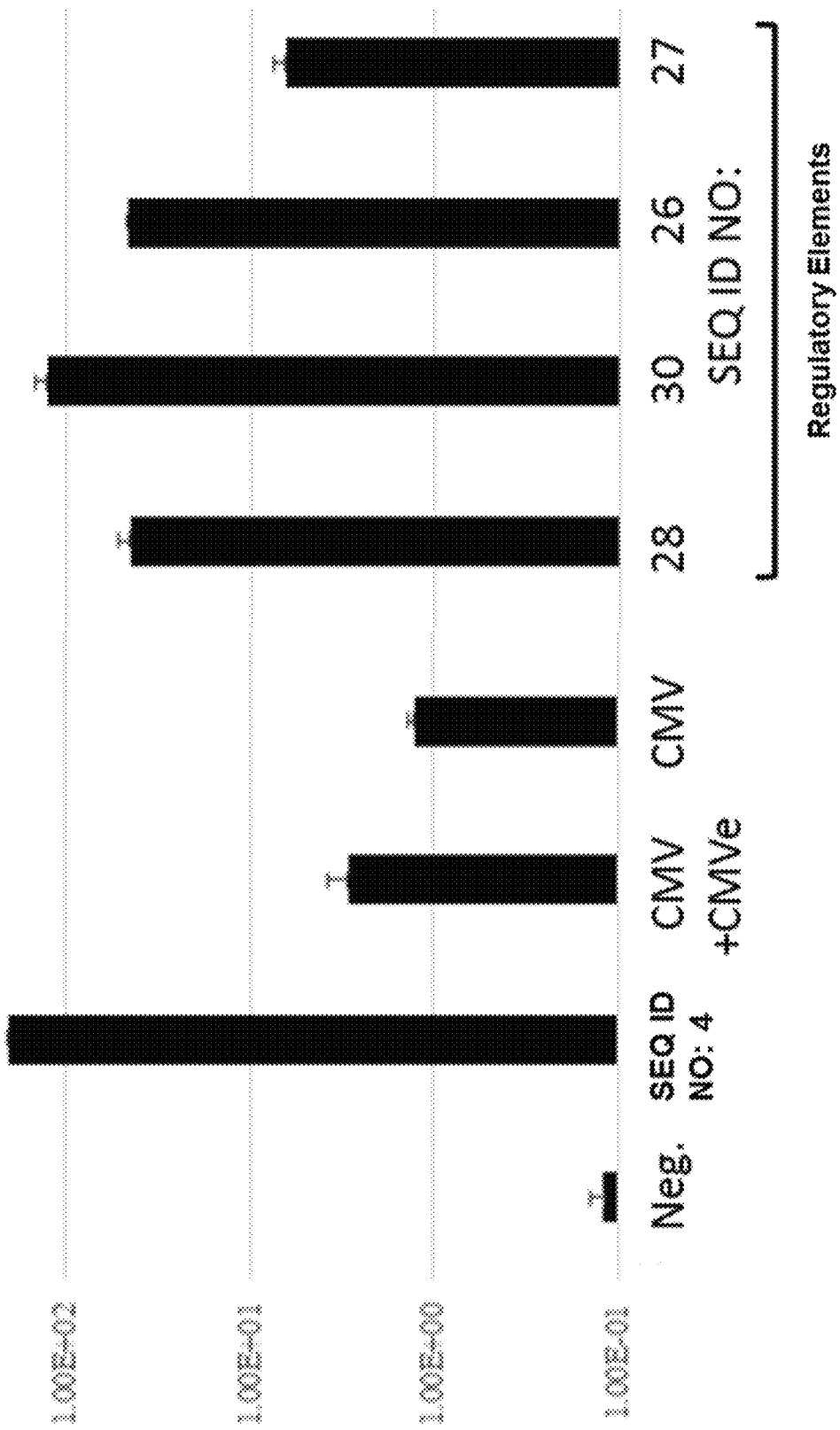
FIG. 1D illustrates normalized luciferase expression of regulatory elements SEQ ID NO: 28, SEQ ID NO: 30, SEQ ID NO: 26, or SEQ ID NO: 27 as compared to a negative control, positive control (SEQ ID NO: 4), CMV+CMVe, and CMV alone in HEK293T cells. Each regulatory element drove higher luciferase expression than CMV alone and CMV+CMVe.
Figure 1E:
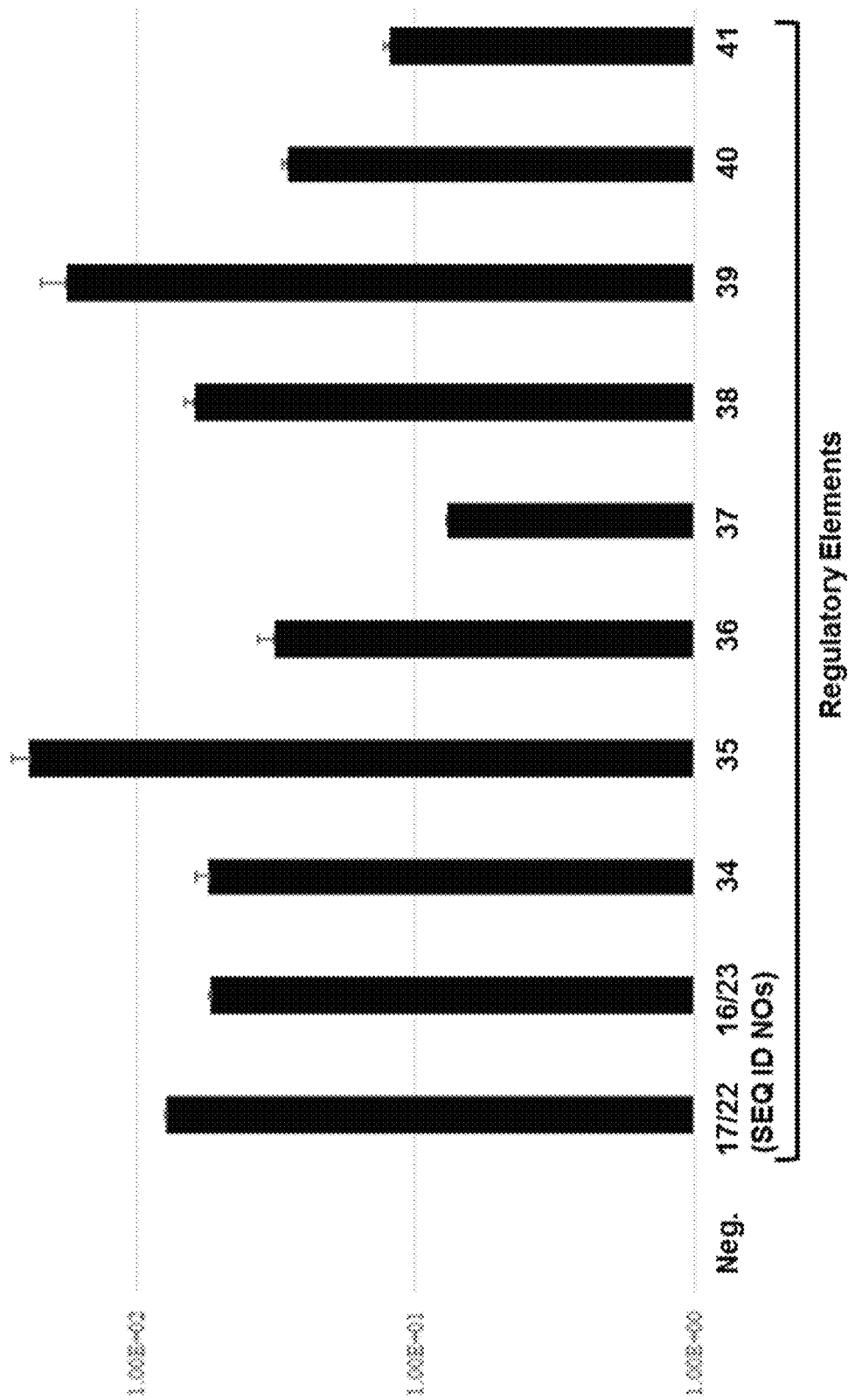
FIG. 1E illustrates normalized luciferase expression of regulatory elements SEQ ID NOs: 17 and 22 combined, SEQ ID NOs: 16 and 23 combined, SEQ ID NO: 34, SEQ ID NO: 35, SEQ ID NO: 36, SEQ ID NO: 37, SEQ ID NO: 38, SEQ ID NO: 39, SEQ ID NO: 40, or SEQ ID NO: 41 as compared to a negative control in HEK293T cells. Each regulatory element tested drove higher luciferase expression than the negative control.

Similar normalized luciferase expression experiments were done with additional controls and regulatory sequences, as illustrated in FIG. 1C, FIG. 1D, and FIG. 1E. Firefly expression was also assayed to ensure similar transfection efficiency in all the samples tested. In FIG. 1C, normalized luciferase expression of regulatory elements SEQ ID NO: 4, SEQ ID NOs: 17 and 22 combined (or SEQ ID NO: 17/22), SEQ ID NOs: 16 and 23 combined (or SEQ ID NO: 16/23), SEQ ID NO: 24, SEQ ID NO: 25, SEQ ID NO: 26, SEQ ID NO: 28, SEQ ID NO: 29, SEQ ID NO: 31, SEQ ID NO: 32, and SEQ ID NO: 33 were compared with two negative controls (i.e., sequences known to not drive any expression). Each of the regulatory elements tested resulted in high levels of luciferase expression, e.g., by at least 10, 50, or 100 or more fold as compared to the negative controls.

In FIG. 1D, normalized luciferase expression from plasmids comprising regulatory elements SEQ ID NO: 4, SEQ ID NO: 28, SEQ ID NO: 30, SEQ ID NO: 26, or SEQ ID NO: 27 were compared to a negative control, and a similar plasmid comprising either CMV linked to CMVe or CMV operably linked to luciferase. Each regulatory element tested (i.e., SEQ ID NO: 4, SEQ ID NO: 28, SEQ ID NO: 30, SEQ ID NO: 26, and SEQ ID NO: 27) resulted in higher luciferase expression than the negative control, CMV alone, and CMV+CMVe. The relatively short REs tested showed at least 10 fold, at least 15 fold, at least 20 fold, at least 30 fold, at least 40 fold, or more than 50 fold normalized luciferase expression as compared to a plasmid comprising a CMV promoter or CMV+CMVe linked to luciferase.

In FIG. 1E, normalized luciferase expression from plasmids comprising regulatory elements SEQ ID NO: 17/22, SEQ ID NO: 16/23, SEQ ID NO: 34, SEQ ID NO: 35, SEQ ID NO: 36, SEQ ID NO: 37, SEQ ID NO: 38, SEQ ID NO: 39, SEQ ID NO: 40, or SEQ ID NO: 41 operably linked to luciferase were compared to a negative control (i.e., sequence known to have no expression activity). Each regulatory element (i.e., SEQ ID NOs: 17/22, 16/23, and 34-41) drove higher luciferase expression than the negative control, while each of SEQ ID NO: 35 and SEQ ID NO: 39 drove a normalized luciferase expression higher than $10^2$, or at least 100 fold higher luciferase expression than the negative control.

TABLE 3

Additional Sequences Disclosed Herein

| SEQ ID NO. | Sequence (5'-to-3') | Name |
|---|---|---|
| 5 | GTACTTATATAAGGGGGTGGGGGCGCGTTCGTCCTCAGTCGCGA TCGAACACTCGAGCCGAGCAGACGTGCCTACGGACC | SCP |
| 6 | GGGGAGGCTGCTGGTGAATATTAACCAAGGTCACCCCAGTTATC GGAGGAGCAAACAGGGGCTAAGTCCACGCTAGCGTCTGTCTGCA CATTTCGTAGAGCGAGTGTTCCGATACTCTAATCTCCCTAGGCAA GGTTCATATTTGTGTAGGTTACTTATTCTCCTTTTGTTGACTAAGT CAATAATCAGAATCAGCAGGTTTGGAGTCAGCTTGGCAGGGATC AGCAGCCTGGGTTGGAAGGAGGGGGTATAAAAGCCCCTTCACCA GGAGAAGCCGTC | SerpE_TTR |
| 7 | GTTTGCTGCTTGCAATGTTTGCCCATTTTAGGGTGGACACAGGAC GCTGTGGTTTCTGAGCCAGGGCTAGCGGGCGACTCAGATCCCAG CCAGTGGACTTAGCCCCTGTTTGCTCCTCCGATAACTGGGGTGAC CTTGGTTAATATTCACCAGCAGCCTCCCCCGTTGCCCCTCTGGAT CCACTGCTTAAATACGGACGAGGACAGGGCCCTGTCTCCTCAGC TTCAGGCACCACCACTGACCTGGGACAGTGAATCGCCAC | Proto 1 |
| 8 | TGATGCGGTTTTGGCAGTACATCAATGGGCGTGGATAGCGGTTT GACTCACGGGGATTTCCAAGTCTCCACCCCATTGACGTCAATGG GAGTTTGTTTTGGCACCAAAATCAACGGGACTTTCCAAAATGTC GTAACAACTCCGCCCCATTGACGCAAATGGGCGGTAGGCGTGTA CGGTGGGAGGTCTATATAAGCAGAGCT | minCMV |
| 9 | GTTTGCTGCTTGCAATGTTTGCCCATTTTAGGGTGGACACAGGAC GCTGTGGTTTCTGAGCCAGGGGGCGACTCAGATCCCAGCCAGTG GACTTAGCCCCTGTTTGCTCCTCCGATAACTGGGGTGACCTTGGT TAATATTCACCAGCAGCCTCCCCCGTTGCCCCTCTGGATCCACTG CTTAAATACGGACGAGGACAGGGCCCTGTCTCCTCAGCTTCAGG CACCACCACTGACCTGGGACAGTGAATC | UCL-HLP |
| 10 | CGTTACATAACTTACGGTAAATGGCCCGCCTGGCTGACCGCCCA ACGACCCCCGCCCATTGACGTCAATAATGACGTATGTTCCCATA GTAACGCCAATAGGGACTTTCCATTGACGTCAATGGGTGGAGTA TTTACGGTAAACTGCCCACTTGGCAGTACATCAAGTGTATCATAT GCCAAGTACGCCCCCTATTGACGTCAATGACGGTAAATGGCCCG CCTGGCATTATGCCCAGTACATGACCTTATGGGACTTTCCTACTT GGCAGTACATCTACGTATTAGTCATCGCTATTACCATG | CMVe |
| 11 | GTTACATAACTTACGGTAAATGGCCCGCCTGGCTGACCGCCCAA CGACCCCCGCCCATTGACGTCAATAATGACGTATGTTCCCATAGT AACGCCAATAGGGACTTTCCATTGACGTCAATGGGTGGAGTATT TACGGTAAACTGCCCACTTGGCAGTACATCAAGTGTATCATATG CCAAGTACGCCCCCTATTGACGTCAATGACGGTAAATGGCCCGC CTGGCATTATGCCCAGTACATGACCTTATGGGACTTTCCTACTTG GCAGTACATCTACGTATTAGTCATCGCTATTACCATGGTCGAGG TGAGCCCCACGTTCTGCTTCACTCTCCCCATCTCCCCCCCCTCCCC ACCCCCAATTTTGTATTTATTTATTTTTTAATTATTTTGTGCAGCG ATGGGGGCGGGGGGGGGGGGGCGCGCGCCAGGCGGGGCGGGG CGGGGCGAGGGGCGGGCGGGGCGAGGCGGAGAGGTGCGGCGG CAGCCAATCAGAGCGGCGCGCTCCGAAAGTTTCCTTTTATGGCG AGGCGGCGGCGGCGGCGCCCTATAAAAAGCGAAGCGCGCGGC GGGCGGGAGTCGCTGCGTTGCCTTCGCCCCGTGCCCCGCTCCGC GCCGCCTCGCGCCGCCCGCCCCGGCTCTGACTGACCGCGTTACTC CCACAGGTGAGCGGGCGGGACGGCCCTTCTCCTCCGGGCTGTAA TTAGCGCTTGGTTTAATGACGGCTCGTTTCTTTTCTGTGGCTGCGT GAAAGCCTTAAAGGGCTCCGGGAGGGCCCTTTGTGCGGGGGGA GCGGCTCGGGGGTGCGTGCGTGTGTGTGTGCGTGGGGAGCGCC GCGTGCGGCCCGCGCTGCCCGGCGGCTGTGAGCGCTGCGGGCGC GGCGCGGGGCTTTGTGCGCTCCGCGTGTGCGCGAGGGGAGCGCG GCCGGGGCGGTGCCCCGCGGTGCGGGGGGCTGCGAGGGGAA CAAAGGCTGCGTGCGGGGTGTGTGCGTGGGGGGGTGAGCAGGG GGTGTGGGCGCGGCGGTCGGCTGTAACCCCCCCCTGCACCCCC CTCCCCGAGTTGCTGAGCACGGCCCGGCTTCGGGTGCGGGCTC | CAG |

TABLE 3-continued

Additional Sequences Disclosed Herein

| SEQ ID NO. | Sequence (5'-to-3') | Name |
|---|---|---|
|  | CGTGCGGGCGTGGCGCGGGGCTCGCCGTGCCGGGCGGGGGT GGCGGCAGGTGGGGGTGCCGGGCGGGGCGGGGCCGCCTCGGGC CGGGGAGGGCTCGGGGGAGGGGCGCGGCGGCCCCGGAGCGCCG GCGGCTGTCGAGGCGCGGCGAGCCGCAGCCATTGCCTTTTATGG TAATCGTGCGAGAGGGCGCAGGGACTTCCTTTGTCCCAAATCTG GCGGAGCCGAAATCTGGGAGGCGCCGCCGCACCCCCTCTAGCGG GCGCGGGCGAAGCGGTGCGGCGCCGGCAGGAAGGAAATGGGCG GGGAGGGCCTTCGTGCGTCGCCGCGCCGCCGTCCCCTTCTCCATC TCCAGCCTCGGGGCTGCCGCAGGGGGACGGCTGCCTTCGGGGGG GACGGGGCAGGGCGGGGTTCGGCTTCTGGCGTGTGACCGGCGGC TCTAGAGCCTCTGCTAACCATGTTCATGCCTTCTTCTTTTTCCTAC AGCTCCTGGGCAACGTGCTGGTTGTTGTGCTGTCTCATCATTTTG GCAAAGAATT |  |
| 12 | GCTCCGGTGCCCGTCAGTGGGCAGAGCGCACATCGCCCACAGTC CCCGAGAAGTTGGGGGGAGGGGTCGGCAATTGAACCGGTGCCTA GAGAAGGTGGCGCGGGGTAAACTGGGAAAGTGATGTCGTGTACT GGCTCCGCCTTTTTCCCGAGGGTGGGGGAGAACCGTATATAAGT GCAGTAGTCGCCGTGAACGTTCTTTTTCGCAACGGGTTTGCCGCC AGAACACAGG | EFS |

Example 2

Global High Drivers

Figure 2A:
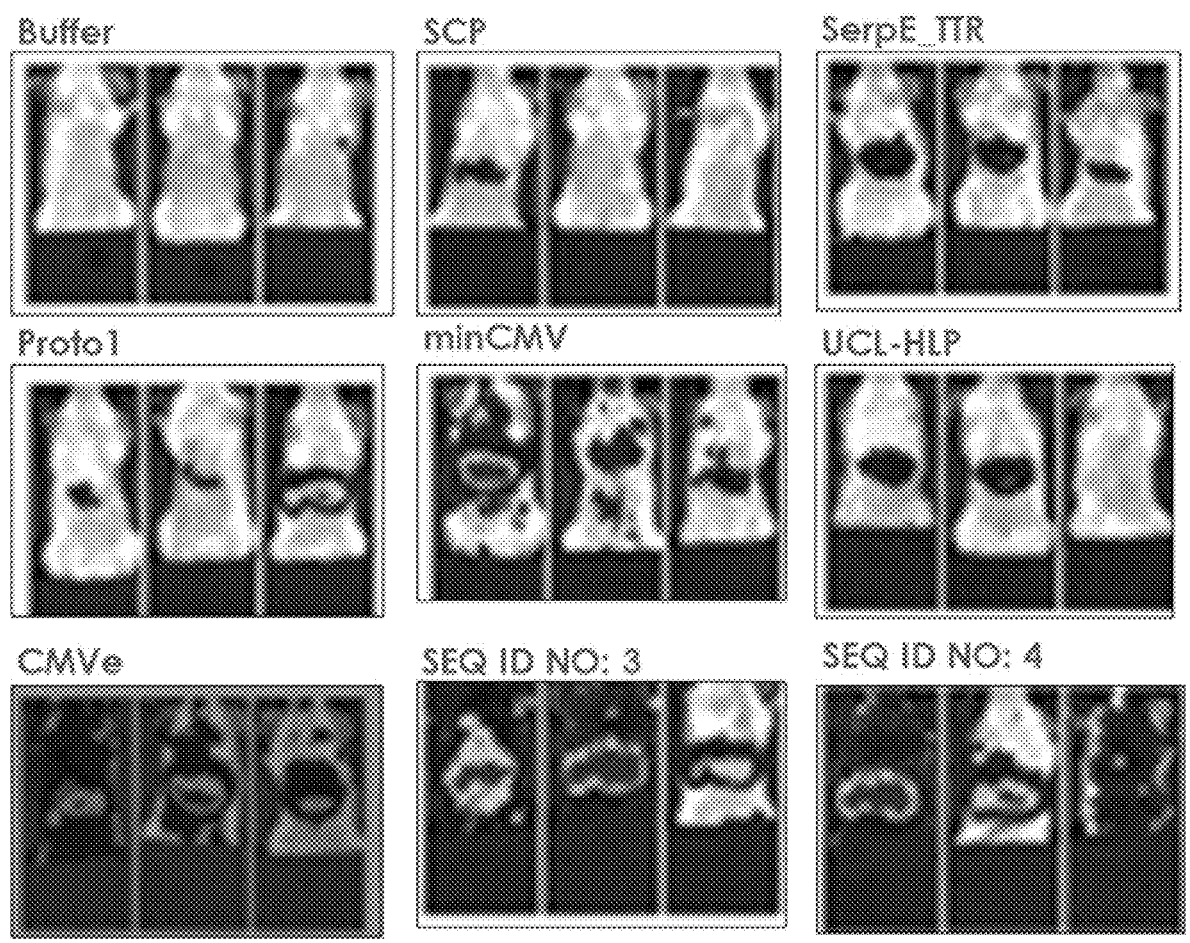
FIG. 2A illustrates the expression of luciferase in mice dosed with expression cassettes comprising luciferase under the control of different regulatory elements (SCP, SerpE_TTR, Proto1, min CMV, UCL-HLP, CMVe, SEQ ID NO: 3, or SEQ ID NO: 4).
Figure 2B:
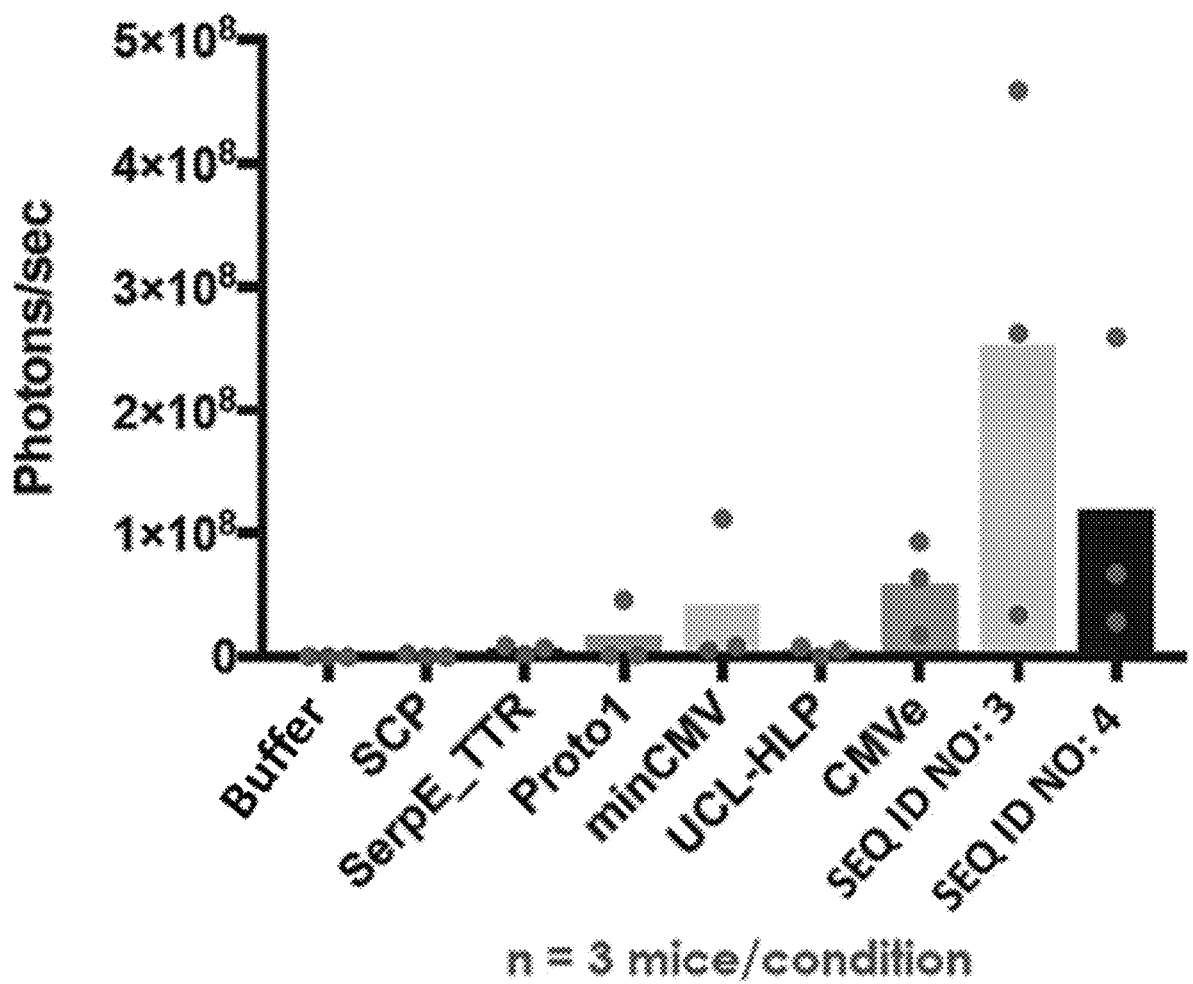
FIG. 2B illustrates the quantification of the average total luminescence (photons/sec) from luciferase expression observed in 3 mice injected with the expression cassettes of FIG. 2A.

To assess the expression patterns of regulatory elements SEQ ID NO: 1 and SEQ ID NO: 2, recombinant AAV vectors were made containing each regulatory element linked to luciferase. Regulatory elements used were: SCP, SERpE_TTR, Proto1, CMV, UCL-HLP, CMVe, SEQ ID NO: 1, and SEQ ID NO: 2. Plasmid DNA was delivered to SCID-beige mice (12 μg of expression vector per mouse) via hydrodynamic tail vein injection and expression of luciferase was assayed by injecting the mice with 5 ug (~0.25 mg/kg) of furimazine 48 hours post injection. FIG. 2A illustrates the expression of luciferase under the control of different regulatory elements, and illustrates SEQ ID NOs: 1 and 2, when each RE is linked to min CMV, were able to drive expression of the operably linked transgene in at least one additional cell type as well as kidney cells, as illustrated by the white regions indicative of luciferase expression in various tissues in mice. As illustrated in FIG. 2B, regulatory elements SEQ ID NO: 3 and SEQ ID NO: 4 each resulted in high levels luciferase expression as compared to the other regulatory elements, as measured by luciferase luminescence in photons/sec.

Example 3

Expression of Human Factor VIII

Figure 3A:
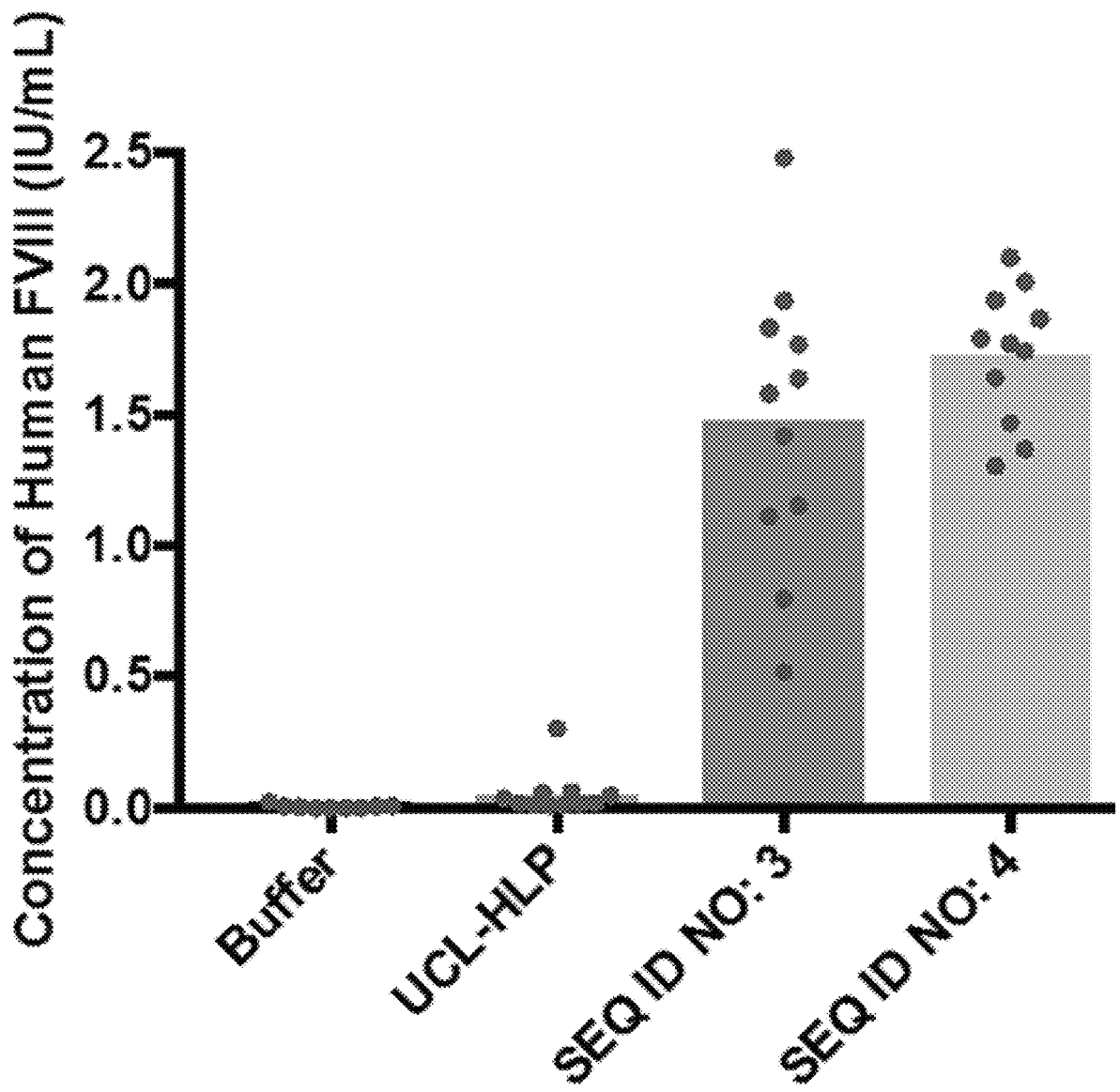
FIG. 3A illustrates the effect of various regulatory elements (UCL-HLP, SEQ ID NO: 3, or SEQ ID NO: 4) on the expression of human factor 8 (FVIII) in mice as measured by an enzyme-linked immunosorbent assay. Expression cassettes comprising either SEQ ID NO: 3 or SEQ ID 4 resulted in elevated levels of human FVIII (IU/mL).
Figure 3B:
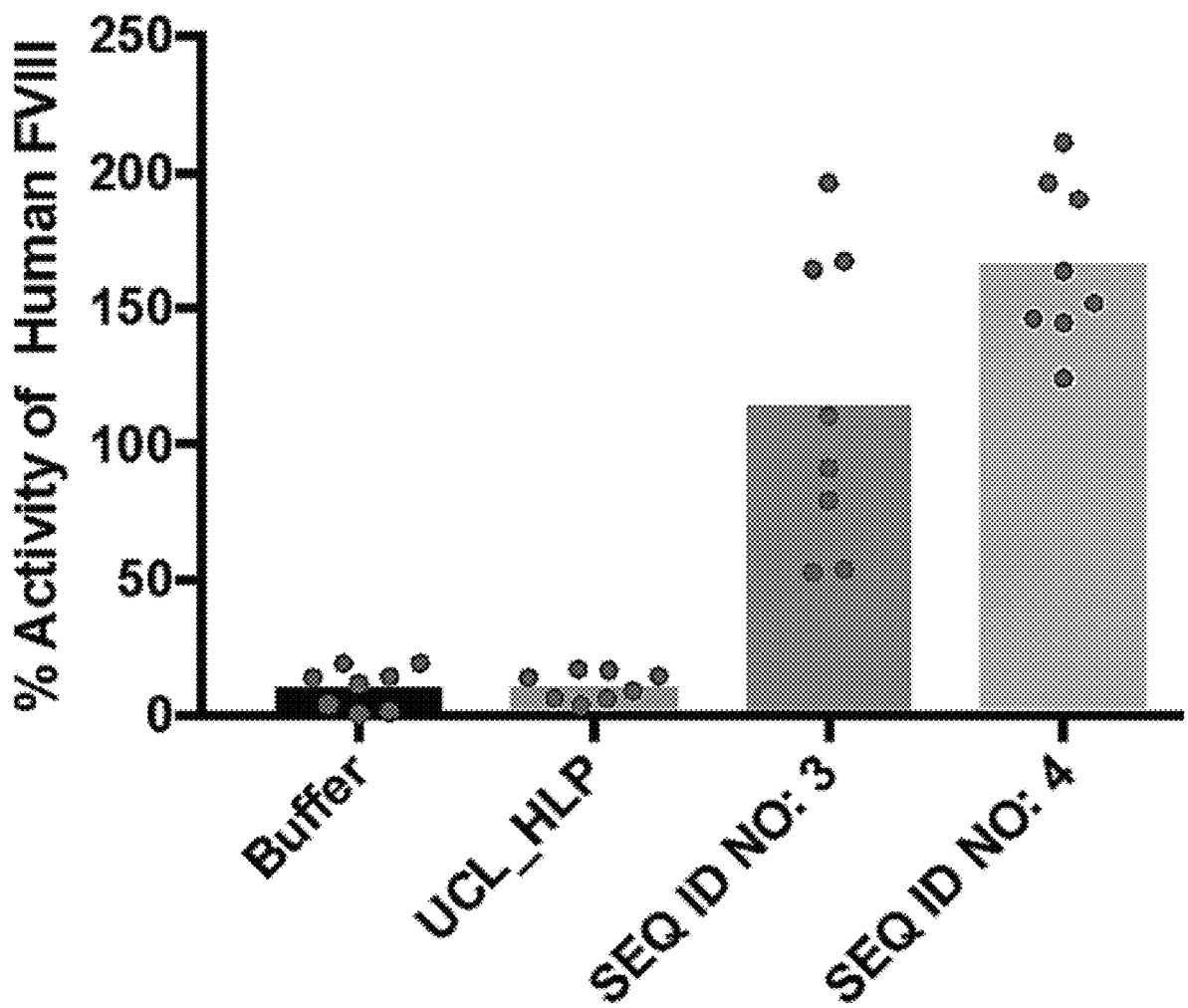
FIG. 3B illustrates the effect of various regulatory elements (UCL-HLP, SEQ ID NO: 3, or SEQ ID NO: 4) on expression of human factor 8 (FVIII) in mice as measured by the Coatest assay, which assayed the percent activity of human FVIII.

SCID-beige mice were injected with 16 μg of expression cassette DNA containing a coding sequence for Factor VIII (NIH Protein Accession ID ABV90867.1) operably linked with UCL-HLP; min CMV with SEQ ID NO: 1; or min CMV with SEQ ID NO: 2. At least eight mice were injected with each of the 3 plasmids, and at least an additional eight mice were injected with buffer. 24 h after injection with plasmid DNA, blood samples were taken and blood plasma was analyzed for Factor VIII activity and concentration using established methods (COATEST® SP4 FVIII, Chromogenix; Visualize™ DVIII Antigen Kit, Affinity Biologicals INC.). As illustrated in FIG. 3A, both min CMV with SEQ ID NO: 1 and min CMV with SEQ ID NO: 2 expression cassettes resulted in high plasma concentrations of Factor VIII at levels of 1.5 IU/ml or higher. FIG. 3B illustrates that both SEQ ID NO: 3 (min CMV with SEQ ID NO: 1) and SEQ ID NO: 4 (min CMV with SEQ ID NO: 2) resulted in plasma Factor VIII activity levels of 100% or higher. Regulatory elements SEQ ID NOs: 1 and/or 2 when operably linked to Factor VIII coding sequence together with min CMV resulted in blood Factor VIII activity levels of 114% and 166%, respectively, which were about 10 fold and 15 fold higher than the activity seen with a UCL-HLP promoter.

Example 4

Gene Editing

Figure 4A:
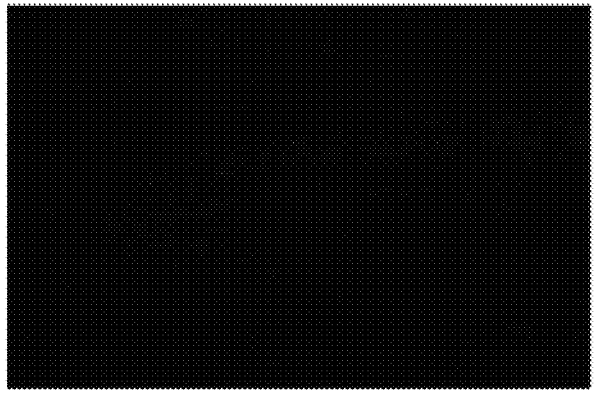
FIG. 4A illustrates gene editing performed in the dente gyms of a mouse brain with a single AAV containing a Cas9 enzyme, a guide RNA, and one of several regulatory elements (min CMV, EFS, or SEQ ID NO: 4) to delete a termination sequence provided upstream of tdTomato (also referred to as red fluorescent protein (RFP)). RFP is represented by light gray color. An expression cassette comprising SEQ ID NO: 4 resulted in gene editing that led to higher expression of RFP as compared to the negative control, min CMV, and EFS.
Figure 4A:
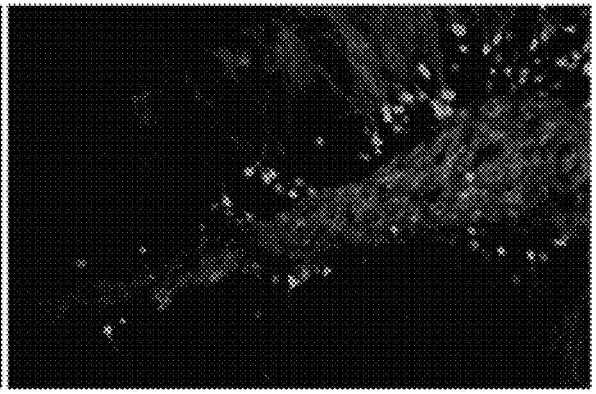
Figure 4A:
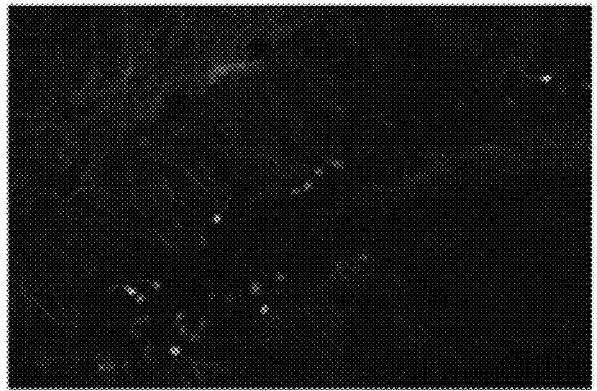
Figure 4A:
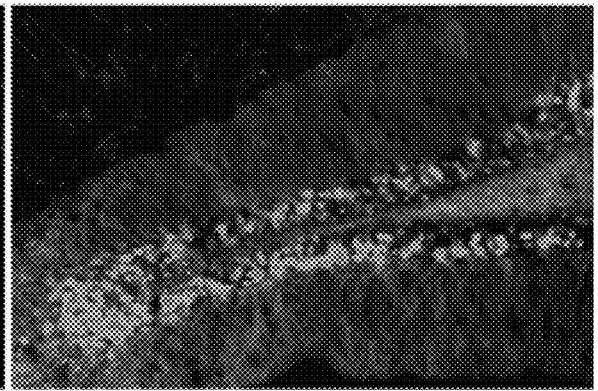
Figure 4B:
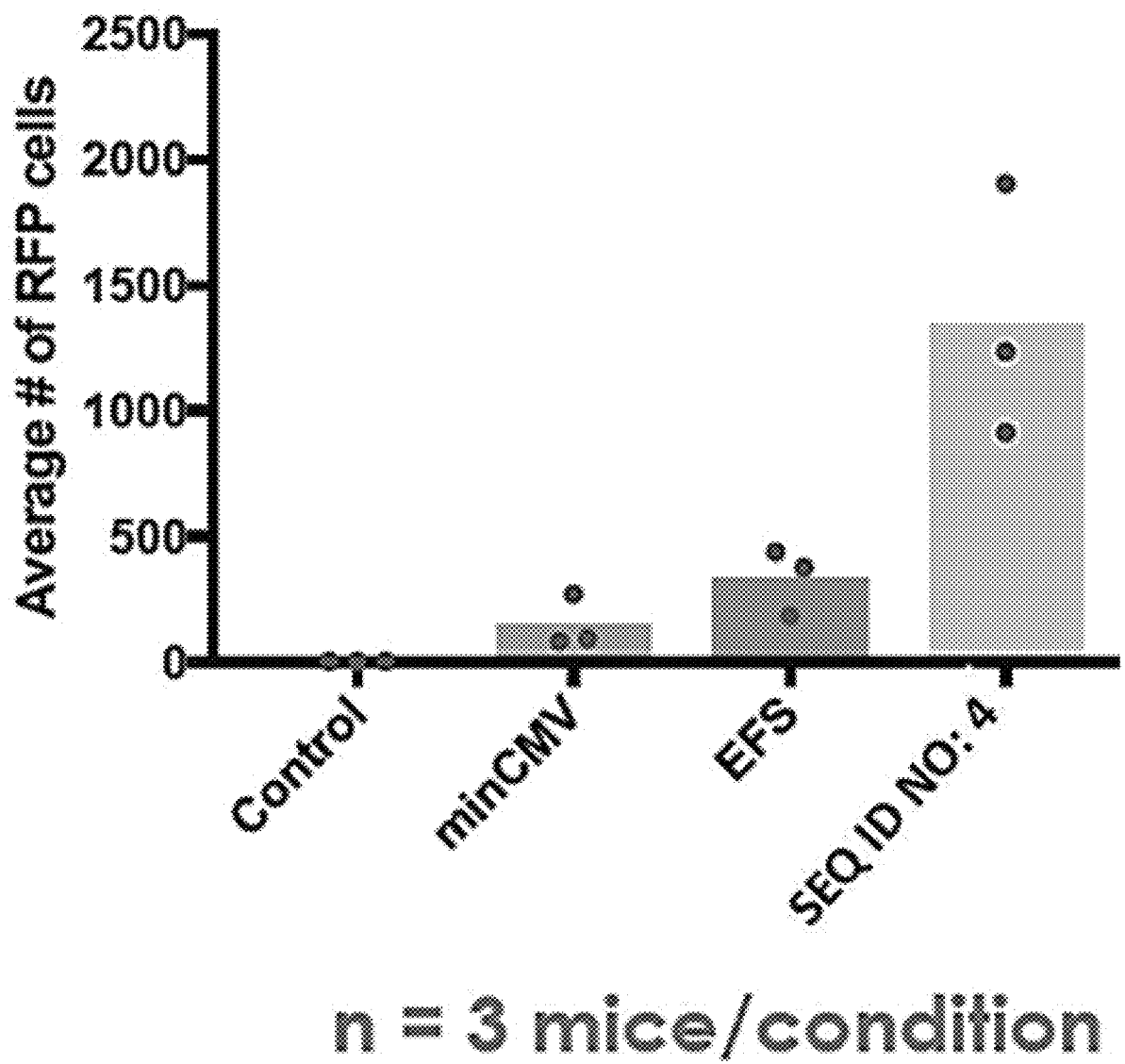
FIG. 4B illustrates the quantification of the average number of RFP-expressing cells in FIG. 4A.

An all-in-one recombinant AAV virion was developed to delete a stop cassette upstream of tdTomato in transgenic mice Ai9 (Jax Stock No: 007909). Once the stop cassette is deleted by saCas9, tdTomato is expressed under the control of a CAG promoter. rAAVs were developed containing saCas9 under the control of either a EFS promoter, a CMV promoter, or a CMV promoter with SEQ ID NO: 2. The rAAVs further comprised two Sa guide RNA scaffolds under the control of U6 promoters. These rAAV virions were injected into the Dente Gyms of the transgenic mice described above. Brains were fixed and sectioned after 3 weeks, and expression of tdTomato in the dente gyms was assessed. As illustrated in FIG. 4B, CMV with SEQ ID NO: 2 (or SEQ ID NO: 4) resulted in more tdTomato expressing cells than CMV alone or EFS. FIG. 4A illustrates that SEQ ID NO: 2 when linked to CMV (or SEQ ID NO: 4) drove expression of the linked transgene (RFP) in at least a subpopulation of brain cells, e.g., neurons.

Example 5

Gene Therapy Treatment of a Blood Clotting Disorder

Genetically engineered FVIII knockout mice (F8tm1Srcmo, deletion of Exon 16-19 of F8 gene; obtained from Shanghai Model Organism Center, Inc., Shanghai, China) have a clotting deficiency which can be assayed by measuring either the volume of blood released by clipping the end of the tail and allowing it to bleed out till clotting occurs, or the time elapsed till clotting occurs. FVIII knockout mice were injected with phosphate buffered saline (PBS control) or recombinant AAV virions containing SEQ ID NO: 4 driving expression of a FVIII transgene. The rAAV virions were injected at two different doses: $3^{11}$ gc/kg or $3^{12}$ gc/kg. Three weeks after the injections, the treated FVIII-knockout mice were tail clipped and time and blood volume loss till clotting were measured. A group of non-knockout mice were also tail clipped and assessed for blood volume and time till clotting. As shown in FIG. 5A, the PBS treated FVIII knockout mice lost more than double the volume of blood than the untreated non-knockout mice. However, the rAAV treated FVIII knockout mice lost less blood than the PBS treated mice. At the higher rAAV dose, the treated mice lost the same blood volume as the untreated non-knockout mice. Similar results were seen for the bleeding time assay, as illustrated in FIG. 5B. While the lower rAAV dose did not show an effect on bleeding time, the higher dose of rAAV containing SEQ ID NO: 4 operably linked to FVIII reduced the bleeding time almost to the time for the non-knockout mice.

Example 6

Gene Therapy Treatment of a Blood Clotting Disorder

Figure 8:
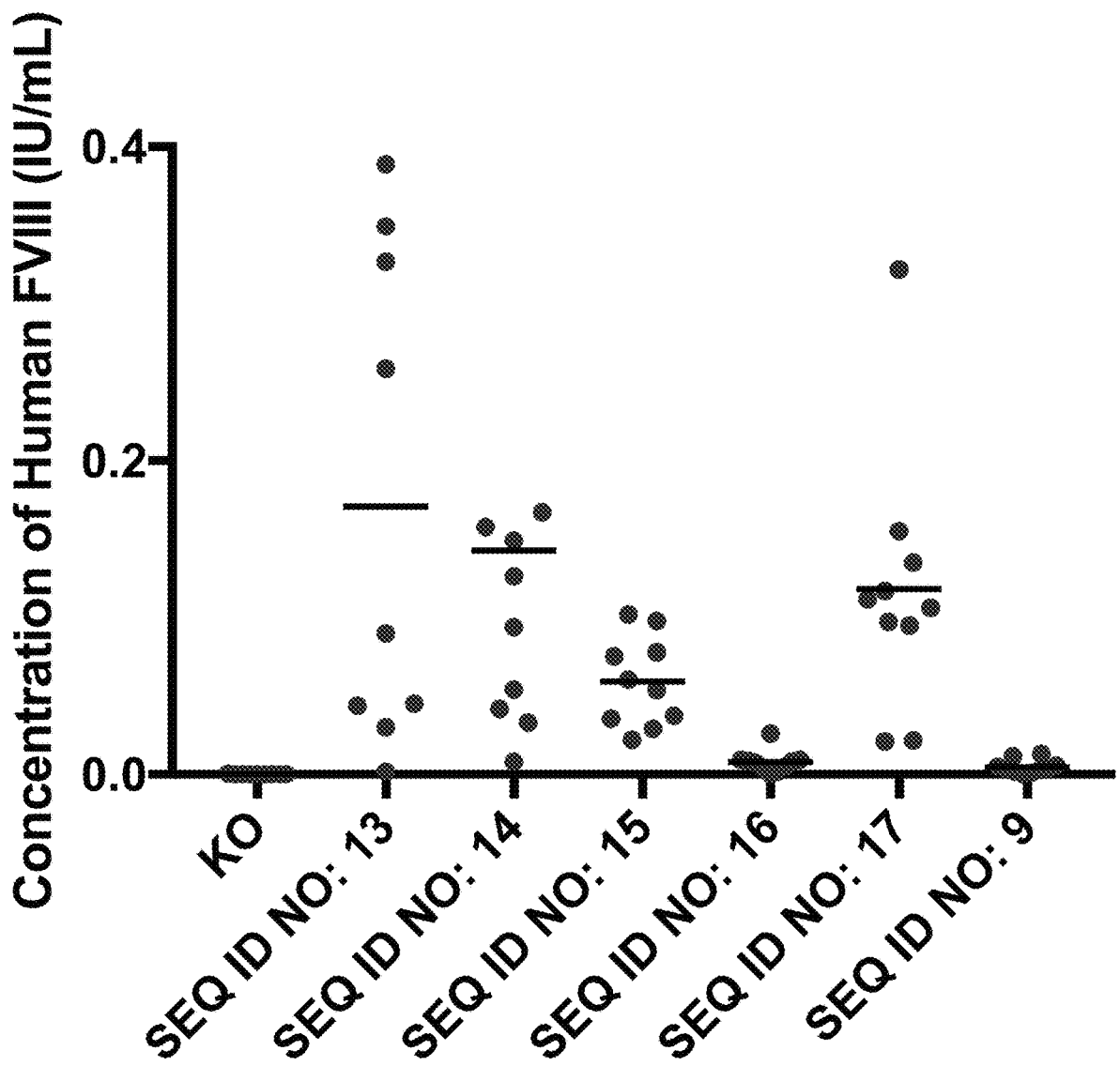
FIG. 8 illustrates the concentration of human FVIII (IU/mL) expressed in mice treated with various expression cassettes of this disclosure, e.g., expression cassettes comprising any one of regulatory elements SEQ ID NOs: 13-17, as compared to the untreated knockout mouse and SEQ ID NO: 9 (UCL-HLP).

FVIII knockout mice (as described in Example 5) were injected with phosphate buffered saline or recombinant AAV virions containing each of SEQ ID NOs: 13-17 driving the expression of FVIII, or a control virion containing SEQ ID NO: 9 (UCL-HLP) driving the expression of FVIII. FIG. 8 illustrates the concentrations of FVIII in blood three weeks after the transfection for untreated knockout mice (KO) and the mice treated with the various virions. The virions containing SEQ ID NO 13, SEQ ID NO: 14, or SEQ ID NO: 17 resulted in the highest expression of FVIII in vivo; SEQ ID NO: 15 resulted in moderate expression of FVIII as compared to the other regulatory elements; and SEQ ID NO: 16 resulted in low expression of FVIII as compared to the other sequences. However, SEQ ID NO: 16 still resulted in FVIII concentration of about 2 fold higher than with the UCL-HLP promoter.

Figure 9:
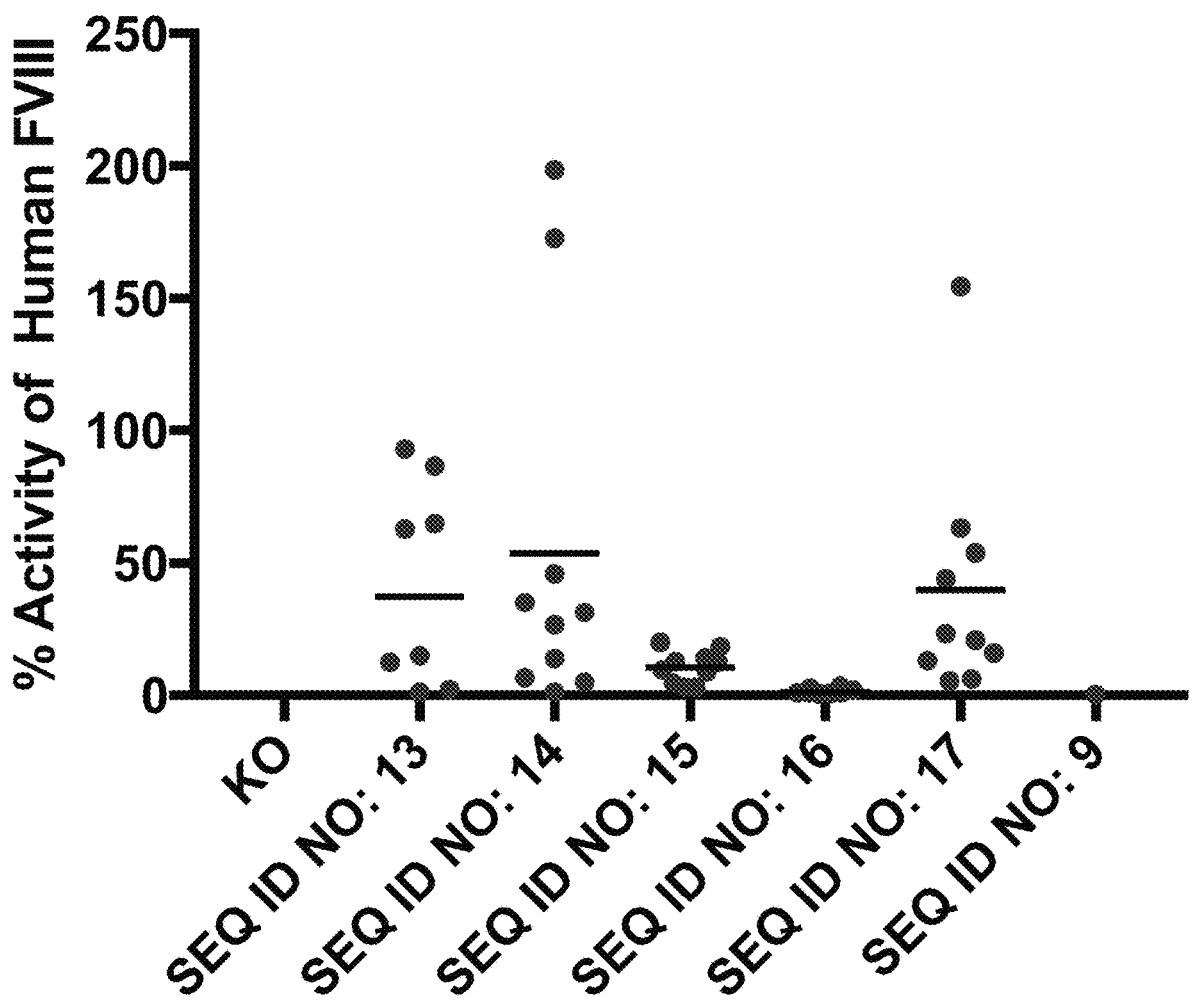
FIG. 9 illustrates the percent activity of human FVIII in mice treated with various expression cassettes of this disclosure, wherein SEQ ID NOs: 13-17 refer to a regulatory element.

Activity of the expressed FVIII was also assayed, as described in Example 3, as illustrated in FIG. 9 and TABLE 4. Activity levels from the different virions followed the same pattern as the expression levels.

TABLE 4

Activity of FVIII in Blood of Transfected Mice

|  | KO | SEQ ID NO: 13 | SEQ ID NO: 14 | SEQ ID NO: 15 | SEQ ID NO: 16 | SEQ ID NO: 17 | SEQ ID NO: 9 |
| --- | --- | --- | --- | --- | --- | --- | --- |
| Activity level of FVIII (% of Wildtype) in the different mice | −1.4019 | −1.1497 | 172.7369 | 19.9399 | 1.0077 | 5.2719 | −0.7564 |
|  | −1.412 | 93.1133 | 46.0407 | 14.038 | 0.8576 | 6.1928 | −0.4091 |
|  | −1.0884 | 62.7729 | 198.6102 | 3.0212 | 0.8175 | 20.677 | −0.2897 |
|  | −1.9783 | 2.2538 | 4.9381 | 9.5587 | 0.6174 | 23.1995 | −0.7022 |
|  | −2.1097 | 86.574 | 6.5522 | 12.6458 | 2.6694 | 12.9859 | −0.8216 |
|  | −1.8427 | 14.8857 | 35.0801 | 4.5446 | 3.4701 | 154.5709 | −0.4308 |
|  | −1.9392 | 64.9174 | 13.806 | 12.3936 | 2.0187 | 53.9879 | 0.3508 |
|  | −1.6585 | 12.4836 | 31.4121 | 2.9909 | −0.8641 | 15.8733 | −0.7347 |
|  | −1.5796 | 1.2449 | 26.6502 | 18.2246 | −0.794 | 44.1145 | −0.5285 |
|  |  |  | 1.2355 | 8.8654 | 1.0177 | 63.181 | −0.192 |
| Average | −1.6678 | 37.4551 | 53.7062 | 10.62227 | 1.0818 | 40.00547 | −0.45142 |

Three weeks after the injections, the treated FVIII knockout mice were tail clipped and time and blood volume till clotting were measured. A group of non-knockout mice were also tail clipped and assessed for blood volume and time till clotting. As illustrated in FIG. 10 and TABLE 5, the PBS treated FVIII knockout mice lost more than double the volume of blood than the untreated non-knockout mice (or WT mice). However, the rAAV treated FVIII knockout mice lost less blood than the PBS treated mice. The mice which received the virion containing SEQ ID NO: 17 lost similar blood volume as the untreated non-knockout mice. Similar results were observed for the bleeding time assay, as shown in FIG. 11 and TABLE 6. The bleeding time for mice treated with virions comprising SEQ ID NO: 15 showed the strongest reduction in bleeding time and blood loss.

TABLE 5

Blood Volume Lost Before Clotting in Mice Transfected With Different Virions

|  | KO | SEQ ID NO: 13 | SEQ ID NO: 14 | SEQ ID NO: 15 | SEQ ID NO: 16 | SEQ ID NO: 17 | SEQ ID NO: 9 | WT |
| --- | --- | --- | --- | --- | --- | --- | --- | --- |
| Blood volume lost from different mice (g) | 0.0814 | 0.3264 | 0.1107 | 0.0223 | 0.3606 | −0.0114 | 0.5145 | 0.0447 |
|  | 0.4122 | 0.05 | 0.1479 | 0.1471 | 0.1367 | 0.0145 | 1.1232 | 0.0001 |
|  | −0.0522 | 0.6822 | 0.2897 | 0.0136 | 0.6372 | 0.0341 | 0.4819 | −0.0357 |
|  | 0.6397 | 0.0178 | 0.0526 | 0.0449 | 0.219 | 0.0575 | 0.486 | 0.0836 |
|  | 0.3505 | 0.0356 | 0.2819 | 0.3934 | 0.2606 | 0.0963 | 0.4708 | 0.1065 |
|  | 0.4982 | 0.1057 | 0.1665 | 0.0331 | 0.201 | 0.0837 | 0.0806 | 0.0693 |
|  | −0.0116 | 0.2129 | 0.0934 | 0.0919 | 0.0827 | 0.0288 | 0.34 | 0.061 |

TABLE 5-continued

Blood Volume Lost Before Clotting in Mice Transfected With Different Virions

|  | KO | SEQ ID NO: 13 | SEQ ID NO: 14 | SEQ ID NO: 15 | SEQ ID NO: 16 | SEQ ID NO: 17 | SEQ ID NO: 9 | WT |
|---|---|---|---|---|---|---|---|---|
|  | 0.1827 | 0.0133 | 0.197 | 0.0748 | 0.438 | 0.103 | 0.2327 | 0.0423 |
|  | 0.2793 | 0.0573 | 0.0355 | 0.0782 | 0.0275 | 0.0223 | 0.4931 | 0.0919 |
|  |  |  | 0.1657 | 0.0456 | 0.1477 | 0.191 | 0.0281 | 0.1329 |
| Average | 0.264 | 0.167 | 0.154 | 0.094 | 0.251 | 0.062 | 0.425 | 0.060 |

TABLE 6

Bleeding Time Till Clotting for Mice Transfected With Different Virions

|  | KO | SEQ ID NO: 13 | SEQ ID NO: 14 | SEQ ID NO: 15 | SEQ ID NO: 16 | SEQ ID NO: 17 | SEQ ID NO: 9 | WT |
|---|---|---|---|---|---|---|---|---|
| Bleeding time for different mice, (mins) | 6.42 | 13.25 | 3.28 | 6.78 | 11.22 | 2.38 | 27.63 | 4.55 |
|  | 25.23 | 8.3 | 11.02 | 9.5 | 15.6 | 1.95 | 26.88 | 0.38 |
|  | 0 | 28.4 | 14.78 | 1.28 | 24.27 | 18.93 | 20.4 | 0.63 |
|  | 26.17 | 0.92 | 2.52 | 3.62 | 27.5 | 17.73 | 20.2 | 5.15 |
|  | 19.98 | 4.22 | 19.02 | 13.28 | 19.17 | 6.7 | 30 | 4.6 |
|  | 30 | 16.95 | 3.27 | 1.15 | 23.5 | 9.95 | 13.15 | 2.13 |
|  | 14.65 | 30 | 6.38 | 14.1 | 13.23 | 3.87 | 29.67 | 3.7 |
|  | 21.93 | 7.58 | 8.17 | 1.58 | 22.45 | 21.43 | 14.43 | 4.68 |
|  | 22.35 | 17.82 | 4.73 | 11.52 | 12.43 | 8.5 | 30 | 2.33 |
|  |  |  | 14.6 | 0.35 | 13.32 | 13.33 | 1.66 | 8.63 |
| Average | 18.52 | 14.16 | 8.13 | 6.97 | 18.81 | 10.16 | 23.59 | 3.12 |

Example 7

ATP7B Expression in Liver

C57BL6/J mice were intravenously injected with AAV8 vectors containing ATP7B under the control of SEQ ID NO: 13. Two weeks after viral delivery, livers were harvested. Liver punches were disrupted and homogenized in 600 ul of RLT supplemented with 10 ul/mL beta-mercaptoethanol, and RNA was extracted using an RNeasy Mini kit (Qiagen) in accordance with manufacturer's protocols, including on-column DNase treatment. For each sample, RNA (3 ug) was reverse transcribed with Superscript IV (Invitrogen), using OligoDT primers (65° C. 5 m, 55° C. 10 m, 85° C. 10 m). Primers against human ATP7B (5'-CAT-TCCAGGACTGTCCATTCT-3' (SEQ ID NO: 18); 5'-GGCCTGAACGTAGAAGTACCA-3' (SEQ ID NO: 19)), and GAPDH (5'ACCACAGTCCATGCCATCAC-3' (SEQ ID NO: 20); 5'-TCCACCACCCTGTTGCTGTA-3' (SEQ ID NO: 21)) were verified with standard curves to ensure reliability, and used for qPCR (Phusion, SYBR Green) under the following amplification conditions: (98° C. 2 m, 40×[98° C. 10 s, 67° C. 30 s, 92° C. 15 s]). ATP7B expression was normalized to GAPDH and presented as fold change over baseline using the delta-delta Ct method. As illustrated in FIG: 12, and TABLE 7, SEQ ID NO: 13 drove expression of ATP7B in the liver at three different doses, and showed a dose response with the highest viral dose resulting in the highest ATP7B expression.

TABLE 7

ATP7B Expression in Liver of Transfected Mice

|  | Buffer | SEQ ID: 13; 1E10 gc/mouse | SEQ ID: 13; 1E11 gc/mouse | SEQ ID: 13; 1E12 gc/mouse |
|---|---|---|---|---|
| Relative ATP7B expression in liver of transfected mice (log2) | 3.214475452 | 111.7850412 | 87.30041862 | 5639.103082 |
|  | 1.992504985 | 7.333913922 | 375.1308235 | 6142.385453 |
|  | 2.857162979 | 20.64780715 | 306.8202728 | 1207.591395 |
|  | 3.20705701 | 27.24494487 | 183.2814118 | 4273.64098 |
|  | 0.339445061 | 1.698879272 | 3.813855015 | 2376.435176 |
|  | 0.45520343 | 0.501590988 | 2.734448707 | 1352.347313 |
|  | 0.405540152 |  | 19.17626705 | 26577.47941 |
|  | 0.271919214 |  | 0.5721968 | 128.407293 |
| Average | 1.592913535 | 28.20202957 | 122.3537118 | 5962.17376 |

Example 7 illustrates expression cassettes comprising one or more REs disclosed herein operably linked to a ATP7B transgene can be used to treat a disorder or condition associated with ATP7B deficiency, e.g., Wilson's disease, in an animal, a mammal, or a human subject in need thereof. Further, such expression cassettes can be delivered systemically in vivo using rAAV8, e.g., via intravenous injection or infusion.

Example 8

High EGFP Transcription in Liver

Figure 13:
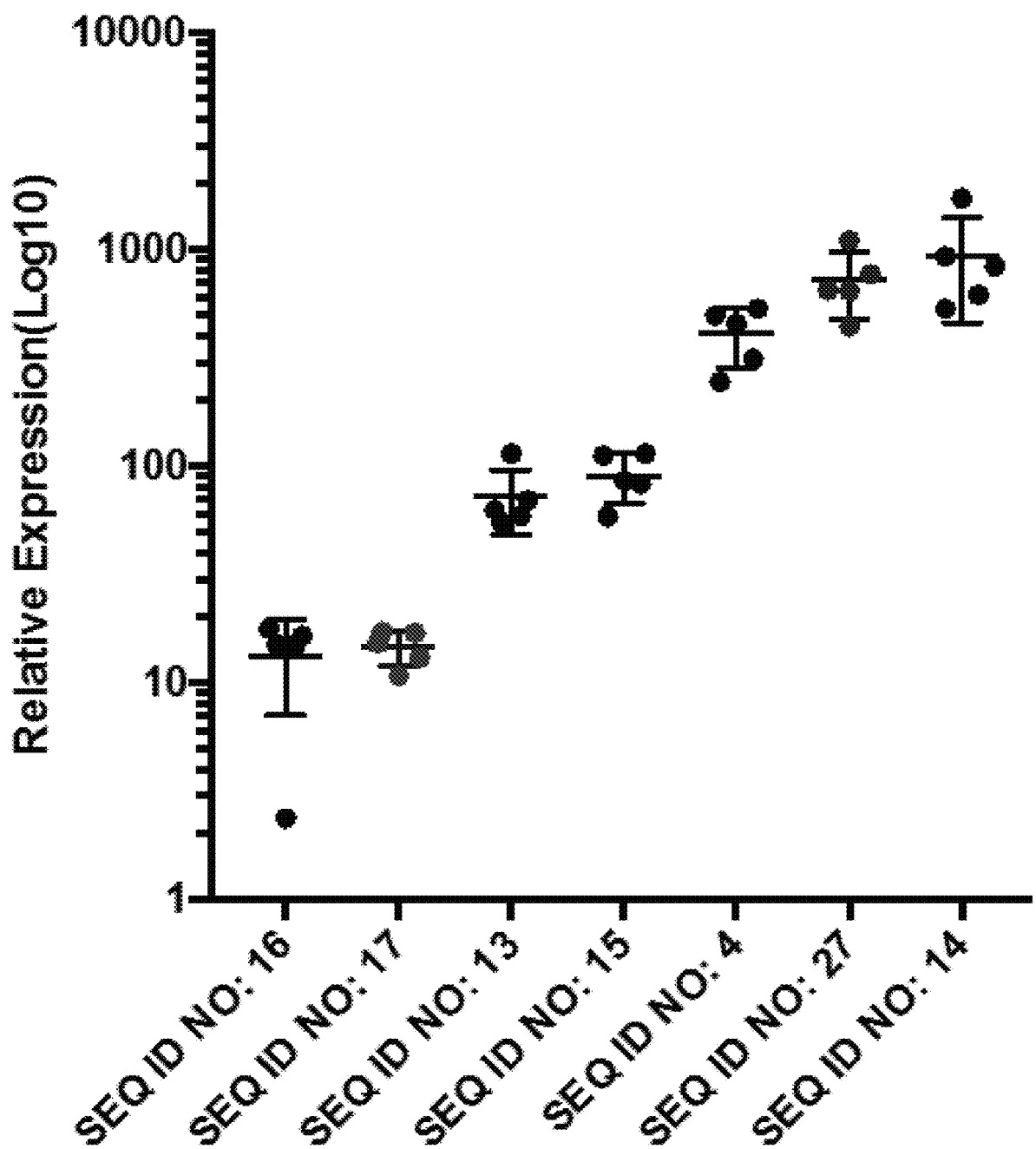
FIG. 13 illustrates the relative expression of EGFP (Log 10) in mice treated with an expression cassette comprising a regulatory element having a sequence of SEQ ID NO: 4, 13, 14, 15, 16, 17, or 27 and administered at a dose of 5E11 gc/mouse. The data showed the REs resulted in elevated levels of EGFP expression, as measured by RNA transcripts, in the liver of the mice in vivo.

C57BL6/J mice were intravenously injected with AAV8 vectors containing EGFP under the control of various REs:

SEQ ID NO: 4, 13, 14, 15, 16, 17, and 27. Each AAV8 vector was administered at a dose of 5×10¹¹ gc/mouse. Two weeks after viral delivery, livers were harvested. Liver punches were disrupted and homogenized in 600 ul of RLT supplemented with 10 ul/mL beta-mercaptoethanol, and RNA was extracted using an RNeasy Mini kit (Qiagen) in accordance with manufacturer's protocols, including on-column DNase treatment. For each sample, RNA (3 ug) was reverse transcribed with Superscript IV (Invitrogen), using OligoDT primers (65° C. 5 m, 55° C. 10 m, 85° C. 10 m). Primers against EGFP (5'-GCTACCCCGACCACATGAAG-3' (SEQ ID NO: 42); 5'-TCTTGTAGTTGCCGTCGTCC-3' (SEQ ID NO: 43), and GAPDH (SEQ ID NO: 20 and SEQ ID NO: 21) were used for qPCR (Phusion, SYBR Green) under the following amplification conditions: (98° C. 2 m, 40×[98° C. 10 s, 65° C. 30 s, 92° C. 15 s]). EGFP expression was normalized to GAPDH and presented as fold change over baseline using the delta-delta Ct method (FIG. 13). As illustrated in FIG. 13, each of the REs tested increased EGFP expression, as measured by RNA transcripts, in the liver. Further, SEQ ID NO: 4, SEQ ID NO: 27, and SEQ ID NO: 14 resulted in comparable levels of EGFP.

Example 8 illustrates that the relatively short REs of this disclosure can results in high levels of transgene expression in the liver, as measured by RNA transcripts.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Various embodiments of this disclosure are defined with reference to the following numbered clauses.

1. An expression cassette comprising a regulatory element operably linked to a therapeutic transgene, wherein the regulatory element comprises one or more of (i) SEQ ID NOs: 1-2, 13-17, and 22-41; or (ii) sequences having at least 80%, 85%, 90%, or 95% sequence identity to any one of (i).
2. The expression cassette of clause 1, wherein the regulatory element is non-naturally occurring.
3. The expression cassette of any one of clauses 1-2, wherein the regulatory element comprises an intronic sequence.
4. The expression cassette of any one of clauses 1-3, wherein the regulatory element is located between a promoter and the therapeutic transgene.
5. The expression cassette of any one of clauses 1-2, wherein the regulatory element comprises a promoter sequence.
6. The expression cassette of clause 5, wherein the regulatory element is the only promoter in the cassette.
7. The expression cassette of any one of clauses 1-6, wherein the regulatory element is relatively short.
8. The expression cassette of any one of clauses 1-6, wherein the regulatory element is no more than 100 bp.
9. The expression cassette of any one of clauses 1-8, wherein the regulatory element is no more than 60 bp.
10. The expression cassette of any one of clauses 1-9, wherein the regulatory element is no more than 50 bp.
11. The expression cassette of any one of clauses 1-10, wherein the expression cassette is part of a rAAV.
12. The expression cassette of clause 11, wherein the rAAV is rAAV8.
13. The expression cassette of any one of clauses 1-10, wherein the expression cassette is part of an adenovirus.
14. The expression cassette of any one of clauses 1-10, wherein the expression cassette is part of a lentivirus.
15. The expression cassette of any one of clauses 1-14, wherein the therapeutic transgene is larger than 1 kb, 1.5 kb, 2 kb, 2.5 kb, 3 kb, 3.5 kb, 4 kb, 4.5 kb, 5 kb, 5.5 kb, 6 kb, 6.5 kb, 7 kb, or 7.5 kb.
16. The expression cassette of any one of clauses 1-14, wherein the therapeutic transgene is ATP7B, or a variant or a functional fragment thereof.
17. The expression cassette of any one of clauses 1-14, wherein the therapeutic transgene is ATP7A, or a variant or a functional fragment thereof.
18. The expression cassette of any one of clauses 1-14, wherein the therapeutic transgene is ATP8B1, or a variant or a functional fragment thereof.
19. The expression cassette of any one of clauses 1-14, wherein the therapeutic transgene is ABCB4, or a variant or a functional fragment thereof.
20. The expression cassette of any one of clauses 1-14, wherein the therapeutic transgene is ABCB11, or a variant or a functional fragment thereof.
21. The expression cassette of any one of clauses 1-14, wherein the therapeutic transgene is CDKL5, or a variant or a functional fragment thereof.
22. The expression cassette of any one of clauses 1-14, wherein the therapeutic transgene is CNTNAP2, or a variant or a functional fragment thereof.
23. The expression cassette of any one of clauses 1-14, wherein the therapeutic transgene is ZEB2, or a variant or a functional fragment thereof.
24. The expression cassette of any one of clauses 1-14, wherein the therapeutic transgene is Factor V, or a variant or a functional fragment thereof.
25. The expression cassette of any one of clauses 1-14, wherein the therapeutic transgene is Factor VIII, or a variant or a functional fragment thereof.
26. The expression cassette of any one of clauses 1-14, wherein the therapeutic transgene is Factor IX, or a variant or a functional fragment thereof.
27. The expression cassette of any one of clauses 1-14, wherein the therapeutic transgene is Factor X, or a variant or a functional fragment thereof.
28. The expression cassette of any one of clauses 1-14, wherein the therapeutic transgene is a blood clotting factor.
29. The expression cassette of clause 28, wherein the blood clotting factor is any one of Factor 1, 2, 3, 4, 5, 6, 7, 8, 9, 10, 11, or 12, or a variant or a functional fragment thereof.
30. The expression cassette of any one of clauses 1-14, wherein the therapeutic transgene is a DNA binding protein.
31. The expression cassette of clause 30, wherein the DNA binding protein is a transcriptional modulator of an endogenous gene.
32. The expression cassette of clause 31, wherein the transcriptional modulator is a transcriptional activator.
33. The expression cassette of clause 32, wherein the endogenous gene is under-expressed in vivo.

34. The expression cassette of any one of clauses 30-33, wherein the endogenous gene is associated with a liver disease or condition.

35. The expression cassette of any one of clauses 30-33, wherein the endogenous gene is associated with progressive familial intrahepatic cholestasis (PFIC) type 1, type 2, or type 3.

36. The expression cassette of any one of clauses 30-33, wherein the endogenous gene is associated with autism spectrum disorder.

37. The expression cassette of any one of clauses 30-33, wherein the endogenous gene is associated with hemophilia.

38. The expression cassette of any one of clauses 30-33, wherein the endogenous gene is associated with Wilson's disease.

39. The expression cassette of any one of clauses 30-33, wherein the endogenous gene is associated with Menkes disease or occipital horn syndrome.

40. The expression cassette of any one of clauses 30-33, wherein the endogenous gene is CDKL5.

41. The expression cassette of clause 35, wherein the endogenous gene is ABCB11, which is associated with progressive familial intrahepatic cholestasis is type 2 (PFIC2).

42. The expression cassette of clause 35, wherein the endogenous gene is ATP8B1, which is associated with progressive familial intrahepatic cholestasis is type 1 (PFIC1).

43. The expression cassette of clause 35, wherein the endogenous gene is ABCB4, which is associated with progressive familial intrahepatic cholestasis is type 3 (PFIC3).

44. The expression cassette of clause 36, wherein the endogenous gene is CNTNAP2, which is associated with autism spectrum disorder.

45. The expression cassette of clause 37, wherein the endogenous gene is Factor VIII or a variant thereof, which is associated with hemophilia A.

46. The expression cassette of clause 37, wherein the endogenous gene is Factor IX or a variant thereof, which is associated with hemophilia B.

47. The expression cassette of clause 37, wherein the endogenous gene is any one of Factor 1, 2, 3, 4, 5, 6, 7, 8, 9, 10, 11, or 12.

48. The expression cassette of clause 38, wherein the endogenous gene is ATP7B or a variant thereof, which is associated with Wilson's disease.

49. The expression cassette of clause 39, wherein the endogenous gene is ATP7A or a variant thereof, Menkes disease or occipital horn syndrome.

50. The expression cassette of any one of clauses 1-14, wherein the therapeutic transgene is a gene editing protein.

51. The expression cassette of clause 50, wherein the gene editing protein is a Cas protein.

52. The expression cassette of clause 51, further comprising a guide RNA that targets the Cas protein to a genomic locus comprising an endogenous gene.

53. The expression cassette of clause 52, wherein the endogenous gene comprises a mutation or is expressed abnormally.

54. The expression cassette of clause 53, wherein the mutation results in an under-expression of the endogenous gene.

55. The expression cassette of any one of clauses 51-54, wherein the endogenous gene is ATP7A, ATP7B, ATP8B1, ABCB4, ABCB11, CDKL5, CNTNAP2, ZEB2, or Factor VIII.

56. The expression cassette of any one of clauses 51-54, wherein the endogenous gene is Factor 1, 2, 3, 4, 5, 6, 7, 8, 9, 10, 11, or 12.

57. The expression cassette of any one of clauses 1-56, wherein the regulatory element results in increased expression of the therapeutic transgene or the endogenous gene by at least 1.5 fold, at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 50 fold, at least 100 fold, at least 200 fold, at least 300 fold, at least 400 fold, at least 500 fold, at least 600 fold, at least 700 fold, at least 800 fold, at least 900 fold, or at least 1000 fold as compared to an expression cassette without the regulatory element.

58. The expression cassette of clause 57, wherein the increased expression is determined by amount of RNA transcripts from the therapeutic transgene or the endogenous using a PCR assay.

59. The expression cassette of clause 57, wherein the increased expression is determined by level of protein synthesized from the therapeutic transgene or the endogenous gene using an immunoassay.

60. The expression cassette of any one of clauses 30-56, wherein the regulatory element results in increased expression of the endogenous gene by at least 1.5 fold, at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 50 fold, at least 100 fold, at least 200 fold, at least 300 fold, at least 400 fold, at least 500 fold, at least 600 fold, at least 700 fold, at least 800 fold, at least 900 fold, or at least 1000 fold as compared to an expression cassette without the regulatory element.

61. The expression cassette of any one of clauses 30-56, wherein the regulatory element results in increased expression of the endogenous gene at a level comparable to expression of the endogenous gene in a healthy subject.

62. The expression cassette of any one of clauses 60-61, wherein the increased expression is determined by amount of RNA transcripts from the endogenous gene using a PCR assay.

63. The expression cassette of any one of clauses 60-61, wherein the increased expression is determined by level of protein synthesized from the endogenous gene using an immunoassay.

64. A method of treating Wilson's disease, comprising administering an expression cassette according to clause 1-16, 30-34, 38, 48, 50-55, and 57-63.

65. A method of treating a genetic defect in ATP7B, comprising administering the expression cassette according to any one of clauses 1-16, 30-34, 38, 48, 50-55, and 57-63.

66. A method of treating a blood clotting disorder, comprising administering the expression cassette according to any one of clauses 1-15, 24-34, 37, 45-47, and 50-63.

67. A method of treating a haploinsufficiency or a genetic defect, comprising administering the expression cassette according to any one of clauses 1-66.

68. The method of clause 67, wherein the therapeutic transgene or the endogenous gene is ATP7A, ATP7B, ATP8B1, ABCB4, ABCB11, CDKL5, CNTNAP2, ZEB2, or Factor VIII, or a variant thereof.
69. The method of clause 67, wherein the therapeutic transgene or the endogenous gene is Factor 1, 2, 3, 4, 5, 6, 7, 8, 9, 10, 11, or 12, or a variant thereof.
70. The method of clause 67 or 68, wherein the transgene is ATP7B, or a variant or a functional fragment thereof.
71. The method of clause 67 or 68, wherein the transgene is a transcriptional modulator that modulates expression of an endogenous gene.
72. The method of clause 71, wherein the endogenous gene is ATP7A, ATP7B, ATP8B1, ABCB4, ABCB11, CDKL5, CNTNAP2, ZEB2, or Factor VIII, or a variant thereof.
73. A method of producing a recombinant protein or a biologic, comprising introducing the expression cassette according to any one of clauses 1-63 into a cell.
74. An AAV expression cassette comprising a human-derived regulatory element of no more than 120 bp operably linked to a transgene of at least 3 kb, wherein the regulatory element results in increased transgene expression by at least 1.5 fold, at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 50 fold, at least 100 fold, at least 200 fold, at least 300 fold, at least 400 fold, at least 500 fold, at least 600 fold, at least 700 fold, at least 800 fold, at least 900 fold, or at least 1000 fold as compared to expression of the transgene when operably linked to a CMV promoter.
75. An AAV expression cassette comprising a relatively short human-derived regulatory element operably linked to a transgene of at least 3 kb, wherein the relatively short regulatory element results in increased transgene expression by at least 1.5 fold, at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 50 fold, at least 100 fold, at least 200 fold, at least 300 fold, at least 400 fold, at least 500 fold, at least 600 fold, at least 700 fold, at least 800 fold, at least 900 fold, or at least 1000 fold as compared to a comparable expression cassette without the regulatory element.
76. The AAV expression cassette of clause 74 or 75, wherein the regulatory element comprises (i) SEQ ID NO: 1-2, 13-17, and 22-41; (ii) a combination thereof; or (iii) or sequence having at least 80%, 85%, 90%, or 95% sequence identity to any one of (i) and (ii).
77. The AAV expression cassette of any one of clauses 74-76, wherein the increased transgene expression is at least 50 fold as compared to expression of the transgene when operably linked to a CMV promoter.
78. The AAV expression cassette of clause 77, wherein the increased transgene expression is at least 100 fold.
79. The AAV expression cassette of any one of clauses 74-78, wherein the regulatory element exhibits a size-normalized expression activity that is at least 1.5 fold, at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 50 fold, or at least 100 fold as compared to size-normalized expression activity of a CMV promoter operably linked to the transgene.
80. The AAV expression cassette of any one of clauses 74-79, wherein the increased transgene expression occurs in at least 2 cell types.
81. The AAV expression cassette of clause 80, wherein the at least 2 cell types are selected from the group consisting of: kidney cells, epithelial cells, neurons, and liver cells.
82. The AAV expression cassette of any one of clauses 74-81, wherein the regulatory element comprises any one or more of SEQ ID NOs: 22-41, and wherein no other promoter sequences are present in the expression cassette.
83. The AAV expression cassette of any one of clauses 74-82, wherein the regulatory element comprises SEQ ID NO: 1 or SEQ ID NO: 2.
84. The AAV expression cassette of clause 83, wherein the regulatory element is located downstream of a promoter.
85. The AAV expression cassette of any one of clauses 74-84, wherein the regulatory element is located upstream of the transgene.
86. The AAV expression cassette of any one of clauses 74-85, wherein the transgene is ATP7A; ATP7B; ATP8B1; ABCB4; ABCB11; CDKL5; CNTNAP2; ZEB2; Factor 1, 2, 3, 4, 5, 6, 7, 8, 9, 10, 11, or 12; or a variant or a functional fragment thereof.
87. The AAV expression cassette of clause 86, wherein the transgene is ATP7B, or a variant or a functional fragment thereof.
88. The AAV expression cassette of clause 86, wherein the transgene is FVIII, or a variant or a functional fragment thereof.
89. The AAV expression cassette of any one of clauses 74-85, wherein the transgene is a gene editing protein.
90. The AAV expression cassette of clause 89, wherein the gene editing protein is Cas.
91. The AAV expression cassette of any one of clauses 74-85, wherein the transgene is a DNA binding protein.
92. The AAV expression cassette of clause 91, wherein the DNA binding protein is a transcriptional activator that increases expression of an endogenous gene.
93. The AAV expression cassette of clause 91, wherein the DNA binding protein is a transcriptional repressor that decreases expression of an endogenous gene.
94. The AAV expression cassette of clause 92, wherein the transcriptional activator increases expression of ATP7A; ATP7B; ATP8B1; ABCB4; ABCB11; CDKL5; CNTNAP2; ZEB2; or Factor 1, 2, 3, 4, 5, 6, 7, 8, 9, 10, 11, or 12, or a variant thereof.
95. The AAV expression cassette of clause 94, wherein the transcriptional activator increases expression of an endogenous ATP7A.
96. The AAV expression cassette of clause 94, wherein the transcriptional activator increases expression of an endogenous ATP7B.
97. The AAV expression cassette of clause 94, wherein the transcriptional activator increases expression of an endogenous ATP8B1.
98. The AAV expression cassette of clause 94, wherein the transcriptional activator increases expression of an endogenous ABCB4.
99. The AAV expression cassette of clause 94, wherein the transcriptional activator increases expression of an endogenous ABCB11.
100. The AAV expression cassette of clause 94, wherein the transcriptional activator increases expression of an endogenous FVIII.
101. The AAV expression cassette of any one of clauses 74-100, wherein the AAV is selected from the group consisting of: AAV1, AAV2, AAV3, AAV3b, AAV4, AAV5, AAV6, AAV7, AAV8, AAV9, AAV10, AAV11, AAV12, AAV-DJ, and scAAV.

102. The AAV expression cassette of clause 101, wherein the AAV is AAV8.

103. A method of producing a recombinant protein, the method comprising operably linking a sequence encoding the protein with one or more of (i) SEQ ID NO: 1-2, 13-17, and 22-41; (ii) a combination thereof; or (iii) sequences having at least 80%, 85%, 90%, or 95% sequence identity to any one of (i) and (ii).

104. The method of clause 103, wherein the sequence encoding the protein is more than 1 kb, 1.5 kb, 2 kb, 2.5 kb, 3 kb, 3.5 kb, 4 kb, 4.5 kb, 5 kb, 5.5 kb, 6 kb, 6.5 kb, 7 kb, or 7.5 kb.

105. A method of treating a liver disease or condition, comprising administering a gene therapy comprising a therapeutic transgene operably linked to one or more regulatory elements selected from (i) SEQ ID NO: 1-2, 13-17, and 22-41; (ii) a combination thereof; or (iii) sequences having at least 80%, 85%, 90%, or 95% sequence identity to any one of (i) and (ii).

106. The method of clause 105, wherein the liver disease or condition is Wilson's disease.

107. The method of clause 105, wherein the liver disease or condition is a blood clotting disorder.

108. The method of clause 105, wherein the transgene is ATP7A or ATP7B, or a variant or a functional fragment thereof.

109. The method of clause 105, wherein the transgene is Factor 1, 2, 3, 4, 5, 6, 7, 8, 9, 10, 11, 12, or a variant or a functional fragment thereof.

110. The method of clause 109, wherein the transgene is Factor 8, or a variant or a functional fragment thereof.

111. The method of any one of clauses 105-110, wherein the regulatory elements result in increased transgene expression in at least 2 cell types.

112. The method of any one of clauses 150-110, wherein the regulatory elements result in increased transgene expression in at least 3 cell types.

113. The method of any one of clauses 105-112, wherein the regulatory elements result in increased transgene expression in hepatocytes.

114. The method of any one of clauses 105-113, wherein the regulatory elements result in increased transgene expression at a level that is at least 2 fold as compared to expression of the transgene when operably linked to a CMV promoter.

115. The method of any one of clauses 105-114, wherein the gene therapy utilizes AAV.

116. The method of clause 115, wherein the AAV is AAV8.

117. The method of any one of clauses 105-114, wherein the gene therapy utilizes an adenovirus.

118. The method of any one of clauses 105-114, wherein the gene therapy utilizes a lentivirus.

119. An expression vector comprising: a human-derived regulatory element having less than or equal to 100 bp operably linked to a transgene, wherein the regulatory element increases global expression of the transgene by at least two fold as compared to a second expression vector without the regulatory element.

120. The expression vector of clause 119, wherein the second expression vector comprises the transgene operably linked to a CMV promoter.

121. An expression vector comprising a human-derived regulatory element having less than or equal to 100 bp operably linked to a transgene, whereby expression of the transgene is higher than that of the same transgene expressed by a CMV promoter, super core promoter, TTR promoter, Proto 1 promoter, UCL-HLP promoter, or CMVe promoter.

122. The expression vector of clause 121, wherein the expression of the transgene is higher than that of the same transgene expressed by a UCL-HLP promoter.

123. An expression vector comprising a human-derived regulatory element operably linked to a transgene, wherein a protein encoded by the transgene has (i) a concentration >1.0 IU/mL as measured by an ELISA assay configured to detect the transgene; or (ii) >25% activity as measured by a Coatest assay.

124. A vector comprising a human-derived regulatory element having a sequence less than or equal to 100 bp in size operably linked to a transgene not found in context with the regulatory element in a cell or in vivo.

125. The vector of any one of clauses 119-124, wherein the regulatory element is an intronic sequence.

126. The vector of clause 125, wherein the regulatory element is SEQ ID NO: 1 or SEQ ID NO: 2, or a sequence having at least 80%, 85%, 90%, or 95% homology thereto.

127. The expression vector or cassette of any one of clauses 1-63, 74-102, and 119-126, wherein use of a luciferase as the transgene results in global expression that is greater than $1 \times 10^8$ photons/sec as measured in whole mice.

128. The expression vector or cassette of clause 127, wherein the activity or transgene expression corresponds to a dose of 16 μg of expression vector per mouse.

129. The expression vector or cassette of clause 127, wherein the activity or transgene expression corresponds to a dose of 12 μg of expression vector per mouse.

130. The expression vector or cassette of any one of clauses 1-63, 74-102, and 119-129, wherein the endogenous version of the transgene is not linked to the regulatory element in vivo.

131. The expression vector or cassette of clause 127, wherein the global expression of the transgene is at a level greater than expression of the transgene using a vector or cassette with a regulatory element selected from the group consisting of: a CMV promoter, a CMVe promoter, a super core promoter, TTR promoter, Proto 1 promoter, and a UCL-HLP promoter.

132. The expression vector or cassette of any one of clauses 1-63, 74-102, and 119-131, wherein expression is detectable in at least 3, 4, 5, 6, or 7 different cell types in mouse in vivo.

133. The expression vector or cassette of clause 132, wherein the different cell types are selected from the group consisting of: alveolar cells, cardiomyocytes, epithelial cells, hepatocytes, intestinal cells, myocytes, neurons, and renal cells.

134. The expression vector or cassette of any one of clauses 119-133, wherein the regulatory element is an enhancer.

135. The expression vector or cassette of clause 134, further comprising a promoter.

136. The expression vector or cassette of clause 135, wherein the promoter is a CMV promoter, CMV, promoter, super core promoter, TTR promoter, Proto 1 promoter, UCL-HLP promoter, an AAT promoter, a KAR promoter, a EF1α promoter, EFS promoter, or CMVe enhancer/CMV promoter combination.

137. The expression vector of any one of clauses 119-136, further comprising one or more post-transcriptional modification sites.
138. The expression vector of any one of clauses 119-137, wherein the transgene is Cas9.
139. The expression vector of clause 138, wherein the transgene is saCas9.
140. An expression vector comprising a Factor VIII transgene operably linked to a regulatory sequence that is able to drive expression of the Factor VIII to a concentration >1.0 IU/mL as measured by an ELISA assay configured to detect Factor VIII in a cell or in vivo.
141. The expression vector of clause 140, wherein the regulatory sequence is relatively short.
142. The expression vector of clause 140 or 141, wherein the regulatory sequence comprises one or more of SEQ ID NO: 1-2, 13-17, and 22-41, or a combination thereof; or sequences having at least 80%, 85%, 90%, or 95% sequence identity thereto.
143. A viral particle comprising the expression vector of any one of clauses 119-142.
144. The viral particle of clause 143, wherein the viral particle is an AAV.
145. The viral particle of clause 144, wherein the AAV is selected from the group consisting of: AAV1, AAV2, AAV3, AAV3b, AAV4, AAV5, AAV6, AAV7, AAV8, AAV9, AAV10, AAV11, AAV12, AAV-DJ, and scAAV.
146. The viral particle of clause 143, wherein the viral particle is a lentivirus.
147. The viral particle of clause 143, wherein the virus particle is an adenovirus.
148. The expression vector of clause 119-147, wherein the transgene is a therapeutic transgene.
149. The expression vector of clause 148, wherein the therapeutic transgene is Factor VIII, Cas9, a DNA binding protein, hormone, growth or differentiation factor, insulin, growth hormone, VEGF, neurotrophic factor, fibroblast epithelial factor; cytokine, interleukin, lymphokine, tumor necrosis factor, antibody, immunoglobulin, interferon, chimeric T cell receptor; lipoprotein receptor, cystic fibrosis transmembrane regulator, a gene associated with mucopolysaccharidosis type I, II, III, or IV, beta globin or lipoprotein lipase.
150. The expression vector of clause 148, wherein the therapeutic transgene is ATP7A, ATP7B, ATP8B1, ABCB4, ABCB11, or a variant or functional fragment thereof.
151. The expression vector of clause 148, wherein the therapeutic transgene is CDKL5, CNTNAP2, ZEB2, or a variant or functional fragment thereof.
152. A method for delivering a transgene to a plurality of different tissues in an animal comprising administering to said animal an expression vector of any one of clauses 119-151.
153. A method for production of proteins, antibodies, or other biologics, comprising contacting a cell with an expression vector of any one of clauses 119-151.
154. The method of clause 153, wherein the cell is a CHO cell or a HEK293T cell.
155. A method for producing a transgenic animal or plant comprising administering to an animal or plant an expression vector of any one of clauses 119-151.
156. The expression vector of any one of clauses 119-151, wherein the regulatory element is 40-50 bp.
157. The expression vector of any one of clauses 119-151, wherein the regulatory element is 50-60 bp.
158. An expression vector comprising a human-derived regulatory element operably linked to a transgene, wherein a protein encoded by the transgene has (i) a concentration >0.1 IU/mL as measured by an ELISA assay configured to detect the transgene; or (ii) >10% activity as measured by a Coatest assay.
159. An expression vector comprising a human-derived regulatory element having less than or equal to 120 bp operably linked to a transgene, whereby expression of the transgene is higher than that of the same transgene expressed by a UCL-HLP promoter.
160. The expression vector of any one of clauses 158-159, wherein the regulatory element is a promoter.
161. The expression vector of any one of clauses 158-160, wherein the therapeutic transgene is a fusion protein comprising a DNA binding domain and a transcription regulatory domain.
162. An expression cassette comprising a relatively short regulatory element (RE) operably linked to a therapeutic transgene.
163. The expression cassette of clause 162, wherein the relative short RE comprises one or more of (i) SEQ ID NOs: 1-2, 13-17, and 22-41; or (ii) sequences having at least 80%, 85%, 90%, or 95% sequence identity to any one of (i).
164. The method of any one of clauses 64-72 and 105-118, wherein the administering is systemic.
165. The method of clause 164, wherein the administering comprises intravenous injection or infusion in a subject.
166. The method of clause 165, wherein the subject is a human.
167. The method of clause 165, wherein the subject is an animal.

What is claimed is:

1. An expression cassette comprising a regulatory element operably linked to a therapeutic transgene, wherein the regulatory element comprises:
   (i) a sequence selected from the group consisting of SEQ ID NOS: 13-17 and 22-41; or
   (ii) a sequence selected from the group consisting of SEQ ID NO: 1, SEQ ID NO: 2, and a combination of SEQ ID NOS: 1 and 2;

wherein the regulatory element of (ii) is operably linked to a promoter.

2. The expression cassette of claim 1, wherein the regulatory element is non-naturally occurring.

3. The expression cassette of claim 1, wherein the regulatory element comprises SEQ ID NO: 3 or SEQ ID NO: 4.

4. The expression cassette of claim 1, wherein the regulatory element of (ii) is located between the promoter and the therapeutic transgene.

5. The expression cassette of claim 1, wherein the regulatory element comprises a sequence selected from the group consisting of SEQ ID NOS: 13-17 and 22-41.

6. The expression cassette of claim 5, wherein the regulatory element is the only promoter in the expression cassette.

7. The expression cassette of claim 1, wherein the regulatory element is no more than 120 base pairs (bp).

8. The expression cassette of claim 1, wherein the regulatory element is no more than 60 bp.

9. The expression cassette of claim 1, wherein the regulatory element is no more than 100 bp.

10. The expression cassette of claim 1, wherein the expression cassette is part of a recombinant adeno-associated virus (rAAV).

11. The expression cassette of claim 10, wherein the rAAV is an rAAV1, rAAV2, rAAV3, rAAV3b, rAAV4, rAAV5, rAAV6, rAAV7, rAAV8, rAAV9, rAAV10, rAAV11, rAAV12, rAAV-DJ, or rscAAV.

12. The expression cassette of claim 1, wherein the therapeutic transgene is a DNA binding protein, a gene editing protein, a transcriptional activator, or a transcriptional repressor.

13. The expression cassette of claim 1, wherein the therapeutic transgene is ATP7A, ATP7B, ATP8B1, ABCB4, ABCB11, CKDL5, CNTNAP2, ZEB2, Factor 1, Factor 2, Factor 3, Factor 4, Factor 5, Factor 6, Factor 7, Factor 8, Factor 9, Factor 10, Factor 11, or Factor 12.

14. The expression cassette of claim 1, wherein the therapeutic transgene is ATP7B.

15. An expression vector comprising the expression cassette of claim 1.

16. A viral particle comprising the expression cassette of claim 1.

17. The viral particle of claim 16, wherein the viral particle is an adeno-associated virus (AAV).

18. The viral particle of claim 17, wherein the AAV is selected from the group consisting of: AAV1, AAV2, AAV3, AAV3b, AAV4, AAV5, AAV6, AAV7, AAV8, AAV9, AAV10, AAV11, AAV12, AAV-DJ, and scAAV.

19. The expression cassette of claim 1, wherein the regulatory element is the sequence of SEQ ID NO: 2 operably linked to the promoter.

20. The expression cassette of claim 1, wherein the regulatory element is the sequence of SEQ ID NO: 14.

21. An adeno-associated virus (AAV) expression cassette comprising a human-derived regulatory element of no more than 120 bp operably linked to a transgene of at least 3 kb, wherein the regulatory element results in increased transgene expression by at least 2 fold as compared to expression of the transgene when operably linked to a CMV promoter, and wherein the human-derived regulatory element comprises:
(i) a sequence selected from the group consisting of SEQ ID NOS: 13-17 and 22-41; or
(ii) a sequence selected from the group consisting of SEQ ID NO: 1, SEQ ID NO: 2, and a combination of SEQ ID NOS: 1 and 2;
wherein the human-derived regulatory element of (ii) is operably linked to a promoter.

22. The AAV expression cassette of claim 21, wherein the increased transgene expression is at least 50 fold as compared to expression of the transgene when operably linked to a CMV promoter.

23. The AAV expression cassette of claim 21, wherein the increased transgene expression is at least 100 fold as compared to expression of the transgene when operably linked to a CMV promoter.

24. The AAV expression cassette of claim 21, wherein the human-derived regulatory element exhibits a size-normalized expression activity that is at least 1.5 fold as compared to size-normalized expression activity of a CMV promoter operably linked to the transgene.

25. The AAV expression cassette of claim 21, wherein the increased transgene expression occurs in at least 2 different cell types.

26. The AAV expression cassette of claim 25, wherein the at least 2 different cell types are selected from the group consisting of: kidney cells, neurons, and liver cells.

27. The AAV expression cassette of claim 21, wherein the human-derived regulatory element comprises any one or more of: SEQ ID NOS: 13-17 and 22-41, and wherein no other promoter sequences are present in the expression cassette.

28. The AAV expression cassette of claim 21, wherein the transgene is ATP7A, ATP7B, ATP8B1, ABCB4, ABCB11, CDKL5, CNTNAP2, ZEB2, Factor 1, Factor 2, Factor 3, Factor 4, Factor 5, Factor 6, Factor 7, Factor 8, Factor 9, Factor 10, Factor 11, or Factor 12.

29. The AAV expression cassette of claim 21, wherein the transgene is ATP7B.

30. The AAV expression cassette of claim 21, wherein the AAV is selected from the group consisting of: AAV1, AAV2, AAV3, AAV3b, AAV4, AAV5, AAV6, AAV7, AAV8, AAV9, AAV10, AAV11, AAV12, AAV-DJ, and scAAV.

31. The AAV expression cassette of claim 30, wherein the AAV is AAV8 or AAV5.

32. An adeno-associated virus (AAV) expression cassette comprising a human-derived regulatory element of no more than 120 bp operably linked to a transgene of at least 3 kb; wherein the regulatory element results in increased transgene expression by at least 2 fold as compared to expression of the transgene when operably linked to a CMV promoter, wherein the human-derived regulatory element comprises any one or more of SEQ ID NOS: 13-17 and 22-41, and wherein no other promoter sequences are present in the expression cassette.

* * * * *

SEQUENCE LISTING

<160> NUMBER OF SEQ ID NOS: 41

<210> SEQ ID NO 1
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
gtaaggtaag aattgaattt ctcagttgaa ggatgcttac actcttgtcc atctag    56

```
<210> SEQ ID NO 2
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtgtgtatgc tcaggggctg ggaaaggagg ggagggagct ccggctcag                49

<210> SEQ ID NO 3
<211> LENGTH: 266
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gtgatgcggt tttggcagta catcaatggg cgtggatagc ggtttgactc acggggattt    60
ccaagtctcc accccattga cgtcaatggg agtttgtttt ggcaccaaaa tcaacgggac   120
tttccaaaat gtcgtaacaa ctccgcccca ttgacgcaaa tgggcggtag gcgtgtacgg   180
tgggaggtct atataagcag agctggtacc gtaaggtaag aattgaattt ctcagttgaa   240
ggatgcttac actcttgtcc atctag                                        266

<210> SEQ ID NO 4
<211> LENGTH: 259
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gtgatgcggt tttggcagta catcaatggg cgtggatagc ggtttgactc acggggattt    60
ccaagtctcc accccattga cgtcaatggg agtttgtttt ggcaccaaaa tcaacgggac   120
tttccaaaat gtcgtaacaa ctccgcccca ttgacgcaaa tgggcggtag gcgtgtacgg   180
tgggaggtct atataagcag agctggtacc gtgtgtatgc tcaggggctg ggaaggagg    240 ggagggagct ccggctcag                                                259

<210> SEQ ID NO 5
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtacttatat aaggggggtgg gggcgcgttc gtcctcagtc gcgatcgaac actcgagccg    60
agcagacgtg cctacggacc                                                80

<210> SEQ ID NO 6
<211> LENGTH: 279
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 6
ggggaggctg ctggtgaata ttaaccaagg tcaccccagt tatcggagga gcaaacaggg      60
gctaagtcca cgctagcgtc tgtctgcaca tttcgtagag cgagtgttcc gatactctaa     120
tctccctagg caaggttcat atttgtgtag gttacttatt ctccttttgt tgactaagtc     180
aataatcaga atcagcaggt ttggagtcag cttggcaggg atcagcagcc tgggttggaa     240 ggaggggta taaaagcccc ttcaccagga gaagccgtc                             279

<210> SEQ ID NO 7
<211> LENGTH: 262
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gtttgctgct tgcaatgttt gcccatttta gggtggacac aggacgctgt ggtttctgag      60
ccagggctag cgggcgactc agatcccagc cagtggactt agccctgtt tgctcctccg      120 ataactgggg tgaccttggt taatattcac cagcagcctc ccccgttgcc cctctggatc     180
cactgcttaa atacggacga ggacagggcc ctgtctcctc agcttcaggc accaccactg     240
acctgggaca gtgaatcgcc ac                                              262

<210> SEQ ID NO 8
<211> LENGTH: 203
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
tgatgcggtt ttggcagtac atcaatgggc gtggatagcg gtttgactca cggggatttc      60
caagtctcca ccccattgac gtcaatggga gtttgttttg gcaccaaaat caacgggact     120
ttccaaaatg tcgtaacaac tccgccccat tgacgcaaat gggcggtagg cgtgtacggt     180
gggaggtcta tataagcaga gct                                             203

<210> SEQ ID NO 9
<211> LENGTH: 251
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gtttgctgct tgcaatgttt gcccatttta gggtggacac aggacgctgt ggtttctgag      60
ccagggggcg actcagatcc cagccagtgg acttagcccc tgtttgctcc tccgataact     120
ggggtgacct tggttaatat tcaccagcag cctcccccgt tgcccctctg gatccactgc     180
ttaaatacgg acgaggacag ggccctgtct cctcagcttc aggcaccacc actgacctgg     240
gacagtgaat c                                                          251

<210> SEQ ID NO 10
<211> LENGTH: 304
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 10

```
cgttacataa cttacggtaa atggcccgcc tggctgaccg cccaacgacc cccgcccatt    60
gacgtcaata atgacgtatg ttcccatagt aacgccaata gggactttcc attgacgtca   120
atgggtggag tatttacggt aaactgccca cttggcagta catcaagtgt atcatatgcc   180
aagtacgccc cctattgacg tcaatgacgg taaatggccc gcctggcatt atgcccagta   240
catgacctta tgggactttc ctacttggca gtacatctac gtattagtca tcgctattac   300
catg                                                                304
```

<210> SEQ ID NO 11
<211> LENGTH: 1643
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
gttacataac ttacggtaaa tggcccgcct ggctgaccgc ccaacgaccc ccgcccattg    60
acgtcaataa tgacgtatgt tcccatagta acgccaatag ggactttcca ttgacgtcaa   120
tgggtggagt atttacggta aactgcccac ttggcagtac atcaagtgta tcatatgcca   180
agtacgcccc ctattgacgt caatgacggt aaatggcccg cctggcatta tgcccagtac   240
atgaccttat gggactttcc tacttggcag tacatctacg tattagtcat cgctattacc   300
atgggtcgag gtgagcccca cgttctgctt cactctcccc atctcccccc cctccccacc   360
cccaattttg tatttattta ttttttaatt attttgtgca gcgatggggg cggggggggg   420
ggggcgcgcg ccaggcgggg cggggcgggg cgaggggcg gggcggggcg aggcggagag    480
gtgcggcgg agccaatcag agcggcgcgc tccgaaagtt tccttttatg gcgaggcggc    540
ggcggcggcg gccctataaa aagcgaagcg cgcggcgggc gggagtcgct gcgttgcctt    600
cgccccgtgc cccgctccgc gccgcctcgc gccgcccgcc ccggctctga ctgaccgcgt    660
tactcccaca ggtgagcggg cgggacggcc cttctcctcc gggctgtaat tagcgcttgg    720
tttaatgacg gctcgtttct tttctgtggc tgcgtgaaag ccttaaaggg ctccgggagg    780
gccctttgtg cggggggggag cggctcgggg ggtgcgtgcg tgtgtgtgtg cgtggggagc    840
gccgcgtgcg gcccgcgctg cccggcggct gtgagcgctg cgggcgcggc gcgggcttt    900
gtgcgctccg cgtgtgcgcg aggggagcgc ggccggggc ggtgccccgc ggtgcggggg    960
ggctgcgagg ggaacaaagg ctgcgtgcgg ggtgtgtgcg tggggggtg agcagggggt   1020
gtgggcgcgg cggtcgggct gtaaccccccc cctgcacccc cctccccgag ttgctgagca   1080
cggcccggct cgggtgcgg ggctccgtgc ggggcgtggc gcggggctcg ccgtgccggg   1140
cggggggtgg cggcaggtgg gggtgccggg cggggcgggg ccgcctcggg ccgggagggg   1200
ctcgggggag gggcgcggcg gccccggagc gccggcggct gtcgaggcgc ggcgagccgc   1260
agccattgcc ttttatggta atcgtgcgag agggcgcagg gacttccttt gtcccaaatc   1320
tggcggagcc gaaatctggg aggcgccgcc gcacccccctc tagcgggcgc gggcgaagcg   1380
gtgcggcgcg gcaggaagg aaatgggcgg ggagggcctt cgtgcgtcgc cgcgccgccg   1440
tccccttctc catctccagc ctcggggctg ccgcaggggg acggctgcct tcgggggga   1500
cgggcaggg cgggggttcgg cttctggcgt gtgaccggcg gctctagagc ctctgctaac   1560
```

```
catgttcatg ccttcttctt tttcctacag ctcctgggca acgtgctggt tgttgtgctg      1620
tctcatcatt ttggcaaaga att                                              1643

<210> SEQ ID NO 12
<211> LENGTH: 231
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gctccggtgc ccgtcagtgg gcagagcgca catcgcccac agtccccgag aagttggggg       60 gagggggtcgg caattgaacc ggtgcctaga aaggtggcg cggggtaaac tgggaaagtg      120
atgtcgtgta ctggctccgc cttttccog agggtggggg agaaccgtat ataagtgcag      180
tagtcgccgt gaacgttctt tttcgcaacg ggtttgccgc cagaacacag g              231

<210> SEQ ID NO 13
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gtgatgacgt gtcccataag gccctcggt ctaaggcttc cctatttcct ggttcgccgg        60
cggccatttt gggtggaagc gatagctgag tggcggcggc tgctgattgt gttctag        117

<210> SEQ ID NO 14
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
gtgatgacgt gtcccatact tccgggtcag gtgggccggc tgtcttgacc ttctttgcgg       60
ctcggccatt ttgtcccagt cagtccggag gctgcggctg cagaagtacc gcctgcg        117

<210> SEQ ID NO 15
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gtgatgacgt gtcccatatt ttcatctcgc gagacttgtg agcggccatc ttggtcctgc       60
cctgacagat tctcctatcg gggtcacagg gacgctaaga ttgctacctg gactttc        117

<210> SEQ ID NO 16
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 16
gtgatgacgt gtcccatggc ctcattggat gagaggtccc acctcacggc ccgaggcggg    60
gcttctttgc gcttaaaagc cgagccgggc caatgttcaa atgcgcagct cttagtc    117

<210> SEQ ID NO 17
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gtgatgacgt gtcccatccc ccctccaccc cctagcccgc ggagcacgct gggatttggc    60 gccccctcc tcggtgcaac ctatataagg ctcacagtct gcgctcctgg tacacgc    117

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cattccagga ctgtccattc t                                             21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggcctgaacg tagaagtacc a                                             21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
accacagtcc atgccatcac                                               20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tccaccaccc tgttgctgta                                               20

<210> SEQ ID NO 22
<211> LENGTH: 100
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 22
cccccctcca cccctagcc cgcggagcac gctgggattt ggcgccccc tcctcggtgc    60 aacctatata aggctcacag tctgcgctcc tggtacacgc                       100

<210> SEQ ID NO 23
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
ggcctcattg gatgagaggt cccacctcac ggcccgaggc ggggcttctt tgcgcttaaa    60
agccgagccg ggccaatgtt caaatgcgca gctcttagtc                         100

<210> SEQ ID NO 24
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
gggtggggcc cgcgcgtata aaggggcgc aggcgggctg ggcgttccac aggccaagtg    60
cgctgtgctc gagggtgcc ggccaggcct gagcgagcga                         100

<210> SEQ ID NO 25
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
ggtgcgatat tcggattggc tggagtcggc catcacgctc cagctacgcc acttcctttt    60
cgtggcacta taaagggtgc tgcacggcgc ttgcatctct                         100

<210> SEQ ID NO 26
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
acttccgggt caggtgggcc ggctgtcttg accttctttg cggctcggcc attttgtccc    60
agtcagtccg gaggctgcgg ctgcagaagt accgcctgcg                         100

<210> SEQ ID NO 27
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 27
gctgagcgcg cgcgatgggg cgggaggttt ggggtcaagg agcaaactct gcacaagatg    60
gcggcggtag cggcagtggc ggcgcgtagg aggcggtgag                         100

<210> SEQ ID NO 28
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
attttcatct cgcgagactt gtgagcggcc atcttggtcc tgccctgaca gattctccta    60
tcggggtcac agggacgcta agattgctac ctggactttc                        100

<210> SEQ ID NO 29
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
tgggaccccc ggaaggcgga agttctaggg cggaagtggc cgagaggaga ggagaatggc    60
ggcggaaggc tggatttggc gttggggctg gggccggcgg                        100

<210> SEQ ID NO 30
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
aaggcccctc ggtctaaggc ttccctattt cctggttcgc cggcggccat tttgggtgga    60
agcgatagct gagtggcggc ggctgctgat tgtgttctag                        100

<210> SEQ ID NO 31
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
agtgacccgg aagtagaagt ggcccttgca ggcaagagtg ctggagggcg gcagcggcga    60
ccggagcggt aggagcagca atttatccgt gtgcagcccc                        100

<210> SEQ ID NO 32
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gggaggggcg cgctggggag cttcggcgca tgcgcgctga ggcctgcctg accgaccttc    60
agcagggctg tggctaccat gttctctcgc gcgggtgtcg                          100

<210> SEQ ID NO 33
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
actgcgcacg cgcgcggtcg caccgattca cgccccttc cggcgcctag agcaccgctg     60
ccgccatgtt gagggggga ccgcgaccag ctgggcccct                           100

<210> SEQ ID NO 34
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
ccctcgaggg gcggagcaaa aagtgaggca gcaacgcctc cttatcctcg ctcccgcttt    60
cagttctcaa taaggtccga tgttcgtgta taaatgctcg                          100

<210> SEQ ID NO 35
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
cttggtgacc aaatttgaaa aaaaaaaaaa accgcgccaa ctcatgttgt tttcaatcag    60
gtccgccaag tttgtattta aggaactgtt tcagttcata                          100

<210> SEQ ID NO 36
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
ggctgagcta tcctattggc tatcgggaca aaatttgctt gagccaatca aagtgctccg    60
tggacaatcg ccgttctgtc tataaaaagg tgaagcagcg                          100

<210> SEQ ID NO 37
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 37
ggaagtgcca gaccggaggt gcgtcattca ccggcgacgc cgatacggtt cctccaccga        60
ggcccatgcg aagctttcca ctatggcttc cagcactgtc                            100

<210> SEQ ID NO 38
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
ccctcgaggg gcggagcaaa aagtgaggca gcaacgcctc cttatcctcg ctcccgcttt        60
cagttctcaa taaggtccga tgttcgtgta taaatgctcg                            100

<210> SEQ ID NO 39
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
cttggtgacc aaatttgaaa aaaaaaaaaa accgcgccaa ctcatgttgt tttcaatcag        60
gtccgccaag tttgtattta aggaactgtt tcagttcata                            100

<210> SEQ ID NO 40
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
ggctgagcta tcctattggc tatcgggaca aaatttgctt gagccaatca aagtgctccg        60
tggacaatcg ccgttctgtc tataaaaagg tgaagcagcg                            100

<210> SEQ ID NO 41
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
ggaagtgcca gaccggaggt gcgtcattca ccggcgacgc cgatacggtt cctccaccga        60
ggcccatgcg aagctttcca ctatggcttc cagcactgtc                            100
```